US008895806B2

(12) United States Patent
Altmann et al.

(10) Patent No.: US 8,895,806 B2
(45) Date of Patent: Nov. 25, 2014

(54) FUCOSYL TRANSFERASE GENE

(75) Inventors: Friedrich Altmann, Vienna (AT); Jan Mucha, Lāb (SK); Haralt Leiter, Stockerau (AT); Josef Glossl, Vienna (AT); Erika Staudacher, Vienna (AT)

(73) Assignees: Friedrich Altmann, Vienna (AT); Jan Mucha, Lab (SK); Haralt Leiter, Stockerau (AT); Josef Glössl, Vienna (AT); Erika Staudacher, Vienna (AT)

( * ) Notice: Subject to any disclaimer, the term of this patent is extended or adjusted under 35 U.S.C. 154(b) by 228 days.

(21) Appl. No.: 13/471,759

(22) Filed: May 15, 2012

(65) Prior Publication Data

US 2013/0212740 A1    Aug. 15, 2013

Related U.S. Application Data

(63) Continuation of application No. 11/808,097, filed on Jun. 6, 2007, now Pat. No. 8,198,078, which is a continuation-in-part of application No. 09/913,858, filed as application No. PCT/AT00/00040 on Feb. 17, 2000, now abandoned.

(30) Foreign Application Priority Data

Feb. 18, 1999  (AT) .......................................... 270/99

(51) Int. Cl.
*C12N 9/10* (2006.01)
*C12P 19/18* (2006.01)
*C12P 21/00* (2006.01)
*C12Q 1/68* (2006.01)
*C12N 15/82* (2006.01)

(52) U.S. Cl.
CPC .......... *C12N 9/1051* (2013.01); *C12N 15/8201* (2013.01); *C12N 15/8218* (2013.01); *C12P 19/18* (2013.01); *C12P 21/005* (2013.01)
USPC ........................... 800/286; 435/69.1; 800/278

(58) Field of Classification Search
None
See application file for complete search history.

(56) References Cited

PUBLICATIONS

European Examination Report dated Apr. 28, 2008 issued in corresponding European Application No. 05 108 012.5.

Grabenhorst et al., "Genetic Engineering of Recombinant Glycoproteins and the Glycosylation Pathway in Mammalian Host Cells", Glycoconjugate Journal, 1999, vol. 16, pp. 81-97.
Wagner et al., "N-Acetyl-β-Glucosaminidase Accounts for Differences in Glycosylation of Influenza Virus Hemagglutinin Expressed in Insect Cells from a Baculovirus Vector", Journal of Virology, Jun. 1996, vol. 70, No. 6, pp. 4103-4109.
Ogonah et al., "Isolation and Characterization of an Insect Cell Line Able to Perform Complex N-Linked Glycosylation on Recombinant Proteins", Biotechnology, Feb. 1996, vol. 14, pp. 197-202.
Examination Report mailed Dec. 8, 2009, in corresponding Japanese Application No. 2000-599878 (and corresponding English language translation).
Nakanishi et al., "Molecular Cloning of Vacuolar H+-Pyrophosphatase and Its Developmental Expression in Growing Hypcotyl of Mung Bean1," Plant Physiol., 1998, vol. 116, pp. 589-597, American Society of Plant Physiologists, Lancaster, PA.
Staudacher et al., "Functional purification and characterization of a GDP-fucose: β-N-acetylglucsamine (Fuc to Asn linked GlcNAc) α1,3-fucosyltransferase from mung beans," Glycoconjugate Journal, 1995, vol. 12, pp. 780-786, Kluwer Academic Publishers, Boston, MA.
Altmann, "More than silk and honey-or, can insect cells serve in the production of therapeutic glycoproteins?" Glycoconjugate Journal, 1997, 14, pp. 643-646, Kluwer Academic Publishers, Boston, MA.
Lerouge et al., "N-Glycoprotein biosynthesis in plants: recent developments and future trends," Plant Molecular Biology, 1998, vol. 38, pp. 31-48, Kluwer Academic Publishers, Dordrecht, Holland.
Examination Report dated Jul. 13, 2010 in corresponding European Application No. 09154489.0.
Costache et al., "Evolution of Fucosyl Fucosyltransferase Genes in Vertebrates", Journal of Biological Chemistry, vol. 272, No. 47, pp. 29721-29728, The American Society for Biochemistry and Molecular Biology, Inc., US Lnkd, XP002925163, Nov. 21, 1991.
EMBL database AC:B67847, *Arabidopsis thaliana*, XP002140249 sequence, Sep. 12, 1997.
EMBL database AC:AQ158899, *Oryza sativa*, XP002140250 sequence, Sep. 9, 1998.
EMBL database AC:AQ328306, *Oryza sativa*, XP002140251 sequence, Nov. 1, 1999.

*Primary Examiner* — Sean McGarry
(74) *Attorney, Agent, or Firm* — Buchanan Ingersoll & Rooney PC

(57) ABSTRACT

A DNA molecule is provided which comprises a sequence according to SEQ ID NO: 1 having an open reading frame from base pair 211 to base pair 1740 or having at least 50% homology to the above-indicated sequence, or hybridizing with the above-indicated sequence under stringent conditions, or comprising a sequence which has degenerated to the above-indicated DNA sequence because of the genetic code, the sequence coding for a plant protein having fucosyltransferase activity or being complementary thereto.

14 Claims, 26 Drawing Sheets

1   KPDAxFGLPQPSTAS

2   PETVYHIYVR

3   MESAEYYAENNIA

4   GRFEMESIYL

```
                                          A
S1  5'-GCIGAATACTACGCIGAAAACAACATCGC-3'
        G   T  T      G   T  T  T

A
A2  5'-CATAGATATGATAIACIGTCTC-3'
        G  T  G  G        T

A
A3  5'-TAGATICACTCCATCTCAAA-3'
        T  GTT      T  G
```

FIG. 4

```
ACTAACTCAA ACGCTGCATT TTCTTTTTTC TTTCAGGGAA CCATCCACCC ATAACAACAA   60
AAAAAACAAC AGCAAGCTGT GTTTTTTTTA TCGTTCTTTT TCTTTAAACA AGCACCCCCA  120
TCATGGAATC GTGCTCATAA CGCCAAAATT TTCCATTTCC CTTTGATTTT TAGTTTATTT  180
TGCGGAATTG GCAGTTGGGG GCGCAATTGA ATGATGGGTC TGTTGACGAA TCTTCGAGGC  240
TCGAGAACAG ATGGTGCCCA ACAAGACAGC TTACCCGTTT TGGCTCCGGG AGGCAACCCA  300
AAGAGGAAAT GGAGCAATCT AATGCCTCTT GTTGTTGCCC TTGTGGTCAT CGCGGAGATC  360
GCGTTTCTGG GTAGGTTGGA TATGGCCAAA AACGCCGCCA TGGTTGACTC CCTCGCTGAC  420
TTCTTCTACC GCTCTCGAGC GGTCGTTGAA GGTGACGATT TGGGGTTGGG TTTGGTGGCT  480
TCTGATCGGA ATTCTGAATC GTATAGTTGT GAGGAATGGT TGGAGAGGGA GGATGCTGTC  540
ACGTATTCGA GGGGCTTTTC CAAAGAGCCT ATTTTTGTTT CTGGAGCTGA TCAGGAGTGG  600
AAGTCGTGTT CGGTTGGATG TAAATTTGGG TTTAGTGGGG ATAGAAAGCC AGATGCCGCA  660
TTTGGGTTAC CTCAACCAAG TGGAACAGCT AGCATTCTGC GATCAATGGA ATCAGCAGAA  720
TACTATGCTG AGAACAATAT TGCCATGGCA AGACGGAGGG GATATAACAT CGTAATGACA  780
ACCAGTCTAT CTTCGGATGT TCCTGTTGGA TATTTTTCAT GGGCTGAGTA TGATATGATG  840
GCACCAGTGC AGCCGAAAAC TGAAGCTGCT CTTGCAGCTG CTTTCATTTC CAATTGTGGT  900
GCTCGAAATT TCCGGTTGCA AGCTCTTGAG GCCCTTGAAA AATCAAACAT CAAAATTGAT  960
TCTTATGGTG GTTGTCACAG GAACCGTGAT GGAAGAGTGA ACAAAGTGGA AGCCCTGAAG 1020
CACTACAAAT TTAGCTTAGC GTTTGAAAAT TCGAATGAGG AAGATTATGT AACTGAAAAA 1080
TTCTTCCAAT CCCTTGTTGC TGGAACTGTC CCTGTGGTTG TTGGTGCTCC AAATATTCAG 1140
```

FIG. 5a

```
GACTTTGCTC CTTCTCCTGG TTCAATTTTA CATATTAAAG AGATAGAGGA TGTTGAGTCT 1200
GTTGCAAAGA CCATGAGATA TCTAGCAGAA AATCCCGAAG CATATAATCA ATCATTGAGG 1260
TGGAAGTATG AGGGTCCATC TGACTCCTTC AAGGCCCTTG TGGATATGGC AGCTGTGCAT 1320
TCATCGTGCC GTCTTTGCAT TCACTTGGCC ACAGTGAGTA GAGAGAAGGA AGAAAATAAT 1380
CCAAGCCTTA AGAGACGTCC TTGCAAGTGC ACTAGAGGGC CAGAAACCGT ATATCATATC 1440
TATGTCAGAG AAAGGGGAAG GTTTGAGATG GAGTCCATTT ACCTGAGGTC TAGCAATTTA 1500
ACTCTGAATG CTGTGAAGGC TGCTGTTGTT TTGAAGTTCA CATCCCTGAA TCTTGTGCCT 1560
GTATGGAAGA CTGAAAGGCC TGAAGTTATA AGAGGGGGGA GTGCTTTAAA ACTCTACAAA 1620
ATATACCCAA TTGGCTTGAC ACAGAGACAA GCTCTTTATA CCTTCAGCTT CAAAGGTGAT 1680
GCTGATTTCA GGAGTCACTT GGAGAACAAT CCTTGTGCCA AGTTTGAAGT CATTTTTGTG 1740
TAGCATGCGC TAAATGGTAC CTCTGCTCTA CCTGAATTAG CTTCACTTAG CTGAGCACTA 1800
GCTAGAGTTT TAGGAATGAG TATGGCAGTG AATATGGCAT GGCTTTATTT ATGCCTAGTT 1860
TCTTGGCCAA CTCATTGATG TTTTGTATAA GACATCACAC TTTAATTTTA AACTTGTTTC 1920
TGTAGAAGTG CAAATCCATA TTTAATGCTT AGTTTTAGTG CTCTTATCTG ATCATCTAGA 1980
AGTCACAGTT CTTGTATATT GTGAGTGAAA ACTGAAATCT AATAGAAGGA TCAGATGTTT 2040
CACTCAAGAC ACATTATTAC TTCATGTTGT TTTGATGATC TCGAGCTTTT TTAGTGTCTG 2100
GAACTGTCCC TGTGGTTTGA GCACCTGTTA TTGCTTCAGT GTTACTGTCC AGTGGTTATC 2160
GTTTTTGACC TCTAAAAAAA AAAAAAAAAA AAAAAAA                           2198
```

FIG. 5b

```
Met Met Gly Leu Leu Thr Asn Leu Arg Gly Ser Arg Thr Asp Gly Ala
1              5                    10                 15
Gln Gln Asp Ser Leu Pro Val Leu Ala Pro Gly Gly Asn Pro Lys Arg
            20              25                  30
Lys Trp Ser Asn Leu Met Pro Leu Val Val Ala Leu Val Val Ile Ala
        35              40                  45
Glu Ile Ala Phe Leu Gly Arg Leu Asp Met Ala Lys Asn Ala Ala Met
    50              55                  60
Val Asp Ser Leu Ala Asp Phe Phe Tyr Arg Ser Arg Ala Val Val Glu
65              70                  75                      80
Gly Asp Asp Leu Gly Leu Gly Leu Val Ala Ser Asp Arg Asn Ser Glu
                85                  90                  95
Ser Tyr Ser Cys Glu Glu Trp Leu Glu Arg Glu Asp Ala Val Thr Tyr
            100             105                 110
Ser Arg Gly Phe Ser Lys Glu Pro Ile Phe Val Ser Gly Ala Asp Gln
        115             120                 125
Glu Trp Lys Ser Cys Ser Val Gly Cys Lys Phe Gly Phe Ser Gly Asp
    130             135                 140
Arg Lys Pro Asp Ala Ala Phe Gly Leu Pro Gln Pro Ser Gly Thr Ala
145             150                 155                     160
Ser Ile Leu Arg Ser Met Glu Ser Ala Glu Tyr Tyr Ala Glu Asn Asn
            165             170                 175
Ile Ala Met Ala Arg Arg Arg Gly Tyr Asn Ile Val Met Thr Thr Ser
        180             185                 190
Leu Ser Ser Asp Val Pro Val Gly Tyr Phe Ser Trp Ala Glu Tyr Asp
    195             200                 205
Met Met Ala Pro Val Gln Pro Lys Thr Glu Ala Ala Leu Ala Ala Ala
210             215                 220
Phe Ile Ser Asn Cys Gly Ala Arg Asn Phe Arg Leu Gln Ala Leu Glu
225             230                 235                     240
```

FIG. 6a

```
Ala Leu Glu Lys Ser Asn Ile Lys Ile Asp Ser Tyr Gly Gly Cys His
                245                 250                 255
Arg Asn Arg Asp Gly Arg Val Asn Lys Val Glu Ala Leu Lys His Tyr
            260                 265                 270
Lys Phe Ser Leu Ala Phe Glu Asn Ser Asn Glu Glu Asp Tyr Val Thr
        275                 280                 285
Glu Lys Phe Phe Gln Ser Leu Val Ala Gly Thr Val Pro Val Val Val
    290                 295                 300
Gly Ala Pro Asn Ile Gln Asp Phe Ala Pro Ser Pro Gly Ser Ile Leu
305                 310                 315                 320
His Ile Lys Glu Ile Glu Asp Val Glu Ser Val Ala Lys Thr Met Arg
                325                 330                 335
Tyr Leu Ala Glu Asn Pro Glu Ala Tyr Asn Gln Ser Leu Arg Trp Lys
            340                 345                 350
Tyr Glu Gly Pro Ser Asp Ser Phe Lys Ala Leu Val Asp Met Ala Ala
        355                 360                 365
Val His Ser Ser Cys Arg Leu Cys Ile His Leu Ala Thr Val Ser Arg
    370                 375                 380
Glu Lys Glu Glu Asn Asn Pro Ser Leu Lys Arg Arg Pro Cys Lys Cys
385                 390                 395                 400
Thr Arg Gly Pro Glu Thr Val Tyr His Ile Tyr Val Arg Glu Arg Gly
                405                 410                 415
Arg Phe Glu Met Glu Ser Ile Tyr Leu Arg Ser Ser Asn Leu Thr Leu
            420                 425                 430
Asn Ala Val Lys Ala Ala Val Val Leu Lys Phe Thr Ser Leu Asn Leu
        435                 440                 445
Val Pro Val Trp Lys Thr Glu Arg Pro Glu Val Ile Arg Gly Gly Ser
    450                 455                 460
Ala Leu Lys Leu Tyr Lys Ile Tyr Pro Ile Gly Leu Thr Gln Arg Gln
465                 470                 475                 480
Ala Leu Tyr Thr Phe Ser Phe Lys Gly Asp Ala Asp Phe Arg Ser His
                485                 490                 495
Leu Glu Asn Asn Pro Cys Ala Lys Phe Glu Val Ile Phe Val
            500                 505                 510
```

FIG. 6b

| Transferase | Art | # | konserviertes Motive |
|---|---|---|---|
| FucT-C3 | Mungo Bohne | P21217 | 267-EALKHYKFSLAFENSNEEDYVTEKFFQ-SLVAGTVP |
| FucT-III | Mensch | O19058 | 236-ETLSRYKFYLAFENSLHPDYITEKLWRNALEAWAVP |
| FucT-III | Schimpanse | Q11128 | 247-ETLSRYKFYLAFENSLHPDYITEKLWRNALEAWAVP |
| FucT-V | Mensch | P56433 | 249-ETLSRYKFYLAFENSLHPDYITEKLWRNALEAWAVP |
| FucT-V | Schimpanse | P51993 | 249-ETLSRYKFYLAFENSLHPDYITEKLWRNALEAWAVP |
| FucT-VI | Mensch | P56434 | 235-ETLSRYKFYLAFENSLHPDYITEKLWRNALEAWAVP |
| FucT-VI | Schimpanse | Q11126 | 235-ETLSRYKFYLAFENSLHPDYITEKLWRNALEAWAVP |
| Fuc-T-III | Rind | O35886 | 240-KQLSQYKFYLAFENSLHPDYITEKLWKNALEAWAVP |
| Fuc-T-? | chin. Hamster | Q11130 | 237-GTLARYKFYLAFENSLHPDYITEKLWRNALVAGTVP |
| FucT-VII | Mensch | Q11131 | 217-PTVAQYRFYLSFENSQHRDYITEKFWRNALVAGTVP |
| FucT-VII | Maus | O76204 | 264-PTLARYRFYLAFENSQHRDYITEKFWRNALAAGAVP |
| FucT-VII | Schistosoma mansonii | P22083 | 226-PTLARYRFYLAFENSQHRDYITEKFWRNALAAGAVP |
| FucT-IV | Mensch | Q11127 | 277-HTVARYKFYLAFENSQHLDYITEKLWRNALLAGAVP |
| FucT-IV | Maus | Q62994 | 305-HTVARYKFYLAFENSRHVDYITEKLWRNAFLAGAVP |
| FucT-IV | Ratte | Q98952 | 305-HTVARYKFYLAFENSQHVDYNTEKLWRNAFLAGAVP |
| FucT-IV | Huhn | O88819 | 228-KTVSAYKFYLAFENSQHTDYITEKLWKNAFAASAVP |
| FucT-IX | Maus | O76544 | 233-PTISTCKFYLSFENSIHKDYITEKLWE-SLSVGTIP |
| FutA | Dictyostelium discoideum | O32631 | 247-DVLKRYNFALAFENSLCKDYITEKLYNAFL-AGSVP |
| hpFucT1 | Helicobacter pylori | O30511 | 106-EFLSQYKFNLCFENSQGYGYVTEKILD-AYFSHTIP |
| hpFucT2 | Helicobacter pylori | Q21362 | 227-EFLSQYKFNLCFENTQGYGYVTEKIID-AYFSHTIP |
| CEFT-1 | Caenorhabditis elegans |  | 303-MLDTDYHFYVTFENSICEDYVTEKLWKSGYQNTIIP |

*Zugriffsnummer fur de SwissProt Protein Sequenz Datenbank

FIG. 8

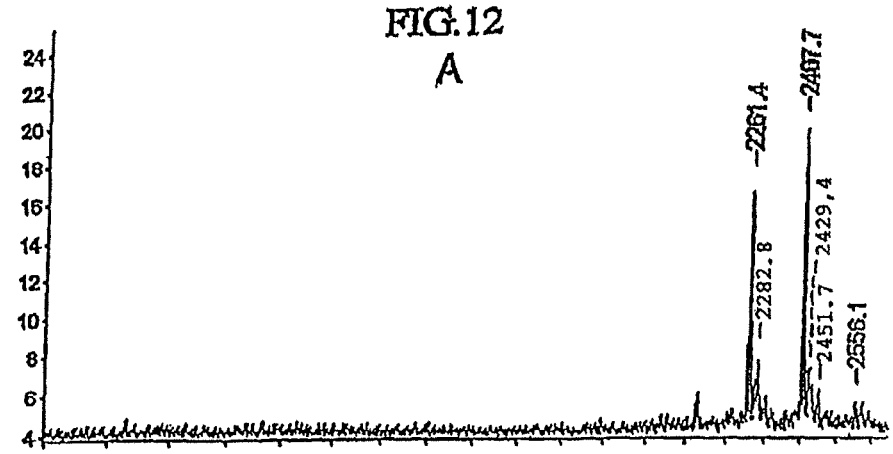
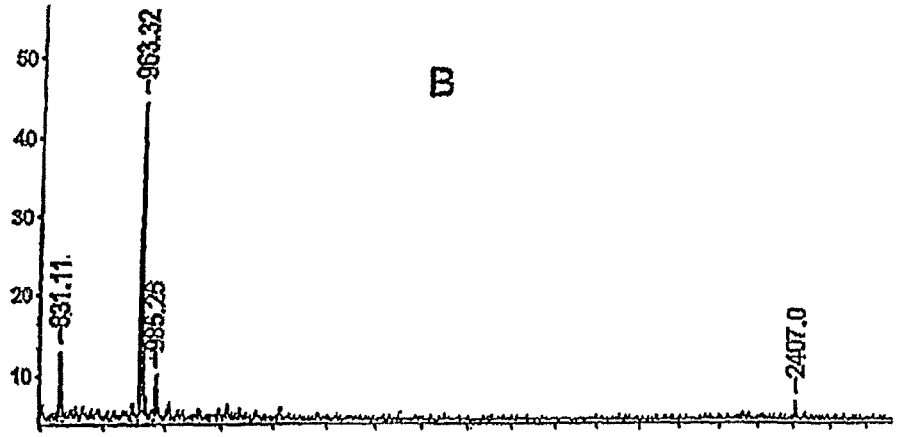
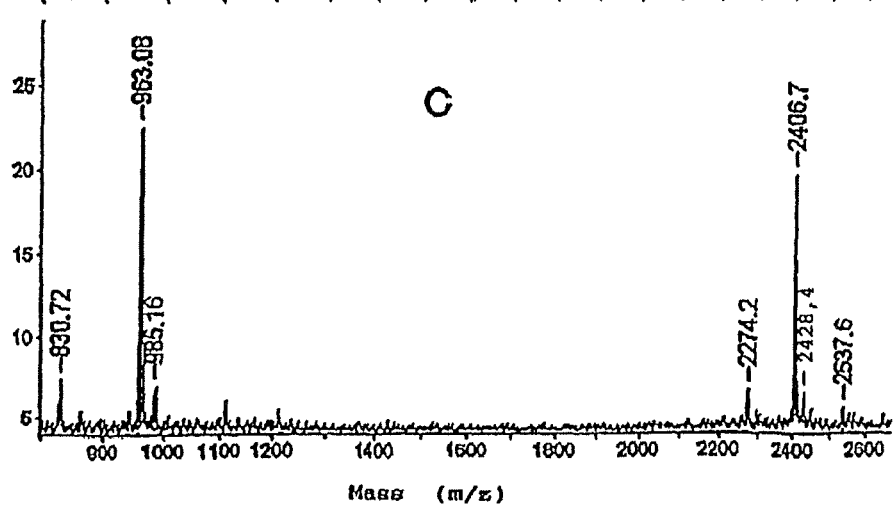
FIG. 12

```
-210                                    ACTAACTCAAACGCTGCATTTTCTTTTTTC -181
-180 TTTCAGGGAACCATCCACCCATAACAACAAAAAAAAACAACAGCAAGCTGTGTTTTTTTA -121
-120 TCGTTCTTTTTCTTTAAACAAGCACCCCCATCATGGAATCGTGCTCATAACGCCAAAATT -  61
- 60 TTCCATTTCCCTTTGATTTTTAGTTTTATTTTGCGGAATTGGCAGTTGGGGGCGCAATTGA -  1
   1 ATGATGGGTCTGTTGACGAATCTTCGAGGCTCGAGAACAGATGGTGCCCAACAAGACAGC   60
   1  M  M  G  L  L  T  N  L  R  G  S  R  T  D  G  A  Q  Q  D  S   20
  61 TTACCCGTTTTGGCTCCGGGAGGCAACCCAAAGAGGAAATGGAGCAATCTAATGCCTCTT  120
  21  L  P  V  L  A  P  G  G  N  P  K  R  K  W  S  N  L  M  P  L   40
 121 GTTGTTGCCCTTGTGGTCATCGCGGAGATCGCGTTTCTGGGTAGGTTGGATATGGCCAAA  181
  41  V  V  A  L  V  V  I  A  E  I  A  F  L  G  R  L  D  M  A  K   60
 181 AACGCCGCCATGGTTGACTCCCTCGCTGACTTCTTCTACCGCTCTCGAGCGGTCGTTGAA  240
  61  N  A  A  M  V  D  S  L  A  D  F  F  Y  R  S  R  A  V  V  E   80
 241 GGTGACGATTTGGGGTTGGGTTTGGTGGCTTCTGATCGGAATTCTGAATCGTATAGTTGT  300
  81  G  D  D  L  G  L  G  L  V  A  S  D  R  N  S  E  S  Y  S  C  100
 301 GAGGAATGGTTGGAGAGGGAGGATGCTGTCACGTATTCGAGGGGCTTTTCCAAAGAGCCT  360
 101  E  E  W  L  E  R  E  D  A  V  T  Y  S  R  G  F  S  K  E  P  120
 361 ATTTTTGTTTCTGGAGCTGATCAGGAGTGGAAGTCGTGTTCGGTTGGATGTAAATTTGGG  420
 121  I  F  V  S  G  A  D  Q  E  W  K  S  C  S  V  G  C  K  F  G  140
 421 TTTAGTGGGGATAGAAAGCCAGATGCCGCATTTGGGTTACCTCAACCAAGTGGAACAGCT  480
 141  F  S  G  D  R  K  P  D  A  A  F  G  L  P  Q  P  S  G  T  A  160
 481 AGCATTCTGCGATCAATGGAATCAGCAGAATACTATGCTGAGAACAATATTGCCATGGCA  540
 161  S  I  L  R  S  M  E  S  A  E  Y  Y  A  E  N  N  I  A  M  A  180
 541 AGACGGAGGGGATATAACATCGTAATGACAACCAGTCTATCTTCGGATGTTCCTGTTGGA  600
 181  R  R  R  G  Y  N  I  V  M  T  T  S  L  S  S  D  V  P  V  G  200
 601 TATTTTTCATGGGCTGAGTATGATATGATGGCACCAGTGCAGCCGAAAACTGAAGCTGCT  660
 201  Y  F  S  W  A  E  Y  D  M  M  A  P  V  Q  P  K  T  E  A  A  220
 661 CTTGCAGCTGCTTTCATTTCCAATTGTGGTGCTCGAAATTTCCGGTTGCAAGCTCTTGAG  720
 221  L  A  A  A  F  I  S  N  C  G  A  R  N  F  R  L  Q  A  L  E  240
 721 GCCCTTGAAAAATCAAACATCAAAATTGATTCTTATGGTGGTTGTCACAGGAACCGTGAT  780
 241  A  L  E  K  S  N  I  K  I  D  S  Y  G  G  C  H  R  N  R  D  260
 781 GGAAGAGTGAACAAAGTGGAAGCCCTGAAGCACTACAAATTTAGCTTAGCGTTTGAAAAT  840
 261  G  R  V  N  K  V  E  A  L  K  H  Y  K  F  S  L  A  F  E  N  280
 841 TCGAATGAGGAAGATTATGTAACTGAAAAATTCTTCCAATCCCTTGTTGCTGGAACTGTC  900
 281  S  N  E  E  D  Y  V  T  E  K  F  F  Q  S  L  V  A  G  T  V  300
 901 CCTGTGGTTGTTGGTGCTCCAAATATTCAGGACTTTGCTCCTTCTCCTGGTTCAATTTTA  960
 301  P  V  V  V  G  A  P  N  I  Q  D  F  A  P  S  P  G  S  I  L  320
 961 CATATTAAAGAGATAGAGGATGTTGAGTCTGTTGCAAAGACCATGAGATATCTAGCAGAA 1020
 321  H  I  K  E  I  E  D  V  E  S  V  A  K  T  M  R  Y  L  A  E  340
1021 AATCCCGAAGCATATAATCAATCATTGAGGTGGAAGTATGAGGGTCCATCTGACTCCTTC 1080
 341  N  P  E  A  Y  N  Q  S  L  R  W  K  Y  E  G  P  S  D  S  F  360
1081 AAGGCCCTTGTGGATATGGCAGCTGTGCATTCATCGTGCCGTCTTTGCATTCACTTGGCC 1140
 361  K  A  L  V  D  M  A  A  V  H  S  S  C  R  L  C  I  H  L  A  380
1141 ACAGTGAGTAGAGAGAAGGAAGAAAATAATCCAAGCCTTAAGAGACGTCCTTGCAAGTGC 1200
 381  T  V  S  R  E  K  E  E  N  N  P  S  L  K  R  R  P  C  K  C  400
1201 ACTAGAGGGCCAGAAACCGTATATCATATCTATGTCAGAGAAAGGGGAAGGTTTGAGATG 1260
 401  T  R  G  P  E  T  V  Y  H  I  Y  V  R  E  R  G  R  F  E  M  420
1261 GAGTCCATTTACCTGAGGTCTAGCAATTTAACTCTGAATGCTGTGAAGGCTGCTGTTGTT 1320
 421  E  S  I  Y  L  R  S  S  N  L  T  L  N  A  V  K  A  A  V  V  440
1321 TTGAAGTTCACATCCCTGAATCTTGTGCCTGTATGGAAGACTGAAAGGCCTGAAGTTATA 1380
 441  L  K  F  T  S  L  N  L  V  P  V  W  K  T  E  R  P  E  V  I  460
1381 AGAGGGGGGAGTGCTTTAAAAACTCTACAAAATATACCCAATTGGCTTGACACAGAGACAA 1440
 461  R  G  G  S  A  L  K  L  Y  K  I  Y  P  I  G  L  T  Q  R  Q  480
1441 GCTCTTTATACCTTCAGCTTCAAAGGTGATGCTGATTTCAGGAGTCACTTGGAGAACAAT 1500
 481  A  L  Y  T  F  S  F  K  G  D  A  D  F  R  S  H  L  E  N  N  500
1501 CCTTGTGCCAAGTTTGAAGTCATTTTTGTGTAGCATGCGCTAAATGGTACCTCTGCTCTA 1560
 501  P  C  A  K  F  E  V  I  F  V  *                             
1561 CCTGAATTAGCTTCACTTAGCTGAGCACTAGCTAGAGTTTTAGGAATGAGTATGGCAGTG 1620
1621 AATATGGCATGGCTTGCTTTTATTTATGCCTAGTTTCTTGCCAACTCATTGATGTTTTGTATAA 1680
1681 GACATCACACTTTAATTTTAAACTTGTTTCTGTAGAAGTGCAAATCCATATTTAATGCTT 1740
1741 AGTTTTAGTGCTCTTATCTGATCATCTAGAAGTCACAGTTCTTGTATATTGTGAGTGAAA 1800
1801 ACTGAAATCTAATAGAAGGATCAGATGTTTCACTCAAGACACATTATTACTTCATGTTGT 1860
1861 TTTGATGATCTCGAGCTTTTTTAGTGTCTGGAACTGTCCCTGTGGTTTGAGCACCTGTTA 1920
1921 TTGCTCAGTGTGTTACTGTCCAGTGGTTATCGTTTTTGACCTCTAAAAAAAAAAAAAAAA 1980
1981 AAAAAAAA
```

```
Fuct 1,3 Vx   472 ypigltqrqalytfskgdedfrshlemrpyakfevifv
Fuct 1,3 Zm   460 ypvgltqrqalygfrfrddseleqyikdhpcaklevifv
Fuct 1,3 At1  463 ypigltqrqalymfkfegnsslsthiqrnpcpkfevvfv
Fuct 1,3 At2  475 ypigltqrqalynfkkegnasisshiqnnpcakfevvtv
Fuct 1,3 Lm   452 ypvgitqrealfsfqmtdkelqiyleshpcakfevlfi
Fuct 1,3 Nt   466 ypagltqrqalytfkfngdvdfrshlesnpcakfevvfv
Fuct 1,3 Os   475 ypigltqrqalygfrfrddadldkyikdhpcaklevifv
Fuct 1,3 Pp   495 ypvgltqrealytwdfsggdkgikamvqkqpclqlevrfv
```

```
FucT 1,3 Vr   412 vrergrfemesiylrssnltlnavkaavvlkftslnlvpvwkterpevirggsalklykiypigltqrqalytfsfkgdedfrshlennpyakfevifv
FucT 1,3 Pp   435 vrergrfemesvflegskslahlkgvvdkftalkhvplwkkerpevirgnsdlrlykiypvgltqreealytwdfggdkgikamvqkqpclqlevvfv
FucT 1,3 Ht   406 vrergrfemesiylrssnltlesfktavltkftslnhvpvwkperpeilkggdelkvykiypagltqrqalytkfngdvdfrshlesnpcakfevvfv
FucT 1,3 At1  403 vrergrfdmesiflkdgnltlealesavlakfmslryep
FucT 1,3 At2  415 vrergrfemesvflrgksvtqealesavlakfkslkheavwkkerpgnlkgdkelkihrlyplgltqrqalynfktegnsslsshiqnnpcakfevvfv
FucT 1,3 Zm   400 irergrfksaslymrsgqltlgalesavlgkfrslnhvpvwkderppsirgddlklyrlypvgltqrqalygfirtrddseleqyikdhpcaklevifv
FucT 1,3 Os   415 vrergrfktesllrsdqltmgalesavlakfrslnhvpvwkderppsirggdelkvykiypigltqrqalyqfirfrddsndidkylkdhpcaklevifv
FucT 1,3 Lm   392 arergrfcdflslfmrsdnlslkalgstvlekfsslkhvplwkkerpesikggsklidlyrlypvgltqrealfsfcfntdkelqiyleshpcakievifi
FucT 1,4 Ht   402                                        kggrmars-
FucT 1,4 At   394 -gr                                    -
FucT 1,4 Pp   433 -nsv                                   rggknagv
FucT 1,4 Os   412 vskrgg                                 rnadal
```

FIG. 18

```
          1 --mpmrylnamaalmm------fftlllsftg-----ilefp-----------sastsmehsidpepkl--sdstsd-------pfsdv-----------lvaykkv
Fuct 1,4 At
Fuct 1,4 Ht   1 mpgpkpfntititml------aftfllllltg-----flqfp-----------sisrslpgplhdsftlpstntssk-------pftdl-----------vssftkw
Fuct 1,4 Pp   1 m-epsgfllrytkiqlircavsfsfvllvfalttscnftrkfpdivaraagkdtsrtddttrsvpcvkev--deaege--------hgsqmdfgshsetvlgsrdytaw
Fuct 1,4 Os   1 mlfpkr-lnymapmlas-------avillll-vsg--yfelp-----------siss--ysaapappl--fataldavgtrerspftsl-----------lsafadw Fuct 1,4 At  66 dfevgcarfze------------nhkdalignvssgsiqef------g----cgklmkhvkvlvkgwtwlpdnlenlyscrcgmtclwtkssvladspdallfetttpp
Fuct 1,4 Ht  70 dsqvgcakfze------------ktngvlinqskivsiqei-----------ggdkvckgfkmnhvsvlvkgwtwlpdnldnlyscrcglsclwtksnvladkpdalmfesstpp
Fuct 1,4 Pp 100 dtrvgcgnfkk------------kys--ygnrtsstlrslqmptvdn-----ctilrkghvsvlvkkwtwlpdtlnnlyscdcgltclwtnscdvlldrpdahlyesatpp
Fuct 1,4 Os  71 daavgcprlraekldavgapqyganstaeaeasitggagwgg----------ggggrcegvrtrlhvgvlvkgwtwlpdaldgvyytcrcgvscvwsksaaavdrpdallfegatpp Fuct 1,4 At 154 lgrrvgdplrvymeleagrkrsgredlfisyhakddvqttyagslfhnncnylnisphknndvlvywsssrclphrdrlaksllldllphhsfgkclnnvggldsalsmype
Fuct 1,4 Ht 162 lgrhvgeplraymdleegrkrsgredlylsyhaeddvgstyegalfhngrnyhwsmtkssdvlvywsssrclpqrmelakkllglllphhsfgkclnnvggqnmalsffpe
Fuct 1,4 Pp 191 srrrkgepwrlymdlepggnrapsqdlfvsynanodlqvtyagaafhtlrnyyispvkhddvlvywsssrcvestqriasevlgflphhsfgkclnnvggmdvllemypk
Fuct 1,4 Os 175 pgrmkglplrvyldleaarkptgfedlfigyhakddvqtyagksfhtsrsyhvstekrncdallywssscplphrdrvakdflslvphhsfgkclnnvdgpdmalsmypv Fuct 1,4 At 264 cvaehnaeakwydhlhcamshykfvlalentaavesyvteklfyaldsgsvpiyfgasnvqdfvpphsvldgskfgsmqelaayvkrlgddpvayseyhawrrcglmgnyg
Fuct 1,4 Ht 272 cendenakpkwdhlhcamshykfvlalenttesyvteklfyaldsgavplyfgapnvmdfvpphslldgrtkfksveelasyvkavandpvayaeyhawrrcgvmgnya
Fuct 1,4 Pp 301 csssgegmvwmqlhcamshykfvlalensqlesyateklyyaldagavplyfgapnvedfvpphslgrnfatlgglaeyvkkvaadpvlyaeyhawrrcglgvyg
Fuct 1,4 Os 285 cstndngkpwwdhlhcamshykfvlalentkteesyvteklfyaleagsvplyfgapnvwdflppnslldaskfsslrelasyrkavandpvayaeyhawrcglgnfg Fuct 1,4 At 374 ktravsldtlpcrlceelsrrggknagv-
Fuct 1,4 Ht 382 kramsldtlpcrlceavsrkggrnars-
Fuct 1,4 Pp 411 rtravsldslpcrlcaavssrggnsv-
Fuct 1,4 Os 395 rsrensldtlpcrlcelvskrggrnadal
```

FIG. 19

SEQUENCE LISTING

<160> NUMBER OF SEQ ID NOS: 59

<210> SEQ ID NO 1
<211> LENGTH: 2198
<212> TYPE: DNA
<213> ORGANISM: Vigna radiata

<400> SEQUENCE: 1

```
actaactcaa acgctgcatt ttcttttttc tttcagggaa ccatccaccc ataacaacaa      60
aaaaaacaac agcaagctgt gttttttta tcgttctttt tctttaaaca agcacccca      120
tcatggaatc gtgctcataa cgccaaaatt ttccatttcc ctttgatttt tagtttattt     180
tgcggaattg gcagttgggg gcgcaattga atgatgggtc tgttgacgaa tcttcgaggc     240
tcgagaacag atggtgccca acaagacagc ttacccgttt tggctccggg aggcaaccca     300
aagaggaaat ggagcaatct aatgcctctt gttgttgccc ttgtggtcat cgcggagatc     360
gcgtttctgg gtaggttgga tatggccaaa acgccgcca tggttgactc cctcgctgac     420
ttcttctacc gctctcgagc ggtcgttgaa ggtgacgatt tggggttggg tttggtggct     480
tctgatcgga attctgaatc gtatagttgt gaggaatggt tggagaggga ggatgctgtc     540
acgtattcga ggggcttttc caaagagcct atttttgttt ctggagctga tcaggagtgg     600
aagtcgtgtt cggttggatg taaatttggg tttagtgggg atagaaagcc agatgccgca     660
tttgggttac ctcaaccaag tggaacagct agcattctgc gatcaatgga atcagcagaa     720
tactatgctg agaacaatat tgccatggca agacggaggg gatataacat cgtaatgaca     780
accagtctat cttcggatgt tcctgttgga tattttcat gggctgagta tgatatgatg     840
gcaccagtgc agccgaaaac tgaagctgct cttgcagctg cttcatttc caattgtggt     900
gctcgaaatt tccggttgca agctcttgag gcccttgaaa aatcaaacat caaaattgat     960
tcttatggtg gttgtcacag gaaccgtgat ggaagagtga acaaagtgga agccctgaag    1020
cactacaaat ttagcttagc gtttgaaaat tcgaatgagg aagattatgt aactgaaaaa    1080
ttcttccaat cccttgttgc tggaactgtc cctgtggttg ttggtgctcc aaatattcag    1140
gactttgctc cttctcctgg ttcaattta catattaaag agatagagga tgttgagtct    1200
gttgcaaaga ccatgagata tctagcagaa atcccgaag catataatca atcattgagg    1260
tggaagtatg agggtccatc tgactccttc aaggcccttg tggatatggc agctgtgcat    1320
tcatcgtgcc gtcttgcat tcacttggcc acagtgagta gagagaagga agaaaataat    1380
ccaagcctta agagacgtcc ttgcaagtgc actagagggc cagaaaccgt atatcatatc    1440
tatgtcagag aaagggggaag gtttgagatg gagtccattt acctgaggtc tagcaattta    1500
actctgaatg ctgtgaaggc tgctgttgtt ttgaagttca catccctgaa tcttgtgcct    1560
gtatggaaga ctgaaaggcc tgaagttata agagggggga gtgctttaaa actctacaaa    1620
atatacccaa ttggcttgac acagagacaa gctctttata ccttcagctt caaaggtgat    1680
gctgatttca ggagtcactt ggagaacaat ccttgtgcca gtttgaagt cattttgtg    1740
tagcatgcgc taaatggtac ctctgctcta cctgaattag cttcacttag ctgagcacta    1800
gctagagttt taggaatgag tatggcagtg aatatggcat ggctttattt atgcctagtt    1860
tcttggccaa ctcattgatg ttttgtataa gacatcacac tttaatttta aacttgtttc    1920
tgtagaagtg caaatccata tttaatgctt agtttagtg ctcttatctg atcatctaga    1980
agtcacagtt cttgtatatt gtgagtgaaa actgaaatct aatagaagga tcagatgttt    2040
cactcaagac acattattac ttcatgttgt tttgatgatc tcgagctttt ttagtgtctg    2100
```

```
gaactgtccc tgtggtttga gcacctgtta ttgcttcagt gttactgtcc agtggttatc    2160
gtttttgacc tctaaaaaaa aaaaaaaaaa aaaaaaaa                            2198
```

<210> SEQ ID NO 2
<211> LENGTH: 510
<212> TYPE: PRT
<213> ORGANISM: Vigna radiata

<400> SEQUENCE: 2

```
Met Met Gly Leu Leu Thr Asn Leu Arg Gly Ser Arg Thr Asp Gly Ala
1               5                   10                  15

Gln Gln Asp Ser Leu Pro Val Leu Ala Pro Gly Gly Asn Pro Lys Arg
            20                  25                  30

Lys Trp Ser Asn Leu Met Pro Leu Val Val Ala Leu Val Ile Ala
        35                  40                  45

Glu Ile Ala Phe Leu Gly Arg Leu Asp Met Ala Lys Asn Ala Ala Met
    50                  55                  60

Val Asp Ser Leu Ala Asp Phe Phe Tyr Arg Ser Arg Ala Val Val Glu
65                  70                  75                  80

Gly Asp Asp Leu Gly Leu Gly Leu Val Ala Ser Asp Arg Asn Ser Glu
                85                  90                  95

Ser Tyr Ser Cys Glu Glu Trp Leu Glu Arg Glu Asp Ala Val Thr Tyr
            100                 105                 110

Ser Arg Gly Phe Ser Lys Glu Pro Ile Phe Val Ser Gly Ala Asp Gln
        115                 120                 125

Glu Trp Lys Ser Cys Ser Val Gly Cys Lys Phe Gly Phe Ser Gly Asp
    130                 135                 140

Arg Lys Pro Asp Ala Ala Phe Gly Leu Pro Gln Pro Ser Gly Thr Ala
145                 150                 155                 160

Ser Ile Leu Arg Ser Met Glu Ser Ala Glu Tyr Tyr Ala Glu Asn Asn
                165                 170                 175

Ile Ala Met Ala Arg Arg Arg Gly Tyr Asn Ile Val Met Thr Thr Ser
            180                 185                 190

Leu Ser Ser Asp Val Pro Val Gly Tyr Phe Ser Trp Ala Glu Tyr Asp
        195                 200                 205

Met Met Ala Pro Val Gln Pro Lys Thr Glu Ala Ala Leu Ala Ala Ala
    210                 215                 220

Phe Ile Ser Asn Cys Gly Ala Arg Asn Phe Arg Leu Gln Ala Leu Glu
225                 230                 235                 240

Ala Leu Glu Lys Ser Asn Ile Lys Ile Asp Ser Tyr Gly Gly Cys His
                245                 250                 255

Arg Asn Arg Asp Gly Arg Val Asn Lys Val Glu Ala Leu Lys His Tyr
            260                 265                 270

Lys Phe Ser Leu Ala Phe Glu Asn Ser Asn Glu Glu Asp Tyr Val Thr
        275                 280                 285

Glu Lys Phe Phe Gln Ser Leu Val Ala Gly Thr Val Pro Val Val Val
    290                 295                 300

Gly Ala Pro Asn Ile Gln Asp Phe Ala Pro Ser Pro Gly Ser Ile Leu
305                 310                 315                 320

His Ile Lys Glu Ile Glu Asp Val Ser Val Ala Lys Thr Met Arg
                325                 330                 335

Tyr Leu Ala Glu Asn Pro Glu Ala Tyr Asn Gln Ser Leu Arg Trp Lys
            340                 345                 350
```

```
Tyr Glu Gly Pro Ser Asp Ser Phe Lys Ala Leu Val Asp Met Ala Ala
            355                 360                 365

Val His Ser Ser Cys Arg Leu Cys Ile His Leu Ala Thr Val Ser Arg
    370                 375                 380

Glu Lys Glu Glu Asn Asn Pro Ser Leu Lys Arg Arg Pro Cys Lys Cys
385                 390                 395                 400

Thr Arg Gly Pro Glu Thr Val Tyr His Ile Tyr Val Arg Glu Arg Gly
                405                 410                 415

Arg Phe Glu Met Glu Ser Ile Tyr Leu Arg Ser Ser Asn Leu Thr Leu
            420                 425                 430

Asn Ala Val Lys Ala Ala Val Val Leu Lys Phe Thr Ser Leu Asn Leu
    435                 440                 445

Val Pro Val Trp Lys Thr Glu Arg Pro Glu Val Ile Arg Gly Gly Ser
450                 455                 460

Ala Leu Lys Leu Tyr Lys Ile Tyr Pro Ile Gly Leu Thr Gln Arg Gln
                470                 475                 480
465

Ala Leu Tyr Thr Phe Ser Phe Lys Gly Asp Ala Asp Phe Arg Ser His
            485                 490                 495

Leu Glu Asn Asn Pro Cys Ala Lys Phe Glu Val Ile Phe Val
    500                 505                 510

<210> SEQ ID NO 3
<211> LENGTH: 105
<212> TYPE: DNA
<213> ORGANISM: Artificial Sequence
<220> FEATURE:
<223> OTHER INFORMATION: Description of Artificial Sequence:cDNA

<400> SEQUENCE: 3
gaagccctga agcactacaa atttagctta gcgtttgaaa attcgaatga ggaagattat      60
gtaactgaaa aattcttcca atcccttgtt gctggaactg tccct                    105

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence:residues 267
      to 301 of SEQ ID No 2 from Vigna radiata

<400> SEQUENCE: 4

Glu Ala Leu Lys His Tyr Lys Phe Ser Leu Ala Phe Glu Asn Ser Asn
1               5                   10                  15

Glu Glu Asp Tyr Val Thr Glu Lys Phe Phe Gln Ser Leu Val Ala Gly
            20                  25                  30

Thr Val Pro
        35

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:N-terminal
      sequence of tryptic peptide from Vigna radiata
<220> FEATURE:
<221> NAME/KEY: misc_feature
<222> LOCATION: (5)
<223> OTHER INFORMATION: unsure

<400> SEQUENCE: 5
```

Lys Pro Asp Ala Xaa Phe Gly Leu Pro Gln Pro Ser Thr Ala Ser
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence of tryptic peptide from Vigna radiata

<400> SEQUENCE: 6

Pro Glu Thr Val Tyr His Ile Tyr Val Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:N-terminal
      sequence of tryptic peptide from Vigna radiata

<400> SEQUENCE: 7

Met Glu Ser Ala Glu Tyr Tyr Ala Glu Asn Asn Ile Ala
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence of tryptic peptide from Vigna radiata

<400> SEQUENCE: 8

Gly Arg Phe Glu Met Glu Ser Ile Tyr Leu
1               5                   10

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:universal
      primer
<220> FEATURE:
<221> NAME/KEY: misc_feature
<222> LOCATION: (3),(15)
<223> OTHER INFORMATION: n is a, c, g or t

<400> SEQUENCE: 9
gcngartayt aygcngaraa yaayathgc                                      29

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:universal
      primer
<220> FEATURE:
<221> NAME/KEY: misc_feature
<222> LOCATION: (14),(17)
<223> OTHER INFORMATION: n is a, c, g or t

<400> SEQUENCE: 10
crtadatrtg rtanacngty tc                                             22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:universal
      primer
<220> FEATURE:
<221> NAME/KEY: misc_feature
<222> LOCATION: (6)
<223> OTHER INFORMATION: n is a, c, g or t

<400> SEQUENCE: 11
tadatnswyt ccatytcraa                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 12
ctggaactgt ccctgtggtt                                           20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 13
agtgcactag agggccagaa                                           20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 14
ttcgagcacc acaattggaa at                                        22

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 15
gaatgcaaag acggcacgat gaat                                      24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 16
cggcggatcc gcaattgaat gatg                                      24

<210> SEQ ID NO 17

```
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 17
ccggctgcag taccatttag cgcat                                              25

<210> SEQ ID NO 18
<211> LENGTH: 2198
<212> TYPE: DNA
<213> ORGANISM: Vigna radiata

<400> SEQUENCE: 18
actaactcaa acgctgcatt ttctttttc tttcagggaa ccatccaccc ataacaacaa          60
aaaaaacaac agcaagctgt gttttttta tcgttctttt tctttaaaca agcaccccca         120
tcatggaatc gtgctcataa cgccaaaatt ttccatttcc ctttgatttt tagtttattt        180
tgcggaattg gcagttgggg gcgcaattga atgatgggtc tgttgacgaa tcttcgaggc        240
tcgagaacag atggtgccca acaagacagc ttacccgttt tggctccggg tggcaaccca       300
aagaggaaat ggagcaatct aatgcctctt gttgttgccc ttgtggtcat cgcggagatc       360
gcgtttctgg gtaggttgga tatggccaaa aacgccgcca tggttgactc cctcgctgac      420
ttcttctacc gctctcgagc ggtcgttgaa ggtgacgatt tggggttggg tttggtggct      480
tctgatcgga attctgaatc gtatagttgt gaggaatggt tggagaggga ggatgctgtc      540
acgtattcga gggacttttc caaagagcct attttgtt ctggagctga tcaggagtgg         600
aagtcgtgtt cggttggatg taaatttggg tttagtgggg atagaaagcc agatgccgca      660
tttgggttac ctcaaccaag tggaacagct agcattctgc gttcaatgga atcagcagaa     720
tactatgctg agaacaatat tgccatggca agacggaggg gatataacat cgtaatgaca      780
accagtctat cttcggatgt tcctgttgga tatttttcat gggctgagta tgatatgatg      840
gcaccagtgc agccgaaaac tgaagctgct cttgcagctg ctttcatttc caattgtggt     900
gctcgaaatt tccggttgca agctcttgag gcccttgaaa aatcaaacat caaaattgat    960
tcttatggtg gttgtcacag gaaccgtgat ggaagagtga acaaagtgga agccctgaag   1020
cactacaaat ttagcttagc gtttgaaaat tcgaatgagg aagattatgt aactgaaaaa    1080
ttcttccaat cccttgttgc tggaactgtc cctgtggttg ttggtgctcc aaatattcag    1140
gactttgctc cttctcctgg ttcaattta catattaaag agatagagga tgttgagtct     1200
gttgcaaaga ccatgagata tctagcagaa atcccgaag catataatca atcattgagg    1260
tggaagtatg agggtccatc tgactccttc aaggcccttg tggatatggc agctgtgcat    1320
tcatcgtgcc gtcttttgcat tcacttggcc acagtgagta gagagaagga agaaaataat  1380
ccaagcctta agagacgtcc ttgcaagtgc actagagggc cagaaaccgt atatcatatc  1440
tatgtcagag aaaggggaag gtttgagatg gagtccattt acctgaggtc tagcaattta   1500
actctgaatg ctgtgaaggc tgctgttgtt ttgaagttca catccctgaa tcttgtgcct    1560
gtatggaaga ctgaaaggcc tgaagttata agaggggga gtgctttaaa actctacaaa    1620
atatacccaa ttggcttgac acagagacaa gctctttata ccttcagctt caaaggtgat  1680
gctgatttca ggagtcactt ggagaacaat cctatgccaa gtttgaagt cattttgtg     1740 tagcatgcgc taaatggtac ctctgctcta cctgaattag cttcacttag ctgagcacta   1800
gctagagttt taggaatgag tatggcagtg aatatggcat ggctttattt atgcctagtt   1860
```

```
tcttggccaa ctcattgatg ttttgtataa gacatcacac tttaatttta aacttgtttc    1920
tgtagaagtg caaatccata tttaatgctt agtttttagtg ctcttatctg atcatctaga   1980
agtcacagtt cttgtatatt gtgagtgaaa actgaaatct aatagaagga tcagatgttt    2040
cactcaagac acattattac ttcatgttgt tttgatgatc tcgagctttt ttagtgtctg    2100
gaactgtccc tgtggtttga gcacctgtta ttgcttcagt gttactgtcc agtggttatc    2160 gttttttgacc tctaaaaaaa aaaaaaaaaa aaaaaaaa                           2198
```

<210> SEQ ID NO 19
<211> LENGTH: 510
<212> TYPE: PRT
<213> ORGANISM: Vigna radiata

<400> SEQUENCE: 19

```
Met Met Gly Leu Leu Thr Asn Leu Arg Gly Ser Arg Thr Asp Gly Ala
1               5                   10                  15

Gln Gln Asp Ser Leu Pro Val Leu Ala Pro Gly Gly Asn Pro Lys Arg
            20                  25                  30

Lys Trp Ser Asn Leu Met Pro Leu Val Val Ala Leu Val Ile Ala
        35                  40                  45

Glu Ile Ala Phe Leu Gly Arg Leu Asp Met Ala Lys Asn Ala Ala Met
    50                  55                  60

Val Asp Ser Leu Ala Asp Phe Phe Tyr Arg Ser Arg Ala Val Val Glu
65                  70                  75                  80

Gly Asp Asp Leu Gly Leu Gly Leu Val Ala Ser Asp Arg Asn Ser Glu
                85                  90                  95

Ser Tyr Ser Cys Glu Glu Trp Leu Glu Arg Glu Asp Ala Val Thr Tyr
            100                 105                 110

Ser Arg Asp Phe Ser Lys Glu Pro Ile Phe Val Ser Gly Ala Asp Gln
        115                 120                 125

Glu Trp Lys Ser Cys Ser Val Gly Cys Lys Phe Gly Phe Ser Gly Asp
    130                 135                 140

Arg Lys Pro Asp Ala Ala Phe Gly Leu Pro Gln Pro Ser Gly Thr Ala
145                 150                 155                 160

Ser Ile Leu Arg Ser Met Glu Ser Ala Glu Tyr Tyr Ala Glu Asn Asn
                165                 170                 175

Ile Ala Met Ala Arg Arg Arg Gly Tyr Asn Ile Val Met Thr Thr Ser
            180                 185                 190

Leu Ser Ser Asp Val Pro Val Gly Tyr Phe Ser Trp Ala Glu Tyr Asp
        195                 200                 205

Met Met Ala Pro Val Gln Pro Lys Thr Glu Ala Ala Leu Ala Ala Ala
    210                 215                 220

Phe Ile Ser Asn Cys Gly Ala Arg Asn Phe Arg Leu Gln Ala Leu Glu
225                 230                 235                 240

Ala Leu Glu Lys Ser Asn Ile Lys Ile Asp Ser Tyr Gly Gly Cys His
                245                 250                 255

Arg Asn Arg Asp Gly Arg Val Asn Lys Val Glu Ala Leu Lys His Tyr
            260                 265                 270

Lys Phe Ser Leu Ala Phe Glu Asn Ser Asn Glu Glu Asp Tyr Val Thr
        275                 280                 285

Glu Lys Phe Phe Gln Ser Leu Val Ala Gly Thr Val Pro Val Val Val
    290                 295                 300

Gly Ala Pro Asn Ile Gln Asp Phe Ala Pro Ser Pro Gly Ser Ile Leu
```

```
             305                 310                 315                 320
His Ile Lys Glu Ile Glu Asp Val Glu Ser Val Ala Lys Thr Met Arg
                325                 330                 335
Tyr Leu Ala Glu Asn Pro Glu Ala Tyr Asn Gln Ser Leu Arg Trp Lys
                340                 345                 350
Tyr Glu Gly Pro Ser Asp Ser Phe Lys Ala Leu Val Asp Met Ala Ala
                355                 360                 365
Val His Ser Ser Cys Arg Leu Cys Ile His Leu Ala Thr Val Ser Arg
                370                 375                 380
Glu Lys Glu Glu Asn Asn Pro Ser Leu Lys Arg Arg Pro Cys Lys Cys
385                 390                 395                 400
Thr Arg Gly Pro Glu Thr Val Tyr His Ile Tyr Val Arg Glu Arg Gly
                405                 410                 415
Arg Phe Glu Met Glu Ser Ile Tyr Leu Arg Ser Ser Asn Leu Thr Leu
                420                 425                 430
Asn Ala Val Lys Ala Ala Val Val Leu Lys Phe Thr Ser Leu Asn Leu
                435                 440                 445
Val Pro Val Trp Lys Thr Glu Arg Pro Glu Val Ile Arg Gly Gly Ser
                450                 455                 460
Ala Leu Lys Leu Tyr Lys Ile Tyr Pro Ile Gly Leu Thr Gln Arg Gln
465                 470                 475                 480
Ala Leu Tyr Thr Phe Ser Phe Lys Gly Asp Ala Asp Phe Arg Ser His
                485                 490                 495
Leu Glu Asn Asn Pro Tyr Ala Lys Phe Glu Val Ile Phe Val
                500                 505                 510

<210> SEQ ID NO 20
<211> LENGTH: 3124
<212> TYPE: DNA
<213> ORGANISM: Medicago truncatula

<400> SEQUENCE: 20
atgggtctcg tttcaagaac aacaacaaca acaacccaag aaggtttacc agtttcagtt      60
tcaacaacgg ttccgaagaa gaaatggtcg aatttaatgc ctttatttgt agcacttgtg     120
gttattgcgg agatcgcgtt tttgggtagg ttggatatgg ctaagaacgc agctactgtt     180
gctgacttgt tctaccggtc acgtgcggtg gttgaaggtg atgattttgg gttagagatg     240
gttggtggtg ataagaattt ggaattagag agtgaaagtt gtgaggagtg gttggggaga     300
gaggatgctg ttccatattc aaggaacttt actaaggaac tgttttttgt ttctggagct     360
gaacaggttt atcctctttt aagattagta gttgattgct attatctttt tacataaact     420
atgtagttgt tatcttttag caaatttgtg tttggtgtct ggagctgaga agtttagttg     480
actttcactg tgattttta tgctatgtga ataattttta ttaaggatta tgatgagttt     540
gcttttcctt tttgatgaaa tttattcaca agctagttga ttaaggtact ttaagcatat     600
tcaaattcaa ccaggttaag ctgttcttaa tctgttttga ggtttatttc ctgatggtga     660
gctacagact ttgcaatcac gcgttgttta tctgcaggat ttgaacttgt atcgtatatg     720
acacacttta tctgaaaaat gttcttttta gcagccaaaa tgtggatatt tgattttca     780 gtgacaagat ttatcatggg tttttaagtg tattcacata tgtatctcct ggtatgttct     840
tatgaagtct gtgtttgttt aaagttatta gttaattcaa atgcaggaat ggaagtcatg     900
ttcagtggga tgtaaattta ggtttaatgg ggaccgaaaa cctgaagctg catttagctt     960
acctcagcaa gctggaacag caagtattct gaaatcaatg gagtcggcac aatactatgc    1020
```

-continued

```
agagaacaat attgccatgg cacgacggtg ggtaagcact tgtataaagt gttgattcat    1080
tacattggac tggatcgttt gtttcgtata tgttacttaa tattgtatga tggttttgta    1140
tggttctata gttccatgga aatgtgtggg gtaatgcaga aacttttgtg gtttaacgtg    1200
gtactatgtt ttgatttgca gcaatatctt ctctcatttt ttactggatt taaaaccagg    1260
tgtacctttc attgcgagtg ctaatcagtg catagtgctt acctctgttt ttagttttca    1320
tcaattgaac ttcgtttttc ttgttttata aggagagcat ttcttatttc aattttttca    1380
gaaagaagtg ttgataatca aactgatgtt tctatgtcat tgtctactag gagggggatat   1440
cacattgtaa tgacaaccag tctatcatcc gacgtccctg ttggatattt ttcatgggct    1500
gagtatgaca tcatggcacc gataaagcca aaaactgaaa aagctcttgc agctgctttt    1560
atttccaatt gtggtgctcg aaatttccgg ttgcaagctc tcgaagccct ggaaaaaaca    1620
aacatctcga ttgactctta tggtagttgt cataggaatc gtgatggaag agtggacaaa    1680
ctggaagccc tgacgcgcta caaatttagc ttagcatttg aaaattctaa cgaggaggat    1740
tatgtaactg aaaagttttt ccagtcgctt gttgctggaa ctatccctgt ggttgttggt    1800
cctccaaata ttcaagattt tgctccttct cctggttcat ttttatacat caaagaacta    1860
gaggatgttg agtctgttgc caagtccatg agatacctag cagaaaaccc tgaagcatat    1920
aatcaatcat tgaggtaaaa ttacatgatg aaaacaaaca agtttcttcg gttgctcttc    1980
ctttcctgca tccctctcgt attaagtcat tatgttattt atttacattg caccgaagga    2040
cttaacacca taattggatc ctagaatatt gcagtatata atctgggcat cttgagctta    2100
tttggttttt aaatgtgaat ggatttgcta tgttcttttt gtattttgta atcatgtgga    2160
tgcatgctga gttatcttat ttataggtgg aagtatgaag ggccatctga ttccttcaag    2220
gcccttgtgg atatggcagc tgtacattca tcttgccgcc tttgcattca cttggcctca    2280
aagagtagag agaaggaaga gaagagccca gacttcaaga ggcgaccttg caagtgcact    2340
cgagggtcag aaaccgtata tcatatctat gtgagagaaa ggggaacatt tgagatggag    2400
tccatttact tgagtatact tattattttg atcaataaat ttgtatactt cttatcttga    2460
tcaataaatt tgtcattaaa cttgatggcg tctcttggtt tgtttggcaa tcatatgcct    2520
aagaaataaa tagtatcata tgattgtgtt tggtcagact tcagagtcag atgaccctgt    2580
ttggataaac agcttaatta agtgcttata gaataatcgc ttatcatata agtgcttttg    2640
tacagttatt cctataaaag tataaaaaat agtcatattg ttttaatata agctagatct    2700
ccctaacagt ctcaaaaagt gtttatgcca gtagataaat tgaaataagt cgatctaaac    2760
agaccctaaa tccattatgg tacctatcat tttagcttat tccttcttta ttaagaatgt    2820
gatgagataa cataatgata actcattatt ttgacacaaa tgggcaggat ctagcaattt    2880
aactctggag tccttcaaga ctgctgttct tacgaagttc acgtccctga atcatgttcc    2940
tgtatggaag cctgaaagac ctgaaattct aaaaggtggt gatgaattga aggtttacaa    3000
aatatacccct gcgggcttga cacagaggca agctctttat accttcaagt tcaacgggga   3060
tgttgatttc agaagtcact tggaaagcaa tccttgtgcc aagttcgaag tcgttttgt     3120
gtag                                                                 3124
```

<210> SEQ ID NO 21
<211> LENGTH: 504
<212> TYPE: PRT
<213> ORGANISM: Medicago truncatula

<400> SEQUENCE: 21

```
Met Gly Leu Val Ser Arg Thr Thr Thr Thr Thr Gln Glu Gly Leu
1               5                   10                  15

Pro Val Ser Val Ser Thr Thr Val Pro Lys Lys Trp Ser Asn Leu
                20                  25                  30

Met Pro Leu Phe Val Ala Leu Val Val Ile Ala Glu Ile Ala Phe Leu
            35                  40                  45

Gly Arg Leu Asp Met Ala Lys Asn Ala Ala Thr Val Ala Asp Leu Phe
    50                  55                  60

Tyr Arg Ser Arg Ala Val Val Glu Gly Asp Asp Phe Gly Leu Glu Met
65                  70                  75                  80

Val Gly Gly Asp Lys Asn Leu Glu Leu Glu Ser Glu Ser Cys Glu Glu
                85                  90                  95

Trp Leu Gly Arg Glu Asp Ala Val Pro Tyr Ser Arg Asn Phe Thr Lys
            100                 105                 110

Glu Pro Val Phe Val Ser Gly Ala Glu Gln Glu Trp Lys Ser Cys Ser
                115                 120                 125

Val Gly Cys Lys Phe Arg Phe Asn Gly Asp Arg Lys Pro Glu Ala Ala
    130                 135                 140

Phe Ser Leu Pro Gln Gln Ala Gly Thr Ala Ser Ile Leu Lys Ser Met
145                 150                 155                 160

Glu Ser Ala Gln Tyr Tyr Ala Glu Asn Asn Ile Ala Met Ala Arg Arg
                165                 170                 175

Arg Gly Tyr His Ile Val Met Thr Thr Ser Leu Ser Ser Asp Val Pro
            180                 185                 190

Val Gly Tyr Phe Ser Trp Ala Glu Tyr Asp Ile Met Ala Pro Ile Lys
    195                 200                 205

Pro Lys Thr Glu Lys Ala Leu Ala Ala Ala Phe Ile Ser Asn Cys Gly
                210                 215                 220

Ala Arg Asn Phe Arg Leu Gln Ala Leu Glu Ala Leu Glu Lys Thr Asn
225                 230                 235                 240

Ile Ser Ile Asp Ser Tyr Gly Ser Cys His Arg Asn Arg Asp Gly Arg
                245                 250                 255

Val Asp Lys Leu Glu Ala Leu Thr Arg Tyr Lys Phe Ser Leu Ala Phe
            260                 265                 270

Glu Asn Ser Asn Glu Glu Asp Tyr Val Thr Glu Lys Phe Phe Gln Ser
                275                 280                 285

Leu Val Ala Gly Thr Ile Pro Val Val Gly Pro Pro Asn Ile Gln
    290                 295                 300

Asp Phe Ala Pro Ser Pro Gly Ser Phe Leu Tyr Ile Lys Glu Leu Glu
305                 310                 315                 320

Asp Val Glu Ser Val Ala Lys Ser Met Arg Tyr Leu Ala Glu Asn Pro
                325                 330                 335

Glu Ala Tyr Asn Gln Ser Leu Arg Trp Lys Tyr Glu Gly Pro Ser Asp
            340                 345                 350

Ser Phe Lys Ala Leu Val Asp Met Ala Ala Val His Ser Ser Cys Arg
    355                 360                 365

Leu Cys Ile His Leu Ala Ser Lys Ser Arg Glu Lys Glu Glu Lys Ser
                370                 375                 380

Pro Asp Phe Lys Arg Arg Pro Cys Lys Cys Thr Arg Gly Ser Glu Thr
385                 390                 395                 400

Val Tyr His Ile Tyr Val Arg Glu Arg Gly Thr Phe Glu Met Glu Ser
                405                 410                 415
```

-continued

Ile Tyr Leu Arg Ser Ser Asn Leu Thr Leu Glu Ser Phe Lys Thr Ala
            420                 425                 430

Val Leu Thr Lys Phe Thr Ser Leu Asn His Val Pro Val Trp Lys Pro
            435                 440                 445

Glu Arg Pro Glu Ile Leu Lys Gly Gly Asp Leu Lys Val Tyr Lys
450                 455                 460

Ile Tyr Pro Ala Gly Leu Thr Gln Arg Gln Ala Leu Tyr Thr Phe Lys
465                 470                 475                 480

Phe Asn Gly Asp Val Asp Phe Arg Ser His Leu Glu Ser Asn Pro Cys
            485                 490                 495

Ala Lys Phe Glu Val Val Phe Val
            500

<210> SEQ ID NO 22
<211> LENGTH: 2027
<212> TYPE: DNA
<213> ORGANISM: Medicago sativa

<400> SEQUENCE: 22

```
acgcggggga cggaggcaca attaataaaa ccttttcaa ccgtcgactt ttctctctct     60
tcaatggaat cgtgcttgta acgcaacgca gcccatttca actacctcca caagcttcat    120
tttttccatc ttcaatccaa gttttttgggt gaaaaatag tgggaaatca aggaattgaa    180
gattggaggt agaattaatt gatgggtctc gtttcaagaa caacaacaac aacaacccaa    240
gaaggtttac cagtttcagt ttcagtttca acaacggttc cgaagaagaa atggtcgaat    300
ttaatgcctt tatttgtagc acttgtggtt attgcggaga tcgcgttttt gggtaggttg    360
gatatggcta agaacgcagc tatggttgct gacttgttct accggtcacg tgcggtggtt    420
gaaggtgatg attttgggtt agagacagtt ggtggtgata agaatttgga attagagaga    480
gaaacttgtg aggagtggtt ggagagagag gatgctgtta catattcaag gaactttaat    540
aaggaacctg tttttgtttc tggagctgaa caggaatgga agtcatgttc agtgggatgt    600
aaatttgggt ttaatgggga ccggaaacct gaggctgcat ttggcttacc tcagcaagct    660
ggaacagcaa gtgttctgag atcaatggag tcggcacaat actatgcaga gaacaatctt    720
gccatggcac gacggagggg atatcacatt gtaatgacaa ccagtctatc atctgacgtc    780
cctgttggat attttcatg ggctgagtat gacatcatgg caccgataaa gccaaaaact    840
gaaaaagctc ttgcagctgc ttttatttcc aattgtggtg ctcgaaattt ccgattgcaa    900
gctctcgaag ccctagaaaa aacaaacatc tcgatcgact cttatggtag ttgtcatagg    960
aatcgtgatg aagagtgga caaactggaa accctgacgc gctacaaatt tagcttagca   1020
tttgaaaatt ctaacgagga ggattatgta actgaaaagt ttttccagtc gcttgttgct   1080
ggaactatcc ctgtggttgt tggtcctcca aatattcaag attttgctcc ttctcctgat   1140
tcatttttat atatcaaaga actagaggat gttgagtctg ttgccaagtc catgagatac   1200
ctagcagaaa accctgaagc atataatcat tcattgaggt ggaagtatga agggccatct   1260
gattcttca aagccttgt ggatatggca gctgtacatt catcttgccg cctttgcatt   1320
cacttggcca caaagagtag agagaaggaa gagaagagcc cagacttcaa gaagcgacct   1380
tgcaagtgca ctcgagggtc agaaactgta tcatatctc atgtgagaga aaggggaaca   1440
tttgagatgg agtccattta cttgagatct agcaatttaa ctcttgagtc cttcaagact   1500
gctgttctta cgaagttcac gtccctgaat catgttcctg tatggaagcc tgaaagacct   1560
```

```
gaaattctaa aaggtggcga taaattgaag gtttacaaaa taatacctgc gggcttgaca      1620
cagaggcaag ctctttatac cttccagttc aacggggatg ttgatttcag aagtcacttg      1680
gaaagcaatc cttgtgccaa gtttgaagta atttttgtgt agcatatgtt gagctaccga      1740
caatttacat gaacacctag cattagctct ttcacttaac tgagagaatg aagttttagg      1800
aatgagtatg accatggagt cggcatggct ttgtaatgcc taccttactt tggccaactc      1860
atcggggatt tacattcaga aaatatacat gacttcaacc atacttaaac ccctttttgt      1920
aagataactg aatgttcata tttaatgttg ggttatagtg ttttacttg attatatcca       1980 gccacagtta caagttggac caaaaaaaaa aaaaaaaaa aaaaaaa                     2027
```

<210> SEQ ID NO 23
<211> LENGTH: 506
<212> TYPE: PRT
<213> ORGANISM: Medicago sativa

<400> SEQUENCE: 23

```
Met Gly Leu Val Ser Arg Thr Thr Thr Thr Thr Gln Glu Gly Leu
1               5                   10                  15

Pro Val Ser Val Ser Val Ser Thr Thr Val Pro Lys Lys Trp Ser
                20                  25                  30

Asn Leu Met Pro Leu Phe Val Ala Leu Val Val Ile Ala Glu Ile Ala
            35                  40                  45

Phe Leu Gly Arg Leu Asp Met Ala Lys Asn Ala Ala Met Val Ala Asp
        50                  55                  60

Leu Phe Tyr Arg Ser Arg Ala Val Val Glu Gly Asp Asp Phe Gly Leu
65                  70                  75                  80

Glu Thr Val Gly Gly Asp Lys Asn Leu Glu Leu Glu Arg Glu Thr Cys
                85                  90                  95

Glu Glu Trp Leu Glu Arg Glu Asp Ala Val Thr Tyr Ser Arg Asn Phe
            100                 105                 110

Asn Lys Glu Pro Val Phe Val Ser Gly Ala Glu Gln Glu Trp Lys Ser
        115                 120                 125

Cys Ser Val Gly Cys Lys Phe Gly Phe Asn Gly Asp Arg Lys Pro Glu
130                 135                 140

Ala Ala Phe Gly Leu Pro Gln Gln Ala Gly Thr Ala Ser Val Leu Arg
145                 150                 155                 160

Ser Met Glu Ser Ala Gln Tyr Tyr Ala Glu Asn Asn Leu Ala Met Ala
                165                 170                 175

Arg Arg Arg Gly Tyr His Ile Val Met Thr Thr Ser Leu Ser Ser Asp
            180                 185                 190

Val Pro Val Gly Tyr Phe Ser Trp Ala Glu Tyr Asp Ile Met Ala Pro
        195                 200                 205

Ile Lys Pro Lys Thr Glu Lys Ala Leu Ala Ala Phe Ile Ser Asn
210                 215                 220

Cys Gly Ala Arg Asn Phe Arg Leu Gln Ala Leu Glu Ala Leu Glu Lys
225                 230                 235                 240

Thr Asn Ile Ser Ile Asp Ser Tyr Gly Ser Cys His Arg Asn Arg Asp
                245                 250                 255

Gly Arg Val Asp Lys Leu Glu Thr Leu Thr Arg Tyr Lys Phe Ser Leu
            260                 265                 270

Ala Phe Glu Asn Ser Asn Glu Glu Asp Tyr Val Thr Glu Lys Phe Phe
        275                 280                 285

Gln Ser Leu Val Ala Gly Thr Ile Pro Val Val Val Gly Pro Pro Asn
```

```
                290                 295                 300

Ile Gln Asp Phe Ala Pro Ser Pro Asp Ser Phe Leu Tyr Ile Lys Glu
305                 310                 315                 320

Leu Glu Asp Val Glu Ser Val Ala Lys Ser Met Arg Tyr Leu Ala Glu
                325                 330                 335

Asn Pro Glu Ala Tyr Asn His Ser Leu Arg Trp Lys Tyr Glu Gly Pro
                340                 345                 350

Ser Asp Ser Phe Lys Ala Leu Val Asp Met Ala Ala Val His Ser Ser
                355                 360                 365

Cys Arg Leu Cys Ile His Leu Ala Thr Lys Ser Arg Glu Lys Glu Glu
                370                 375                 380

Lys Ser Pro Asp Phe Lys Arg Pro Cys Lys Cys Thr Arg Gly Ser
385                 390                 395                 400

Glu Thr Val Tyr His Ile Tyr Val Arg Glu Arg Gly Thr Phe Glu Met
                405                 410                 415

Glu Ser Ile Tyr Leu Arg Ser Ser Asn Leu Thr Leu Glu Ser Phe Lys
                420                 425                 430

Thr Ala Val Leu Thr Lys Phe Thr Ser Leu Asn His Val Pro Val Trp
                435                 440                 445

Lys Pro Glu Arg Pro Glu Ile Leu Lys Gly Gly Asp Lys Leu Lys Val
                450                 455                 460

Tyr Lys Ile Ile Pro Ala Gly Leu Thr Gln Arg Gln Ala Leu Tyr Thr
465                 470                 475                 480

Phe Gln Phe Asn Gly Asp Val Asp Phe Arg Ser His Leu Glu Ser Asn
                485                 490                 495

Pro Cys Ala Lys Phe Glu Val Ile Phe Val
                500                 505

<210> SEQ ID NO 24
<211> LENGTH: 2134
<212> TYPE: DNA
<213> ORGANISM: Medicago sativa

<400> SEQUENCE: 24 acgcggggt   cgacggaggc   acaattacta   aaaccttttt   caaccgtcga   cttttctctc     60
tcttcaatgg   aatcgtgctt   gtaacgcaac   gcagcccatt   tcaactccct   ccacaagctt    120 catttttttcc   atcttcaatc   caagtttttg   ggtgaaaaaa   tagtgggaaa   tcaaggaatt    180
gaagattgga   ggtagaatta   attgatgggt   ctcgtttcaa   gaacaacaac   aacaacccaa    240
gaaggtttac   cagtttcagt   ttcagtttca   acaacggttc   cgaagaagaa   atggtcgaat    300
ttaatgcctt   tatttgtagc   acttgtggtt   attgcggaga   tcgcgttttt   gggtaggttg    360
gatatggcta   gaacgcagc   tatggttgct   gacttgttct   accggtcacg   tgcggtggtt    420
gaaggcgatg   atttttgggtt   agagacagtt   ggtggtggta   agaatttgga   attagaggga    480
gaaacttgtg   aggagtggtt   ggagagagag   gatgctgtta   catattcaag   gaactttaat    540
aaggaacctg   ttttttgtttc   tggagctgaa   caggaatgga   agtcatgttc   agtgggatgt    600
aaatttgggt   ttaatgggga   ccggaaacct   gaggctgcat   ttggcttacc   tcagcaagct    660
ggaacagcaa   gtgttctgag   atcaatggag   tcggcacaat   actatgcaga   gaacaatctt    720
gccatggcac   gacggagggg   atatcacatt   gtaatgacaa   ccagtctatc   atctgacgtc    780
cctgttggat   attttttcatg   ggctgagtat   gacatcatgg   caccgataaa   gccaaaaact    840
gaaaaagctc   ttgcagctgc   tttatttcc   aattgtggtg   ctcgaaattt   ccgattgcaa    900
```

```
gctctcgaag ccctagaaaa aacaaacatc tcgatcgact cttatggtag ttgtcatagg    960
aatcgtgatg gaagagtgga caaactggaa accctgacgc gctacaaatt tagcttagca   1020
tttgaaaatt ctaacgagga ggattatgta actgaaaagt ttttccagtc gcttgttgct   1080
ggaactatcc ctgtggttgt tggtcctcca aatattcaag attttgctcc ttctcctgat   1140
tcatttttat atatcaaaga actagaggat gttgagtctg ttgccaagtc catgagatac   1200
ctagcagaaa accctgaagc atataatcat tcattgaggt ggaagtatga agggccatct   1260
gattctttca aagcccttgt ggatatggca gctgtacatt catcttgccg cctttgcatt   1320
cacttggcca caagagtag agagaaggaa gagaagagcc cagacttcaa gaagcgacct   1380
tgcaagtgca ctcgagggtc agaaactgta tatcatatct atgtgagaga aggggaaca    1440 tttgagatgg agtccattta cttgagatct agcaatttaa ctctggagtc cttcaagact   1500
gctgttctta cgaagttcac gtccctgaat catgttcctg tatggaagcc tgaaagacct   1560
caaattctaa aaggtggcga taaattgaag gtttacaaaa taatacctgc gggcttgaca   1620
cagaggcaag ctctttatac cttccagttc aacggggatg ttgatttcag aagtcacttg   1680
gaaagcaatc cttgtgccaa gtttgaagta attttttgtgt agcatatgtt gagctaccta   1740
caatttacat gatcacctag cattagctct ttcacttaac tgagagaatg aagttttagg   1800
aatgagtatg accatggagt cggcatggct ttgtaatgcc taccctactt tggccaactc   1860 atcgggatt tacattcaga aaatatacat gacttcaacc atactaaaac ccctttttgt   1920
aagataactg aatgttcata tttaatgttg ggttatagtg ttttacttg attatatcca    1980 gacagttaca agttggacaa caagattgtg ggtttgtact gttattttta tttttttta   2040 gcagaaacmc cttatctttt gtttcgtttg aatgtagaat gaaataaaa gaaagaaaat    2100 ataacagcaa aaaaaaaaa aaaaaaaaaa aaaa                                2134
```

<210> SEQ ID NO 25
<211> LENGTH: 505
<212> TYPE: PRT
<213> ORGANISM: Medicago sativa

<400> SEQUENCE: 25

```
Met Gly Leu Val Ser Arg Thr Thr Thr Thr Gln Glu Gly Leu Pro
1               5                   10                  15

Val Ser Val Ser Val Ser Thr Thr Val Pro Lys Lys Trp Ser Asn
                20                  25                  30

Leu Met Pro Leu Phe Val Ala Leu Val Val Ile Ala Glu Ile Ala Phe
                35                  40                  45

Leu Gly Arg Leu Asp Met Ala Lys Asn Ala Ala Met Val Ala Asp Leu
        50                  55                  60

Phe Tyr Arg Ser Arg Ala Val Val Glu Gly Asp Phe Gly Leu Glu
65                  70                  75                  80

Thr Val Gly Gly Gly Lys Asn Leu Glu Leu Glu Gly Glu Thr Cys Glu
                85                  90                  95

Glu Trp Leu Glu Arg Glu Asp Ala Val Thr Tyr Ser Arg Asn Phe Asn
                100                 105                 110

Lys Glu Pro Val Phe Val Ser Gly Ala Glu Gln Glu Trp Lys Ser Cys
            115                 120                 125

Ser Val Gly Cys Lys Phe Gly Phe Asn Gly Asp Arg Lys Pro Glu Ala
        130                 135                 140

Ala Phe Gly Leu Pro Gln Gln Ala Gly Thr Ala Ser Val Leu Arg Ser
145                 150                 155                 160
```

Met Glu Ser Ala Gln Tyr Tyr Ala Glu Asn Asn Leu Ala Met Ala Arg
                165                 170                 175

Arg Arg Gly Tyr His Ile Val Met Thr Thr Ser Leu Ser Ser Asp Val
            180                 185                 190

Pro Val Gly Tyr Phe Ser Trp Ala Glu Tyr Asp Ile Met Ala Pro Ile
        195                 200                 205

Lys Pro Lys Thr Glu Lys Ala Leu Ala Ala Phe Ile Ser Asn Cys
    210                 215                 220

Gly Ala Arg Asn Phe Arg Leu Gln Ala Leu Glu Ala Leu Glu Lys Thr
225                 230                 235                 240

Asn Ile Ser Ile Asp Ser Tyr Gly Ser Cys His Arg Asn Arg Asp Gly
                245                 250                 255

Arg Val Asp Lys Leu Glu Thr Leu Thr Arg Tyr Lys Phe Ser Leu Ala
            260                 265                 270

Phe Glu Asn Ser Asn Glu Glu Asp Tyr Val Thr Glu Lys Phe Phe Gln
        275                 280                 285

Ser Leu Val Ala Gly Thr Ile Pro Val Val Gly Pro Pro Asn Ile
    290                 295                 300

Gln Asp Phe Ala Pro Ser Pro Asp Ser Phe Leu Tyr Ile Lys Glu Leu
305                 310                 315                 320

Glu Asp Val Glu Ser Val Ala Lys Ser Met Arg Tyr Leu Ala Glu Asn
                325                 330                 335

Pro Glu Ala Tyr Asn His Ser Leu Arg Trp Lys Tyr Glu Gly Pro Ser
            340                 345                 350

Asp Ser Phe Lys Ala Leu Val Asp Met Ala Ala Val His Ser Ser Cys
        355                 360                 365

Arg Leu Cys Ile His Leu Ala Thr Lys Ser Arg Glu Lys Glu Glu Lys
    370                 375                 380

Ser Pro Asp Phe Lys Lys Arg Pro Cys Lys Cys Thr Arg Gly Ser Glu
385                 390                 395                 400

Thr Val Tyr His Ile Tyr Val Arg Glu Arg Gly Thr Phe Glu Met Glu
                405                 410                 415

Ser Ile Tyr Leu Arg Ser Ser Asn Leu Thr Leu Glu Ser Phe Lys Thr
            420                 425                 430

Ala Val Leu Thr Lys Phe Thr Ser Leu Asn His Val Pro Val Trp Lys
        435                 440                 445

Pro Glu Arg Pro Gln Ile Leu Lys Gly Gly Asp Lys Leu Lys Val Tyr
    450                 455                 460

Lys Ile Ile Pro Ala Gly Leu Thr Gln Arg Gln Ala Leu Tyr Thr Phe
465                 470                 475                 480

Gln Phe Asn Gly Asp Val Asp Phe Arg Ser His Leu Glu Ser Asn Pro
                485                 490                 495

Cys Ala Lys Phe Glu Val Ile Phe Val
            500                 505

<210> SEQ ID NO 26
<211> LENGTH: 1569
<212> TYPE: DNA
<213> ORGANISM: Populus tremula

<400> SEQUENCE: 26
atgggtgttt tgacaaatct aagaggatca agagctgcaa cagcatcaca agaaggttg      60 cctgtatcag atgggtcacc atcaaattct actcaagttt caatctttaa aatgaagtgg    120

```
tcaaatttttt tgccaattttt tgttgctctt gtggtgatag cagagatcgc ctttctgggt    180
cgtcttgata tggctaaaaa tgccgattta gttgattctt gggctgatag tttttttctac    240 aggtcaacta tatctgctga tatggtggaa agtgatgatt ttggattgga aacagtgaat    300
atggataaaa ctaatggaac ttcggagtca gatagctgtg aggagtggtt agaaaaggag    360
gatgctgtgg tttattcaag agattttgat aaagaccccg ttttggtcgc tggagcggaa    420
aaggagtgga acacatgtgg ggtggaatgt cagtttggat ttaacccag taagaagcca    480 gatgctggat ttggcttacc tcaacaaggt ggaacagcta gtgtgttaag gtcgatggaa    540
tcagcttcct actatgcaga gaacaatatt gctcacgcac gacggggata tgatgttgta    600
atgacaacga gtctctcctc agatgtgcca gttggatatt tttcctgggc tgagtatgat    660
atcatggcac cagtgcagcc aaagactgag aaagcacttg ctgctgcttt catttccaat    720
tgtggtgctc gcaacttccg cttgcaagca cttgatggac ttgaaaggtt gaacatcaac    780
atagattcct atggtaactg ccatcggaac catgacggaa gagtggataa agtaaagact    840
ctgaagcgtt acaaatttag cttggctttt gagaattcca atgaggagga ttatgtcaca    900
gaaaaattct tccaatctct tgttgctgga accatacctg tggtagttgg tgctccaaat    960
attcaagatt ttgctcctgc acctaactca attttacata tcaggaagct agaagatgtt   1020
gattcaattg cgaagactat gaaataccct ggagaaaatc ctgatgccta caatcaatca   1080
ttaaggtgga aatacgaggg cccatctgat tctttcaagg cactggtaga tatggcagca   1140
gtacactcat catgccgtct ttgcattcac cttgctacta tgattcggga aaagaggaa    1200 aatagcccag ggtttaagag gcgtccctgc agatgcacca aagacttaga gaccgtgtat   1260
catttatatg taagagagag aggaagattt cagatggagt ccattttctt gaggtctggc   1320
aatctaactg taaatgctct agaggctgca gtgctcaaga gtttaagtc tttgaagcat   1380 gtgcccatct ggaagcagga aagacctgaa agcataaggg gaggagacga ttttaaagtt   1440
tacagagtat accctgtagg catgacacag aggcaagctc tgtactctta caaattcaac   1500
actgatgatg atttcaagaa tcacttggaa gtcaacccat gtgcaaagtt tgaggtgata   1560
tttgtctag                                                            1569
```

<210> SEQ ID NO 27
<211> LENGTH: 522
<212> TYPE: PRT
<213> ORGANISM: Populus tremula

<400> SEQUENCE: 27

Met Gly Val Leu Thr Asn Leu Arg Gly Ser Arg Ala Ala Thr Ala Ser
1               5                   10                  15

Gln Glu Gly Leu Pro Val Ser Asp Gly Ser Pro Ser Asn Ser Thr Gln
            20                  25                  30

Val Ser Ile Phe Lys Met Lys Trp Ser Asn Phe Leu Pro Ile Phe Val
        35                  40                  45

Ala Leu Val Val Ile Ala Glu Ile Ala Phe Leu Gly Arg Leu Asp Met
    50                  55                  60

Ala Lys Asn Ala Asp Leu Val Asp Ser Trp Ala Asp Ser Phe Phe Tyr
65                  70                  75                  80

Arg Ser Thr Ile Ser Ala Asp Met Val Glu Ser Asp Asp Phe Gly Leu
                85                  90                  95

Glu Thr Val Asn Met Asp Lys Thr Asn Gly Thr Ser Glu Ser Asp Ser
            100                 105                 110

-continued

```
Cys Glu Glu Trp Leu Glu Lys Glu Asp Ala Val Val Tyr Ser Arg Asp
            115                 120                 125

Phe Asp Lys Asp Pro Val Leu Val Ala Gly Ala Glu Lys Glu Trp Asn
130                 135                 140

Thr Cys Gly Val Glu Cys Gln Phe Gly Phe Asn Pro Ser Lys Lys Pro
145                 150                 155                 160

Asp Ala Gly Phe Gly Leu Pro Gln Gln Gly Thr Ala Ser Val Leu
                165                 170                 175

Arg Ser Met Glu Ser Ala Ser Tyr Tyr Ala Glu Asn Asn Ile Ala His
            180                 185                 190

Ala Arg Arg Gly Tyr Asp Val Val Met Thr Thr Ser Leu Ser Ser Asp
        195                 200                 205

Val Pro Val Gly Tyr Phe Ser Trp Ala Glu Tyr Asp Ile Met Ala Pro
    210                 215                 220

Val Gln Pro Lys Thr Glu Lys Ala Leu Ala Ala Ala Phe Ile Ser Asn
225                 230                 235                 240

Cys Gly Ala Arg Asn Phe Arg Leu Gln Ala Leu Asp Gly Leu Glu Arg
                245                 250                 255

Leu Asn Ile Asn Ile Asp Ser Tyr Gly Asn Cys His Arg Asn His Asp
            260                 265                 270

Gly Arg Val Asp Lys Val Lys Thr Leu Lys Arg Tyr Lys Phe Ser Leu
        275                 280                 285

Ala Phe Glu Asn Ser Asn Glu Glu Asp Tyr Val Thr Glu Lys Phe Phe
    290                 295                 300

Gln Ser Leu Val Ala Gly Thr Ile Pro Val Val Gly Ala Pro Asn
305                 310                 315                 320

Ile Gln Asp Phe Ala Pro Ala Pro Asn Ser Ile Leu His Ile Arg Lys
                325                 330                 335

Leu Glu Asp Val Asp Ser Ile Ala Lys Thr Met Lys Tyr Leu Gly Glu
            340                 345                 350

Asn Pro Asp Ala Tyr Asn Gln Ser Leu Arg Trp Lys Tyr Glu Gly Pro
        355                 360                 365

Ser Asp Ser Phe Lys Ala Leu Val Asp Met Ala Ala Val His Ser Ser
    370                 375                 380

Cys Arg Leu Cys Ile His Leu Ala Thr Met Ile Arg Glu Lys Glu Glu
385                 390                 395                 400

Asn Ser Pro Gly Phe Lys Arg Arg Pro Cys Arg Cys Thr Lys Asp Leu
                405                 410                 415

Glu Thr Val Tyr His Leu Tyr Val Arg Glu Arg Gly Arg Phe Gln Met
            420                 425                 430

Glu Ser Ile Phe Leu Arg Ser Gly Asn Leu Thr Val Asn Ala Leu Glu
        435                 440                 445

Ala Ala Val Leu Lys Lys Phe Lys Ser Leu Lys His Val Pro Ile Trp
    450                 455                 460

Lys Gln Glu Arg Pro Glu Ser Ile Arg Gly Gly Asp Phe Lys Val
465                 470                 475                 480

Tyr Arg Val Tyr Pro Val Gly Met Thr Gln Arg Gln Ala Leu Tyr Ser
                485                 490                 495

Tyr Lys Phe Asn Thr Asp Asp Phe Lys Asn His Leu Glu Val Asn
            500                 505                 510

Pro Cys Ala Lys Phe Glu Val Ile Phe Val
        515                 520
```

```
<210> SEQ ID NO 28
<211> LENGTH: 1729
<212> TYPE: DNA
<213> ORGANISM: Arabidopsis thaliana

<400> SEQUENCE: 28
gctttctcat caatcaaagt atcaaacgat aaaaacccaa atcacaattc ttaaaatcca      60
ttcattattg ataaaaaatc gtcgctttga taatgggtgt tttctccaat cttcgaggtc     120
ctaaaattgg attgacccat gaagaattgc ctgtagtagc caatggctct acttcttctt     180
cttcgtctcc ttcctctttc aagcgtaaag tctcgacctt tttgccaatc tgcgtggctc     240
ttgtcgtcat tatcgagatc gggttcctct gtcggctcga taacgcttct ttggtcgata     300
cgttaaccca ttttttcacc aagtcgtcgt ccgatttgaa agttgggtca ggaatagaga     360
aatgccagga gtggttagag agagtggatt cagttactta ttctagagat ttcactaaag     420
atccgatttt tatctctggt agtaacaagg acttcaaatc gtgctctgtt gattgtgtaa     480
tgggattcac ttcagataag aaacctgatg cggcttttgg attaagtcat caacctggaa     540
cactcagtat aatccgttcc atggaatcag cacagtatta ccaagagaat aatcttgctc     600
aagcacgacg gaaaggttat gatattgtga tgacaactag tctgtcatca gatgttcctg     660
ttgggtattt ttcatgggcg gaatatgata ttatggctcc agtgcaacca aaaacagaga     720
aagctcttgc tgctgctttt atttccaatt gcgccgctcg gaatttccgc ctgcaagctc     780
ttgaagcctt aatgaagacg aatgttaaga ttgattctta tggtggttgt caccggaatc     840
gggatgggag tgtggagaag gttgaagctc ttaagcacta caaattcagt ctagcttttg     900
agaacaccaa cgaggaggat tatgtcacag agaagttctt ccaatctcta gtcgctggat     960
ctgtccctgt ggttgttgga gctccaaata tagaagaatt tgcaccttct cctgactcat    1020
tccttcacat taagcagatg gatgatgtca aggcagttgc aaagaaaatg aagtatcttg    1080
cggataaccc tgacgcctat aatcagacgc taagatggaa acatgaaggc ccttcagatt    1140
cttttaaggc acttattgat atggctgctg tacactcttc ttgtcgtctc tgcatctttg    1200
tggctacaag gattcgtgag caagaagaga gagccctga gtttaagaga cgaccctgca    1260
aatgcaccag aggctcagag acagtttatc atttgtatgt tagagaaaga ggacggtttg    1320
acatggaatc catcttcttg aaggatggaa atctgactct ggaagctctg aatctgcgg    1380 ttcttgcgaa gttcatgtct ctgagatatg aaccaatatg gaagaggaa agacccgcga    1440 gcttaagagg agacggcaag cttagagtac atgggatata tcctattggt ctgactcaaa    1500
gacaagctct ttacaacttc aaattcgaag gaaattcaag tctcagtact cacatacaga    1560
gaaacccttg tcccaaattc gaagttgtct ttgtctaaat tctagaagaa accaaagtt     1620 tattttgtga tacatgcttt gagtgtagtt tgtcttaggc aggaattaag gaatgtgtac    1680
atataaaaat aaaagagttt ttgcttgtct aaaaaaaaaa aaaaaaaa                 1729

<210> SEQ ID NO 29
<211> LENGTH: 501
<212> TYPE: PRT
<213> ORGANISM: Arabidopsis thaliana

<400> SEQUENCE: 29

Met Gly Val Phe Ser Asn Leu Arg Gly Pro Lys Ile Gly Leu Thr His
1               5                   10                  15

Glu Glu Leu Pro Val Val Ala Asn Gly Ser Thr Ser Ser Ser Ser Ser
            20                  25                  30
```

```
Pro Ser Ser Phe Lys Arg Lys Val Ser Thr Phe Leu Pro Ile Cys Val
        35                  40                  45

Ala Leu Val Val Ile Ile Glu Ile Gly Phe Leu Cys Arg Leu Asp Asn
 50                  55                  60

Ala Ser Leu Val Asp Thr Leu Thr His Phe Phe Thr Lys Ser Ser Ser
 65                  70                  75                  80

Asp Leu Lys Val Gly Ser Gly Ile Glu Lys Cys Gln Glu Trp Leu Glu
                85                  90                  95

Arg Val Asp Ser Val Thr Tyr Ser Arg Asp Phe Thr Lys Asp Pro Ile
                100                 105                 110

Phe Ile Ser Gly Ser Asn Lys Asp Phe Lys Ser Cys Ser Val Asp Cys
            115                 120                 125

Val Met Gly Phe Thr Ser Asp Lys Lys Pro Asp Ala Ala Phe Gly Leu
    130                 135                 140

Ser His Gln Pro Gly Thr Leu Ser Ile Ile Arg Ser Met Glu Ser Ala
145                 150                 155                 160

Gln Tyr Tyr Gln Glu Asn Asn Leu Ala Gln Ala Arg Arg Lys Gly Tyr
                165                 170                 175

Asp Ile Val Met Thr Thr Ser Leu Ser Ser Asp Val Pro Val Gly Tyr
                180                 185                 190

Phe Ser Trp Ala Glu Tyr Asp Ile Met Ala Pro Val Gln Pro Lys Thr
            195                 200                 205

Glu Lys Ala Leu Ala Ala Ala Phe Ile Ser Asn Cys Ala Ala Arg Asn
    210                 215                 220

Phe Arg Leu Gln Ala Leu Glu Ala Leu Met Lys Thr Asn Val Lys Ile
225                 230                 235                 240

Asp Ser Tyr Gly Gly Cys His Arg Asn Arg Asp Gly Ser Val Glu Lys
                245                 250                 255

Val Glu Ala Leu Lys His Tyr Lys Phe Ser Leu Ala Phe Glu Asn Thr
                260                 265                 270

Asn Glu Glu Asp Tyr Val Thr Glu Lys Phe Phe Gln Ser Leu Val Ala
            275                 280                 285

Gly Ser Val Pro Val Val Gly Ala Pro Asn Ile Glu Glu Phe Ala
    290                 295                 300

Pro Ser Pro Asp Ser Phe Leu His Ile Lys Gln Met Asp Asp Val Lys
305                 310                 315                 320

Ala Val Ala Lys Lys Met Lys Tyr Leu Ala Asp Asn Pro Asp Ala Tyr
                325                 330                 335

Asn Gln Thr Leu Arg Trp Lys His Glu Gly Pro Ser Asp Ser Phe Lys
            340                 345                 350

Ala Leu Ile Asp Met Ala Ala Val His Ser Ser Cys Arg Leu Cys Ile
                355                 360                 365

Phe Val Ala Thr Arg Ile Arg Glu Gln Glu Glu Lys Ser Pro Glu Phe
    370                 375                 380

Lys Arg Arg Pro Cys Lys Cys Thr Arg Gly Ser Glu Thr Val Tyr His
385                 390                 395                 400

Leu Tyr Val Arg Glu Arg Gly Arg Phe Asp Met Glu Ser Ile Phe Leu
                405                 410                 415

Lys Asp Gly Asn Leu Thr Leu Glu Ala Leu Glu Ser Ala Val Leu Ala
            420                 425                 430

Lys Phe Met Ser Leu Arg Tyr Glu Pro Ile Trp Lys Lys Glu Arg Pro
    435                 440                 445

Ala Ser Leu Arg Gly Asp Gly Lys Leu Arg Val His Gly Ile Tyr Pro
```

```
                450              455              460
Ile Gly Leu Thr Gln Arg Gln Ala Leu Tyr Asn Phe Lys Phe Glu Gly
465                 470              475              480

Asn Ser Ser Leu Ser Thr His Ile Gln Arg Asn Pro Cys Pro Lys Phe
                485              490              495

Glu Val Val Phe Val
            500

<210> SEQ ID NO 30
<211> LENGTH: 1938
<212> TYPE: DNA
<213> ORGANISM: Arabidopsis thaliana

<400> SEQUENCE: 30
aaaacttaat aaagcctcgt actgagagat caaaacaaaa caaaacaaaa cccaaacact      60
taccaaatca atcaattatc gagaatcttc cttcctttaa tcctcaaaaa aaacaaaaac     120
ctttcttcac ctcctttcct tgattcatcc tctaggttaa tgggtgtttt ctcgaatctt     180
cgaggaccca gagccggagc tacccacgat gaatttccgg cgaccaatgg ctctccttcg     240
tcttcttctt ctccatcttc atcaatcaag cgaaaattat cgaatttgtt accactctgc     300
gttgctctgg tagttatcgc tgagatcggg tttctgggtc ggctcgataa agtcgctttg     360
gttgatacgt tgactgattt cttcacccag tctccgtcac tctcgcagtc tccaccggcg     420
agatccgatc ggaagaagat cggattattt actgatagga gctgcgagga gtggttgatg     480
agagaagatt cagttactta ctctagagat tttactaaag atccaatttt tatctctggt     540
ggtgaaaagg actttcaatg tgttctgtg gattgtacat ttggagatag ttcagggaaa     600
acaccagatg ctgcgtttgg attaggtcag aaacctggaa ctcttagtat aatacgttcc     660
atggaatcag cacagtatta tccagaaaat gatcttgcac aggcacgacg agagggttat     720
gatatagtga tgaccactag tctatcatca gatgttcctg ttggatattt ttcgtgggcg     780
gagtatgata ttatgtctcc ggtacagcca aaaactgaga gagctattgc agctgctttt     840
atttctaatt gtggtgctcg gaattttcgt ctacaagcac ttgaggcatt gatgaaaact     900
aacattaaga ttgattctta tggtggttgt catcgaaacc gggatgggaa agttgacaag     960
gttgaagctc ttaagcgata caaattcagt ttggcttttg agaatactaa cgaggaagat    1020
tatgtcaccg agaagttctt tcaatcctta gttgctgggt ccgtccccgt ggtagttggt    1080
cctccaaata tagaagaatt tgcgcctgct tcggactcat tccttcacat taagactatg    1140
gaagatgtag agccagttgc aaagagaatg aagtatctcg cagctaaccc tgctgcttat    1200
aatcagacac taagatggaa atacgagggt ccttcagatt ctttcaaggc acttgttgat    1260
atggctgctg tacactcttc ttgccgtctc tgcattttcc tggccacgag ggtccgagaa    1320
caagaagagg aaagccctaa tttcaagaaa cgaccgtgca atgtagcag gggaggatca    1380 gacacagttt atcatgtttt tgttagagaa agaggccggt ttgaaatgga atcagtcttt    1440
ttgaggggta aaagtgtgac tcaggaagct ctagaatctg cagttctcgc caagttcaag    1500
tctttaaaac atgaggcagt gtggaagaag gaaaggcctg gaaacttaaa aggagacaaa    1560
gagcttaaaa tacatcggat ttacccgctt ggcctaacgc aacgacaggc tttgtacaac    1620
ttcaaattcg agggaaattc gagtctaagt agtcacattc aaaacaaccc ttgtgctaaa    1680
tttgaggttg tcttcgtcta gtttcattcc tctggatctg tcacaggtat catctcagct    1740
aagaagacat ttctctgtgc tagaatcgca aagtgctaaa caaaccgatt agatgaaaca    1800
```

```
aaaggttaat agtcatgaga ttggtgaact cattttgttt aggcagtgta tctgtaaatc    1860
gttctgacat tgcagacgat gtgttcttga tagctggatg cataaatgtt tgaagattta    1920
gagcaatttg atagtttt                                                  1938
```

```
<210> SEQ ID NO 31
<211> LENGTH: 513
<212> TYPE: PRT
<213> ORGANISM: Arabidopsis thaliana

<400> SEQUENCE: 31
```

| | | | | | | | | | | | | | | |
|---|---|---|---|---|---|---|---|---|---|---|---|---|---|---|
| Met | Gly | Val | Phe | Ser | Asn | Leu | Arg | Gly | Pro | Arg | Ala | Gly | Ala | Thr | His |
| 1 | | | | 5 | | | | | 10 | | | | | 15 | |
| Asp | Glu | Phe | Pro | Ala | Thr | Asn | Gly | Ser | Pro | Ser | Ser | Ser | Ser | Ser | Pro |
| | | | 20 | | | | | 25 | | | | | 30 | | |
| Ser | Ser | Ser | Ile | Lys | Arg | Lys | Leu | Ser | Asn | Leu | Leu | Pro | Leu | Cys | Val |
| | | 35 | | | | | 40 | | | | | 45 | | | |
| Ala | Leu | Val | Val | Ile | Ala | Glu | Ile | Gly | Phe | Leu | Gly | Arg | Leu | Asp | Lys |
| 50 | | | | | 55 | | | | | 60 | | | | | |
| Val | Ala | Leu | Val | Asp | Thr | Leu | Thr | Asp | Phe | Phe | Thr | Gln | Ser | Pro | Ser |
| 65 | | | | | 70 | | | | | 75 | | | | | 80 |
| Leu | Ser | Gln | Ser | Pro | Pro | Ala | Arg | Ser | Asp | Arg | Lys | Lys | Ile | Gly | Leu |
| | | | | 85 | | | | | 90 | | | | | 95 | |
| Phe | Thr | Asp | Arg | Ser | Cys | Glu | Glu | Trp | Leu | Met | Arg | Glu | Asp | Ser | Val |
| | | | 100 | | | | | 105 | | | | | 110 | | |
| Thr | Tyr | Ser | Arg | Asp | Phe | Thr | Lys | Asp | Pro | Ile | Phe | Ile | Ser | Gly | Gly |
| | | 115 | | | | | 120 | | | | | 125 | | | |
| Glu | Lys | Asp | Phe | Gln | Trp | Cys | Ser | Val | Asp | Cys | Thr | Phe | Gly | Asp | Ser |
| 130 | | | | | 135 | | | | | 140 | | | | | |
| Ser | Gly | Lys | Thr | Pro | Asp | Ala | Ala | Phe | Gly | Leu | Gly | Gln | Lys | Pro | Gly |
| 145 | | | | | 150 | | | | | 155 | | | | | 160 |
| Thr | Leu | Ser | Ile | Ile | Arg | Ser | Met | Glu | Ser | Ala | Gln | Tyr | Tyr | Pro | Glu |
| | | | | 165 | | | | | 170 | | | | | 175 | |
| Asn | Asp | Leu | Ala | Gln | Ala | Arg | Arg | Gly | Tyr | Asp | Ile | Val | Met | Thr | |
| | | | 180 | | | | | 185 | | | | | 190 | | |
| Thr | Ser | Leu | Ser | Ser | Asp | Val | Pro | Val | Gly | Tyr | Phe | Ser | Trp | Ala | Glu |
| | | 195 | | | | | 200 | | | | | 205 | | | |
| Tyr | Asp | Ile | Met | Ser | Pro | Val | Gln | Pro | Lys | Thr | Glu | Arg | Ala | Ile | Ala |
| 210 | | | | | 215 | | | | | 220 | | | | | |
| Ala | Ala | Phe | Ile | Ser | Asn | Cys | Gly | Ala | Arg | Asn | Phe | Arg | Leu | Gln | Ala |
| 225 | | | | | 230 | | | | | 235 | | | | | 240 |
| Leu | Glu | Ala | Leu | Met | Lys | Thr | Asn | Ile | Lys | Ile | Asp | Ser | Tyr | Gly | Gly |
| | | | | 245 | | | | | 250 | | | | | 255 | |
| Cys | His | Arg | Asn | Arg | Asp | Gly | Lys | Val | Asp | Lys | Val | Glu | Ala | Leu | Lys |
| | | | 260 | | | | | 265 | | | | | 270 | | |
| Arg | Tyr | Lys | Phe | Ser | Leu | Ala | Phe | Glu | Asn | Thr | Asn | Glu | Glu | Asp | Tyr |
| | | 275 | | | | | 280 | | | | | 285 | | | |
| Val | Thr | Glu | Lys | Phe | Phe | Gln | Ser | Leu | Val | Ala | Gly | Ser | Val | Pro | Val |
| 290 | | | | | 295 | | | | | 300 | | | | | |
| Val | Val | Gly | Pro | Pro | Asn | Ile | Glu | Glu | Phe | Ala | Pro | Ala | Ser | Asp | Ser |
| 305 | | | | | 310 | | | | | 315 | | | | | 320 |
| Phe | Leu | His | Ile | Lys | Thr | Met | Glu | Asp | Val | Glu | Pro | Val | Ala | Lys | Arg |
| | | | | 325 | | | | | 330 | | | | | 335 | |
| Met | Lys | Tyr | Leu | Ala | Ala | Asn | Pro | Ala | Ala | Tyr | Asn | Gln | Thr | Leu | Arg |
| | | | 340 | | | | | 345 | | | | | 350 | | |

```
Trp Lys Tyr Glu Gly Pro Ser Asp Ser Phe Lys Ala Leu Val Asp Met
    355                 360                 365

Ala Ala Val His Ser Ser Cys Arg Leu Cys Ile Phe Leu Ala Thr Arg
    370                 375                 380

Val Arg Glu Gln Glu Glu Ser Pro Asn Phe Lys Lys Arg Pro Cys
385                 390                 395                 400

Lys Cys Ser Arg Gly Gly Ser Asp Thr Val Tyr His Val Phe Val Arg
                405                 410                 415

Glu Arg Gly Arg Phe Glu Met Glu Ser Val Phe Leu Arg Gly Lys Ser
                420                 425                 430

Val Thr Gln Glu Ala Leu Glu Ser Ala Val Leu Ala Lys Phe Lys Ser
                435                 440                 445

Leu Lys His Glu Ala Val Trp Lys Lys Glu Arg Pro Gly Asn Leu Lys
    450                 455                 460

Gly Asp Lys Glu Leu Lys Ile His Arg Ile Tyr Pro Leu Gly Leu Thr
465                 470                 475                 480

Gln Arg Gln Ala Leu Tyr Asn Phe Lys Phe Glu Gly Asn Ser Ser Leu
                485                 490                 495

Ser Ser His Ile Gln Asn Asn Pro Cys Ala Lys Phe Glu Val Val Phe
                500                 505                 510

Val

<210> SEQ ID NO 32
<211> LENGTH: 1736
<212> TYPE: DNA
<213> ORGANISM: Arabidopsis thaliana

<400> SEQUENCE: 32
aaatcgtcgc tttgataatg ggtgttttct ccaatcttcg aggtcctaaa attggattga      60
cccatgaaga attgcctgta gtagccaatg gctctacttc ttcttcttcg tctccttcct     120
ctttcaagcg taaagtctcg accttttgc caatctgcgt ggctcttgtc gtcattatcg      180
agatcgggtt cctctgtcgg ctcgataacg cttctttggt cgatacgtta acccattttt     240
tcaccaagtc gtcgtccgat ttgaaagttg ggtccggaat agagagatgc caggagtggt     300
tagagagagt ggattcagtt acttattcta gagatttcac taaagatccg atttttatct     360
ctggtagtaa caaggacttc aaatcgtgct ctgttgattg tgtaatggga ttcacttcag     420
ataagaaacc tgatgcggct tttggattaa gtcatcaacc tggaacactc agtataatcc     480
gttccatgga atcagcacag tattaccaag agaataatct tgctcaagca cgacggaaag     540
gttatgatat tgtgatgaca actagtctgt catcaggtgt tcctgttgag tattttttcat    600 gggcggaata tgatattatg gctccagtgc aaccaaaaac agagaaagct cttgctgctg     660
cttttatttc caattgcgcc gctcggaatt ccgcctgca agctcttgaa gccttaatga      720
agacgaatgt taagattgat tcttatggtg gttgtcaccg gaatcgggat gggagtgtgg     780
agaaggttga agctcttaag cactacaaat tcagtctagc ttttgagaac accaacgagg     840
aggattatgt cacagagaag ttcttccaat ctctagtcgc tggatctgtc cctgtggttg     900
ttggagctcc aaatatagaa gaatttgcac cttctcctga ctcattcctt cacattaagc     960
agatggatga tgtcaaggca gttgcaaaga aaatgaagta tcttgcggat aaccctgacg    1020
cctataatca gacgctaaga tggaaacatg aaggcccttc agattctttt aaggcactta    1080
ttgatatggc tgctgtacac tcttcttgtc gtctctgcat ctttgtggct acaaggattc    1140
```

```
gtgagcaaga agagaagagc cctgagttta agagacgacc ctgcaaacgc accagaggct      1200
cagagacagt ttatcatttg tatgttagag aaagaggacg gtttgacatg gaatccatct      1260
tcttgaagga tggaaatctg actctggaag ctctggaatc tgcggttctt gcgaagttca      1320
tgtctctgag atatgaacca atatggaaga aggaaagacc cgcgagctta agaggagacg      1380
gcaagcttag agtacatggg atatatccta ttggtctgac tcaaagacaa gctcttttaca     1440 acttcaaatt cgaaggaaat tcaagtctca gtactcacat acagaaaac ccttgtccca       1500 aattcgaagt tgtctttgtc taaattctag aagaaaacca aagtttattt tgtgatacat      1560
gctttgagtg tagtttgtct taggcaggaa ttaaggaatg tgtacatata aaaataaaag      1620 agttttttgct tgtcttattg ggtactacaa tgcacatatg ttcaagtgta gtttgataaa     1680
acacaaaatg acacaagcat tctcagatta gctttaacag atttacagat actgca          1736
```

<210> SEQ ID NO 33
<211> LENGTH: 501
<212> TYPE: PRT
<213> ORGANISM: Arabidopsis thaliana

<400> SEQUENCE: 33

```
Met Gly Val Phe Ser Asn Leu Arg Gly Pro Lys Ile Gly Leu Thr His
1               5                   10                  15

Glu Glu Leu Pro Val Val Ala Asn Gly Ser Thr Ser Ser Ser Ser Ser
            20                  25                  30

Pro Ser Ser Phe Lys Arg Lys Val Ser Thr Phe Leu Pro Ile Cys Val
        35                  40                  45

Ala Leu Val Val Ile Ile Glu Ile Gly Phe Leu Cys Arg Leu Asp Asn
    50                  55                  60

Ala Ser Leu Val Asp Thr Leu Thr His Phe Phe Thr Lys Ser Ser Ser
65                  70                  75                  80

Asp Leu Lys Val Gly Ser Gly Ile Glu Arg Cys Gln Glu Trp Leu Glu
                85                  90                  95

Arg Val Asp Ser Val Thr Tyr Ser Arg Asp Phe Thr Lys Asp Pro Ile
            100                 105                 110

Phe Ile Ser Gly Ser Asn Lys Asp Phe Lys Ser Cys Ser Val Asp Cys
        115                 120                 125

Val Met Gly Phe Thr Ser Asp Lys Lys Pro Asp Ala Ala Phe Gly Leu
    130                 135                 140

Ser His Gln Pro Gly Thr Leu Ser Ile Ile Arg Ser Met Glu Ser Ala
145                 150                 155                 160

Gln Tyr Tyr Gln Glu Asn Asn Leu Ala Gln Ala Arg Arg Lys Gly Tyr
                165                 170                 175

Asp Ile Val Met Thr Thr Ser Leu Ser Ser Gly Val Pro Val Glu Tyr
            180                 185                 190

Phe Ser Trp Ala Glu Tyr Asp Ile Met Ala Pro Val Gln Pro Lys Thr
        195                 200                 205

Glu Lys Ala Leu Ala Ala Phe Ile Ser Asn Cys Ala Ala Arg Asn
    210                 215                 220

Phe Arg Leu Gln Ala Leu Glu Ala Leu Met Lys Thr Asn Val Lys Ile
225                 230                 235                 240

Asp Ser Tyr Gly Gly Cys His Arg Asn Arg Asp Gly Ser Val Glu Lys
                245                 250                 255

Val Glu Ala Leu Lys His Tyr Lys Phe Ser Leu Ala Phe Glu Asn Thr
            260                 265                 270
```

```
Asn Glu Glu Asp Tyr Val Thr Glu Lys Phe Phe Gln Ser Leu Val Ala
            275                 280                 285

Gly Ser Val Pro Val Val Gly Ala Pro Asn Ile Glu Glu Phe Ala
290                 295                 300

Pro Ser Pro Asp Ser Phe Leu His Ile Lys Gln Met Asp Asp Val Lys
305                 310                 315                 320

Ala Val Ala Lys Lys Met Lys Tyr Leu Ala Asp Asn Pro Asp Ala Tyr
                325                 330                 335

Asn Gln Thr Leu Arg Trp Lys His Glu Gly Pro Ser Asp Ser Phe Lys
            340                 345                 350

Ala Leu Ile Asp Met Ala Ala Val His Ser Ser Cys Arg Leu Cys Ile
        355                 360                 365

Phe Val Ala Thr Arg Ile Arg Glu Gln Glu Glu Lys Ser Pro Glu Phe
    370                 375                 380

Lys Arg Arg Pro Cys Lys Arg Thr Arg Gly Ser Glu Thr Val Tyr His
385                 390                 395                 400

Leu Tyr Val Arg Glu Arg Gly Arg Phe Asp Met Glu Ser Ile Phe Leu
                405                 410                 415

Lys Asp Gly Asn Leu Thr Leu Glu Ala Leu Glu Ser Ala Val Leu Ala
            420                 425                 430

Lys Phe Met Ser Leu Arg Tyr Glu Pro Ile Trp Lys Lys Glu Arg Pro
        435                 440                 445

Ala Ser Leu Arg Gly Asp Gly Lys Leu Arg Val His Gly Ile Tyr Pro
    450                 455                 460

Ile Gly Leu Thr Gln Arg Gln Ala Leu Tyr Asn Phe Lys Phe Glu Gly
465                 470                 475                 480

Asn Ser Ser Leu Ser Thr His Ile Gln Arg Asn Pro Cys Pro Lys Phe
                485                 490                 495

Glu Val Val Phe Val
            500

<210> SEQ ID NO 34
<211> LENGTH: 1607
<212> TYPE: DNA
<213> ORGANISM: Arabidopsis thaliana

<400> SEQUENCE: 34
acaaaaacct tcttcacct ccttttcttg attcatcctc taggttaatg ggtgttttct      60
cgaatcttcg aggacccaga gccggagcta cccacgatga atttccggcg accaatggct    120
ctccttcgtc ttcttcttct ccatcttcat caatcaagcg aaaattatcg aatttgttac    180
cactctgcgt tgctctggta gttatcgctg agatcgggtt tctgggtcgg ctcgataaag    240
tcgctttggt tgatacgttg actgattcct tcacccagtc tccgtcactc tcgcagtctc    300
caccggcgag atccgatcgg aagaagatcg gattatttac tgataggagc tgcgaggagt    360
ggttgatgag agaagattca gttacttact ctagagattt tactaaagat ccaatttta    420 tctctggtgg tgaaaaggac tttcaatggt gttctgtgga ttgtacattt ggagatagtt    480
cagggaaaac accagatgct gcgtttggat taggtcagaa acctggaact cttagtataa    540
tacgttccat ggaatcagca cagtattatc cagaaaatga tcttgcacag gcacgacgga    600
gaggttatga tatagtgatg accactagtc tatcatcaga tgttcctgtt ggatattttt    660
cgtgggcgga gtatgatatt atgtctccgg tacagccaaa aactgagaga gctattgcag    720
ctgcttttat ttctaattgt ggtgctcgga atttcgtct acaagcactt gaggcattga    780
```

```
tgaaaactaa cattaagatt gattcttatg gtggttgtca tcgaaaccgg gatgggaaag    840
ttgacaaggt tgaagctctt aagcgataca aattcagttt ggcttttgag aatactaacg    900
aggaagatta tgtcaccgag aagttctttc aatccttagt tgctgggtcc gtccccgtgg    960
tagttggtcc tccaaatata gaagaatttg cgcctgcttc ggacacattc cttcacatta   1020
agactatgga agatgtagag ccagttgcaa agagaatgaa gtatctcgca gctaaccctg   1080
ctgcttataa tcagacacta agatggaaat acgagggtcc ttcagattct ttcaaggcac   1140
ttgttgatat ggctgctgta cactcttctt gccgtctctg cattttcctg gccacgaggg   1200
tccgagaaca agaagaggaa agtcctaatt caagaaacg accgtgcaaa tgtagcaggg    1260
gaggatcaga cacagtttat catgtttttg ttagagaaag aggccggttt gaaatggaat   1320
cagtcttttt gagggtaaa agtgtgactc aggaagctct agaatctgca gttctcgcca    1380
agttcaagtc tttaaaacat gaggcagtgt ggaagaagga aaggcctgga aacttaaaag   1440
gagacaaaga gcttaaaata catcggattt acccgcttgg cctaacgcaa cgacaggctt   1500
tgtacaactt caaattcgag ggaaattcga gtctaagtag tcacattcaa acaacccttt   1560
gtgctaaatt tgaggttgtc ttcgtctagt ttcattcctc tggatct                 1607
```

<210> SEQ ID NO 35
<211> LENGTH: 513
<212> TYPE: PRT
<213> ORGANISM: Arabidopsis thaliana

<400> SEQUENCE: 35

```
Met Gly Val Phe Ser Asn Leu Arg Gly Pro Arg Ala Gly Ala Thr His
 1               5                  10                  15

Asp Glu Phe Pro Ala Thr Asn Gly Ser Pro Ser Ser Ser Ser Ser Pro
            20                  25                  30

Ser Ser Ser Ile Lys Arg Lys Leu Ser Asn Leu Leu Pro Leu Cys Val
        35                  40                  45

Ala Leu Val Val Ile Ala Glu Ile Gly Phe Leu Gly Arg Leu Asp Lys
    50                  55                  60

Val Ala Leu Val Asp Thr Leu Thr Asp Phe Phe Thr Gln Ser Pro Ser
65                  70                  75                  80

Leu Ser Gln Ser Pro Pro Ala Arg Ser Asp Arg Lys Lys Ile Gly Leu
                85                  90                  95

Phe Thr Asp Arg Ser Cys Glu Glu Trp Leu Met Arg Glu Asp Ser Val
            100                 105                 110

Thr Tyr Ser Arg Asp Phe Thr Lys Asp Pro Ile Phe Ile Ser Gly Gly
        115                 120                 125

Glu Lys Asp Phe Gln Trp Cys Ser Val Asp Cys Thr Phe Gly Asp Ser
    130                 135                 140

Ser Gly Lys Thr Pro Asp Ala Ala Phe Gly Leu Gly Gln Lys Pro Gly
145                 150                 155                 160

Thr Leu Ser Ile Ile Arg Ser Met Glu Ser Ala Gln Tyr Tyr Pro Glu
                165                 170                 175

Asn Asp Leu Ala Gln Ala Arg Arg Gly Tyr Asp Ile Val Met Thr
            180                 185                 190

Thr Ser Leu Ser Ser Asp Val Pro Val Gly Tyr Phe Ser Trp Ala Glu
        195                 200                 205

Tyr Asp Ile Met Ser Pro Val Gln Pro Lys Thr Glu Arg Ala Ile Ala
    210                 215                 220

Ala Ala Phe Ile Ser Asn Cys Gly Ala Arg Asn Phe Arg Leu Gln Ala
```

```
                    225                 230                 235                 240
Leu Glu Ala Leu Met Lys Thr Asn Ile Lys Ile Asp Ser Tyr Gly Gly
                        245                 250                 255

Cys His Arg Asn Arg Asp Gly Lys Val Asp Lys Val Glu Ala Leu Lys
                260                 265                 270

Arg Tyr Lys Phe Ser Leu Ala Phe Glu Asn Thr Asn Glu Glu Asp Tyr
            275                 280                 285

Val Thr Glu Lys Phe Phe Gln Ser Leu Val Ala Gly Ser Val Pro Val
        290                 295                 300

Val Val Gly Pro Pro Asn Ile Glu Glu Phe Ala Pro Ala Ser Asp Thr
305                 310                 315                 320

Phe Leu His Ile Lys Thr Met Glu Asp Val Glu Pro Val Ala Lys Arg
                    325                 330                 335

Met Lys Tyr Leu Ala Ala Asn Pro Ala Ala Tyr Asn Gln Thr Leu Arg
                340                 345                 350

Trp Lys Tyr Glu Gly Pro Ser Asp Ser Phe Lys Ala Leu Val Asp Met
            355                 360                 365

Ala Ala Val His Ser Ser Cys Arg Leu Cys Ile Phe Leu Ala Thr Arg
        370                 375                 380

Val Arg Glu Gln Glu Glu Ser Pro Asn Phe Lys Lys Arg Pro Cys
385                 390                 395                 400

Lys Cys Ser Arg Gly Gly Ser Asp Thr Val Tyr His Val Phe Val Arg
                    405                 410                 415

Glu Arg Gly Arg Phe Glu Met Glu Ser Val Phe Leu Arg Gly Lys Ser
                420                 425                 430

Val Thr Gln Glu Ala Leu Glu Ser Ala Val Leu Ala Lys Phe Lys Ser
            435                 440                 445

Leu Lys His Glu Ala Val Trp Lys Lys Glu Arg Pro Gly Asn Leu Lys
        450                 455                 460

Gly Asp Lys Glu Leu Lys Ile His Arg Ile Tyr Pro Leu Gly Leu Thr
465                 470                 475                 480

Gln Arg Gln Ala Leu Tyr Asn Phe Lys Phe Glu Gly Asn Ser Ser Leu
                    485                 490                 495

Ser Ser His Ile Gln Asn Asn Pro Cys Ala Lys Phe Glu Val Val Phe
                500                 505                 510

Val

<210> SEQ ID NO 36
<211> LENGTH: 1497
<212> TYPE: DNA
<213> ORGANISM: Zea mays

<400> SEQUENCE: 36
atgaagggct cctcccactc gcaggcgggg gcgcaggcgg tacggaggcg gcgctggggg    60
tgtcttctgc cgctcctcgt tggcgccgcc ttcctcgccg agatcgcgtt cctcggccgc   120
ctcgacatgg cgaagaacgc cgaggcggtc gagagctgga ccacctcctt ttaccgccgc   180
tccgccgatt tgggcgatgc cgttggcggg ggcgcagcct cgagggcagg cggcgacagc   240
gaggacgaag agatccggct gtgcgagcag cggctcgaga gggaggatgc cgtgccctac   300
gaccgcgact tgacagtgac tccgtgcttg tcggtggcgc tgccaaggga ttggaataaa   360
tgctacgtag atgtgaatt tggttttttct gcgagtaaga cacctgatgc tacatttgga   420
attgcaccag atccttctgt agatggtatc ctcagatcga tggaatcatc tcaatattat   480
```

```
tcagagaata atattgatgt ggctcgaggg agagggtaca agattgtgat gacaaccagc    540
ctttcttcag acgtaccagt tggctacttt tcatgggctg aatatgatat catggcacct    600
gtgcctccaa agactgaaga agctcttgct gcagccttta tttctaactg tggtgcacga    660
aactttcgtt tgcaagccct tgagatgctt gaaaacttgg atgtcaaaat agattcatat    720
ggtagttgtc atcgtaaccg tgacggcaaa gtggacaaag tggacacttt gaagcgctac    780
agattcagct tggcatttga gaattctaat gaggaggatt atgtaactga aaagttttt     840
cagtcactag tagcaggttc tattccggtt gttgttggtg ctccaaatat tcaagagttt    900
tctccgggag aaggcgcaat attacatatt aaggagcttg atgatgttgc ttcagttgct    960
aagacaatga aaaatattgc ttcaaaccct gatgccttca atcaatcttt gaggtggaag   1020
tatgatggtc catccgattc tttcaaagct cttattgaca tggcagcggt tcattcatct   1080
tgtcgtcttt gtatacatat tgctaccaag atccatttaa aggaggaaag gactccaaaa   1140
tttacaaatc gtccttgtag ctgttccacc aaaaagggaa caatttacca cttatttatc   1200
cgagagagag ggcggtttaa gtcagagagc atttacatga gatcaggcca gttaactctg   1260
ggagccttgg aatccgcagt gctcggtaaa tttaggtccc tcaaccacgt tcctgtatgg   1320
aaggatgaaa ggccaccgag cattagaggt ggggatgacc tgaaattata cagaatttac   1380
ccagtcggtc taacgcaacg tcaggctttg tacggttta gatttaggga tgattctgaa   1440
ctcgagcaat atatcaaaga ccatccctgt gcaaagcttg aagtaatttt tgtgtaa     1497
```

<210> SEQ ID NO 37
<211> LENGTH: 498
<212> TYPE: PRT
<213> ORGANISM: Zea mays

<400> SEQUENCE: 37

```
Met Lys Gly Ser Ser His Ser Gln Ala Gly Ala Gln Ala Val Arg Arg
1               5                   10                  15

Arg Arg Trp Gly Cys Leu Leu Pro Leu Val Gly Ala Ala Phe Leu
            20                  25                  30

Ala Glu Ile Ala Phe Leu Gly Arg Leu Asp Met Ala Lys Asn Ala Glu
        35                  40                  45

Ala Val Glu Ser Trp Thr Thr Ser Phe Tyr Arg Arg Ser Ala Asp Leu
    50                  55                  60

Gly Asp Ala Val Gly Gly Ala Ser Arg Ala Gly Gly Asp Ser
65                  70                  75                  80

Glu Asp Glu Glu Ile Arg Leu Cys Glu Gln Arg Leu Glu Arg Glu Asp
                85                  90                  95

Ala Val Pro Tyr Asp Arg Asp Phe Asp Ser Asp Pro Val Leu Val Gly
            100                 105                 110

Gly Ala Ala Lys Asp Trp Asn Lys Cys Tyr Val Gly Cys Glu Phe Gly
        115                 120                 125

Phe Ser Ala Ser Lys Thr Pro Asp Ala Thr Phe Gly Ile Ala Pro Asp
    130                 135                 140

Pro Ser Val Asp Gly Ile Leu Arg Ser Met Glu Ser Ser Gln Tyr Tyr
145                 150                 155                 160

Ser Glu Asn Asn Ile Asp Val Ala Arg Gly Arg Gly Tyr Lys Ile Val
                165                 170                 175

Met Thr Thr Ser Leu Ser Ser Asp Val Pro Val Gly Tyr Phe Ser Trp
            180                 185                 190

Ala Glu Tyr Asp Ile Met Ala Pro Val Pro Pro Lys Thr Glu Glu Ala
```

```
                195                 200                 205
Leu Ala Ala Ala Phe Ile Ser Asn Cys Gly Ala Arg Asn Phe Arg Leu
210                 215                 220
Gln Ala Leu Glu Met Leu Glu Asn Leu Asp Val Lys Ile Asp Ser Tyr
225                 230                 235                 240
Gly Ser Cys His Arg Asn Arg Asp Gly Lys Val Asp Lys Val Asp Thr
            245                 250                 255
Leu Lys Arg Tyr Arg Phe Ser Leu Ala Phe Glu Asn Ser Asn Glu Glu
            260                 265                 270
Asp Tyr Val Thr Glu Lys Phe Phe Gln Ser Leu Val Ala Gly Ser Ile
            275                 280                 285
Pro Val Val Gly Ala Pro Asn Ile Gln Glu Phe Ser Pro Gly Glu
290                 295                 300
Gly Ala Ile Leu His Ile Lys Glu Leu Asp Asp Val Ala Ser Val Ala
305                 310                 315                 320
Lys Thr Met Lys Asn Ile Ala Ser Asn Pro Asp Ala Phe Asn Gln Ser
                325                 330                 335
Leu Arg Trp Lys Tyr Asp Gly Pro Ser Asp Ser Phe Lys Ala Leu Ile
                340                 345                 350
Asp Met Ala Ala Val His Ser Ser Cys Arg Leu Cys Ile His Ile Ala
                355                 360                 365
Thr Lys Ile His Leu Lys Glu Glu Arg Thr Pro Lys Phe Thr Asn Arg
370                 375                 380
Pro Cys Ser Cys Ser Thr Lys Lys Gly Thr Ile Tyr His Leu Phe Ile
385                 390                 395                 400
Arg Glu Arg Gly Arg Phe Lys Ser Glu Ser Ile Tyr Met Arg Ser Gly
                405                 410                 415
Gln Leu Thr Leu Gly Ala Leu Glu Ser Ala Val Leu Gly Lys Phe Arg
                420                 425                 430
Ser Leu Asn His Val Pro Val Trp Lys Asp Glu Arg Pro Pro Ser Ile
                435                 440                 445
Arg Gly Gly Asp Asp Leu Lys Leu Tyr Arg Ile Tyr Pro Val Gly Leu
450                 455                 460
Thr Gln Arg Gln Ala Leu Tyr Gly Phe Arg Phe Arg Asp Asp Ser Glu
465                 470                 475                 480
Leu Glu Gln Tyr Ile Lys Asp His Pro Cys Ala Lys Leu Glu Val Ile
                485                 490                 495
Phe Val

<210> SEQ ID NO 38
<211> LENGTH: 1542
<212> TYPE: DNA
<213> ORGANISM: Oryza sativa

<400> SEQUENCE: 38
atgaaggggt cccactcgca gtcgcaggcc caggcccagt cccaggcggg ccggcggcgg    60
cggtgcgggt ggctgctgcc gctcctcgtc ggcgcggcct tcctcgccga gatcgcgttc   120
ctcggccgcc tcgacatggc gaagaacgcc gccgcggtcg agagctggac cacctccttc   180
tacgcccgct cctccgcccc cgcccgcgac gggaaggcag cggtcgtggt ccccggcgcg   240
gacgcggacg acgcgccccc gggcggaggt gaggtggtgg aggaggacga cggcgacatc   300
cggttgtgcg aggagcggct tgagagggag gacggcgtgc cgcacgaccg cgacttcgac   360
aaggatcccg tcctcgtcgg gggcgccgct aaggattgga ataaatgttc tgtaggatgt   420
```

-continued

```
gaatttgggt tttcagctac taagacgcct gatgctactt ttggaattgc cccagatcct    480
actgtagaga gtatcctcag atcgatggag tcatctcagt attattcaga gaacaacatt    540
gctgtggctc gagggagagg ttacaaaatt gtgatgacaa caagcctttc ctcagatgta    600
cctgttggct acttttcatg ggctgaatat gatataatgg cacctgtgcc tccaaaaact    660
gaagaagccc tagctgcagc atttatttca aactgtggtg cacgtaattt cgtttgcaa     720
gcccttgaga tgcttgagag cttagatgtc aaaattgatt catatggtag ttgccatcgt    780
aatcatgatg gcaaagttga taaagtggaa actttgaagc gctacaaatt tagcttggcc    840
tttgagaatt ccaacgagga agattatgtt acagaaaagt tttttcaatc gctggtaaca    900
ggagctattc cagttgtgat tggtgctcca acattcaag agttctctcc tggagaaggc     960
gcaatattac acattaaaga gcttgatgat gttccttcaa ttgccaagac aatgaaacat   1020
attgcatcaa atcaggaagc ctttaatcaa tctttgagat ggaagtatga tggcccatct   1080
gattctttca aggcccttat tgacatggca gcggttcatt catcatgtcg tctttgcata   1140
catgtcgcga cgaagattca tgagaaagag gaaaggacac caaaatttat gaatcgccca   1200
tgtagttgtt caagcaaaag aggaaaggta taccacttgt ttgtcagaga agagggcgg    1260
ttcaagacag agagcatttt tctgaggtcg gaccaattaa ctatgggtgc tttggagtct   1320
gctgtgcttg ctaaatttag atcgctcaat catgttcctg tgtggaagga tgaaagacca   1380
ccaagtatta gaggtgggga cgagttgaag gtatacaaaa tttatccaat cggccttaca   1440
caacgacagg cattatacca gttcagattt agagatgacg cagatcttga caaatacatt   1500
aaagatcatc catgtgcaaa gcttgaagtg attttgtat aa                       1542
```

<210> SEQ ID NO 39
<211> LENGTH: 513
<212> TYPE: PRT
<213> ORGANISM: Oryza sativa

<400> SEQUENCE: 39

```
Met Lys Gly Ser His Ser Gln Ser Gln Ala Gln Ala Gln Ser Gln Ala
1               5                   10                  15

Gly Arg Arg Arg Cys Gly Trp Leu Leu Pro Leu Leu Val Gly Ala
            20                  25                  30

Ala Phe Leu Ala Glu Ile Ala Phe Leu Gly Arg Leu Asp Met Ala Lys
        35                  40                  45

Asn Ala Ala Ala Val Glu Ser Trp Thr Thr Ser Phe Tyr Ala Arg Ser
    50                  55                  60

Ser Ala Pro Ala Arg Asp Gly Lys Ala Ala Val Val Pro Gly Ala
65                  70                  75                  80

Asp Ala Asp Asp Ala Pro Pro Gly Gly Gly Glu Val Val Glu Glu Asp
                85                  90                  95

Asp Gly Asp Ile Arg Leu Cys Glu Glu Arg Leu Glu Arg Glu Asp Gly
            100                 105                 110

Val Pro His Asp Arg Asp Phe Asp Lys Asp Pro Val Leu Val Gly Gly
        115                 120                 125

Ala Ala Lys Asp Trp Asn Lys Cys Ser Val Gly Cys Glu Phe Gly Phe
    130                 135                 140

Ser Ala Thr Lys Thr Pro Asp Ala Thr Phe Gly Ile Ala Pro Asp Pro
145                 150                 155                 160

Thr Val Glu Ser Ile Leu Arg Ser Met Glu Ser Ser Gln Tyr Tyr Ser
                165                 170                 175
```

Glu Asn Asn Ile Ala Val Ala Arg Gly Arg Gly Tyr Lys Ile Val Met
            180                 185                 190

Thr Thr Ser Leu Ser Ser Asp Val Pro Val Gly Tyr Phe Ser Trp Ala
        195                 200                 205

Glu Tyr Asp Ile Met Ala Pro Val Pro Pro Lys Thr Glu Glu Ala Leu
    210                 215                 220

Ala Ala Ala Phe Ile Ser Asn Cys Gly Ala Arg Asn Phe Arg Leu Gln
225                 230                 235                 240

Ala Leu Glu Met Leu Glu Ser Leu Asp Val Lys Ile Asp Ser Tyr Gly
                245                 250                 255

Ser Cys His Arg Asn His Asp Gly Lys Val Asp Lys Val Glu Thr Leu
            260                 265                 270

Lys Arg Tyr Lys Phe Ser Leu Ala Phe Glu Asn Ser Asn Glu Glu Asp
        275                 280                 285

Tyr Val Thr Glu Lys Phe Phe Gln Ser Leu Val Thr Gly Ala Ile Pro
    290                 295                 300

Val Val Ile Gly Ala Pro Asn Ile Gln Glu Phe Ser Pro Gly Glu Gly
305                 310                 315                 320

Ala Ile Leu His Ile Lys Glu Leu Asp Asp Val Pro Ser Ile Ala Lys
                325                 330                 335

Thr Met Lys His Ile Ala Ser Asn Gln Glu Ala Phe Asn Gln Ser Leu
            340                 345                 350

Arg Trp Lys Tyr Asp Gly Pro Ser Asp Ser Phe Lys Ala Leu Ile Asp
        355                 360                 365

Met Ala Ala Val His Ser Ser Cys Arg Leu Cys Ile His Val Ala Thr
    370                 375                 380

Lys Ile His Glu Lys Glu Glu Arg Thr Pro Lys Phe Met Asn Arg Pro
385                 390                 395                 400

Cys Ser Cys Ser Ser Lys Arg Gly Lys Val Tyr His Leu Phe Val Arg
                405                 410                 415

Glu Arg Gly Arg Phe Lys Thr Glu Ser Ile Phe Leu Arg Ser Asp Gln
            420                 425                 430

Leu Thr Met Gly Ala Leu Glu Ser Ala Val Leu Ala Lys Phe Arg Ser
        435                 440                 445

Leu Asn His Val Pro Val Trp Lys Asp Glu Arg Pro Pro Ser Ile Arg
    450                 455                 460

Gly Gly Asp Glu Leu Lys Val Tyr Lys Ile Tyr Pro Ile Gly Leu Thr
465                 470                 475                 480

Gln Arg Gln Ala Leu Tyr Gln Phe Arg Phe Arg Asp Asp Ala Asp Leu
                485                 490                 495

Asp Lys Tyr Ile Lys Asp His Pro Cys Ala Lys Leu Glu Val Ile Phe
            500                 505                 510

Val

<210> SEQ ID NO 40
<211> LENGTH: 1319
<212> TYPE: DNA
<213> ORGANISM: Arabidopsis thaliana

<400> SEQUENCE: 40
gtcaggaata gagaaatgcc aggagtggtt agagagagtg gattcagtta cttattctag    60
agatttcact aaagatccga tttttatctc tggtagtaac aaggacttca aatcgtgctc   120
tgttgattgt gtaatgggat tcacttcaga taagaaacct gatgcggctt ttggattaag   180

```
tcatcaacct ggaacactca gtataatccg ttccatggaa tcagcacagt attaccaaga      240
gaataatctt gctcaagcac gacggaaagg ttatgatatt gtgatgacaa ctagtctgtc      300
atcagatgtt cctgttgggt atttttcatg gcggaatat gatattatgg ctccagtgca      360
accaaaaaca gagaaagctc ttgctgccgc ttttatttcc aattgcgccg ctcggaattt      420
ccgcctgcaa gctcttgaag ccttaatgaa gacgaatgtt aagattgatt cttatggtgg      480
ttgtcaccgg aatcgggatg ggagtgtgga aaggttgaa gctcttaagc actacaaatt       540
cagtctagct tttgagaaca ccaacgagga ggattatgtc acagagaagt tcttccaatc      600
tctagtcgct ggatctgtcc ctgtggttgt tggagctcca aatatagaag aatttgcacc      660
ttctcctgac tcattccttc acattaagca gatggatgat gtcaaggcag ttgcaaagaa      720
aatgaagtat cttgcggata accctgacgc ctataatcag acgctaagat ggaaacatga      780
aggcccttca gattctttta aggcacttat tgatatggct gctgtacact cttcttgtcg      840
tctctgcatc tttgtggcta caaggattca tgagcaagaa gagaagagcc ctgagtttaa      900
gagacaaccc tgcaaatgca ccagaggctc agagacagtt tatcatttgt atgttagaga      960
aagaggacgg tttgacatgg aatccatctt cttgaaggat ggaaatctga ctctggaagc     1020
tctggaatct gcggttcttg cgaagttcat gtctctgaga tatgaaccaa tatggaagaa     1080
ggaaagaccc gcgagcttaa gaggagacgg caagcttaga gtacatggga tatatcctat     1140
tggtctgact caaagacaag ctctttacaa cttcaaattc gaaggaaatt caagtctcag     1200
tactcacata cagagaaacc cttgtcccaa attcgaagtt gtctttgtct aaattctaga     1260
agaaaaccaa agtttatttt gtgatacatg ctttgagtgt agtttgtctt aggcaggaa      1319
```

<210> SEQ ID NO 41
<211> LENGTH: 416
<212> TYPE: PRT
<213> ORGANISM: Arabidopsis thaliana

<400> SEQUENCE: 41

```
Ser Gly Ile Glu Lys Cys Gln Glu Trp Leu Glu Arg Val Asp Ser Val
1               5                   10                  15

Thr Tyr Ser Arg Asp Phe Thr Lys Asp Pro Ile Phe Ile Ser Gly Ser
            20                  25                  30

Asn Lys Asp Phe Lys Ser Cys Ser Val Asp Cys Val Met Gly Phe Thr
        35                  40                  45

Ser Asp Lys Lys Pro Asp Ala Ala Phe Gly Leu Ser His Gln Pro Gly
    50                  55                  60

Thr Leu Ser Ile Ile Arg Ser Met Glu Ser Ala Gln Tyr Tyr Gln Glu
65                  70                  75                  80

Asn Asn Leu Ala Gln Ala Arg Arg Lys Gly Tyr Asp Ile Val Met Thr
                85                  90                  95

Thr Ser Leu Ser Ser Asp Val Pro Val Gly Tyr Phe Ser Trp Ala Glu
            100                 105                 110

Tyr Asp Ile Met Ala Pro Val Gln Pro Lys Thr Glu Lys Ala Leu Ala
        115                 120                 125

Ala Ala Phe Ile Ser Asn Cys Ala Ala Arg Asn Phe Arg Leu Gln Ala
    130                 135                 140

Leu Glu Ala Leu Met Lys Thr Asn Val Lys Ile Asp Ser Tyr Gly Gly
145                 150                 155                 160

Cys His Arg Asn Arg Asp Gly Ser Val Glu Lys Val Glu Ala Leu Lys
                165                 170                 175
```

His Tyr Lys Phe Ser Leu Ala Phe Glu Asn Thr Asn Glu Glu Asp Tyr
            180                 185                 190

Val Thr Glu Lys Phe Phe Gln Ser Leu Val Ala Gly Ser Val Pro Val
        195                 200                 205

Val Val Gly Ala Pro Asn Ile Glu Glu Phe Ala Pro Ser Pro Asp Ser
    210                 215                 220

Phe Leu His Ile Lys Gln Met Asp Asp Val Lys Ala Val Ala Lys Lys
225                 230                 235                 240

Met Lys Tyr Leu Ala Asp Asn Pro Asp Ala Tyr Asn Gln Thr Leu Arg
                245                 250                 255

Trp Lys His Glu Gly Pro Ser Asp Ser Phe Lys Ala Leu Ile Asp Met
            260                 265                 270

Ala Ala Val His Ser Ser Cys Arg Leu Cys Ile Phe Val Ala Thr Arg
        275                 280                 285

Ile His Glu Gln Glu Glu Lys Ser Pro Glu Phe Lys Arg Gln Pro Cys
    290                 295                 300

Lys Cys Thr Arg Gly Ser Glu Thr Val Tyr His Leu Tyr Val Arg Glu
305                 310                 315                 320

Arg Gly Arg Phe Asp Met Glu Ser Ile Phe Leu Lys Asp Gly Asn Leu
                325                 330                 335

Thr Leu Glu Ala Leu Glu Ser Ala Val Leu Ala Lys Phe Met Ser Leu
            340                 345                 350

Arg Tyr Glu Pro Ile Trp Lys Lys Glu Arg Pro Ala Ser Leu Arg Gly
        355                 360                 365

Asp Gly Lys Leu Arg Val His Gly Ile Tyr Pro Ile Gly Leu Thr Gln
    370                 375                 380

Arg Gln Ala Leu Tyr Asn Phe Lys Phe Glu Gly Asn Ser Ser Leu Ser
385                 390                 395                 400

Thr His Ile Gln Arg Asn Pro Cys Pro Lys Phe Glu Val Val Phe Val
                405                 410                 415

<210> SEQ ID NO 42
<211> LENGTH: 1473
<212> TYPE: DNA
<213> ORGANISM: Lemna minor

<400> SEQUENCE: 42

| | |
|---|---|
| atggccacct ctgctgctgg tgctctcaac gccggtggca gggtcggggg caggaggagt | 60 |
| tgggtcagat trcttccctt ctttgtgttg atgctggtgg tagggagat ctggttcctc | 120 |
| gggcggctgg atgtggtcaa gaacgccgct atggttcaaa actggacttc ctcccacttg | 180 |
| ttttcttac cagtttcttc ctacacgtgg tccgagaccg tcaaggagga agaggattgc | 240 |
| aaggactggc tggaaagagt agatgcggtc gattacaaga gagatttccg tgtggaaccc | 300 |
| gttctggtaa atgacgctga acaggattgg agttcatgtt cagtgggctg taagttcgga | 360 |
| tcattccccg gaagaacgcc tgatgctaca tttggtttct ctcagaatcc atcaacagtc | 420 |
| agtgtccatc gatccatgga atcatcccat tattatttgg agaataatct tgataatgca | 480 |
| cgacggaaag gctatcaaat tgtgatgaca actagtctct tgtcagatgt gcctgtcggt | 540 |
| tatttctcat gggctgaata tgatatcatg gcgcctcttc agccgaaaac tgctggtgca | 600 |
| cttgctgctg catttatatc taattgcgga gcacgtaatt ccgcttgca ggcccttgat | 660 |
| atgctcgaaa agtcgaatat taagattgat tcatatggtg cttgccatcg caaccaagac | 720 |
| ggtaaagtgg acaaggtaca aactttgaag cggtataagt tcagcttagc ttttgaaaac | 780 |

```
tcgaacgagg atgactatgt tactgagaag ttctttcaat ctcttgtcgc tggagctatt    840
cctgttgtcg tcggagcccc caacattcaa aattttgcgc catcttctga ttcaattctg    900
cacatcaggg agcccaagga tgtcagttca gtcgctgaga gaatgaaatt tctcgcttca    960
aatccagaag catataacca atcactgagg tggaagtttg agggcccttc taactccttc   1020
aaagccctgg tggacatggc agcagttcac tcctcctgcc gcctatgcat tcacattgcc   1080
accaagatca gagagaagga agagagaaac ccgaatttca agactcgccc ttgcaagtgc   1140
acccgcaatg ggtctacctt atatcactta tacgcccgcg aaagaggcac ctttgacttc   1200
ttatcaatct tcatgagatc ggataatcta tcactgaaag cgctgggatc aacagttctt   1260
gagaaattca gttctttgaa gcacgtgccg atttggaaga aggagaggcc agagagtctg   1320
aaaggaggga gcaagctgga tctttacaga atctatccag tgggcattac tcagagagaa   1380
gctctcttct ctttccagtt caacactgac aaagaacttc aaatctacct tgaatcccat   1440
ccatgtgcga agtttgaagt catctttatt tga                                1473
```

<210> SEQ ID NO 43
<211> LENGTH: 490
<212> TYPE: PRT
<213> ORGANISM: Lemna minor

<400> SEQUENCE: 43

```
Met Ala Thr Ser Ala Ala Gly Ala Leu Asn Ala Gly Gly Arg Val Gly
1               5                   10                  15

Gly Arg Arg Ser Trp Val Arg Leu Leu Pro Phe Phe Val Leu Met Leu
            20                  25                  30

Val Val Gly Glu Ile Trp Phe Leu Gly Arg Leu Asp Val Val Lys Asn
        35                  40                  45

Ala Ala Met Val Gln Asn Trp Thr Ser Ser His Leu Phe Phe Leu Pro
    50                  55                  60

Val Ser Ser Tyr Thr Trp Ser Glu Thr Val Lys Glu Glu Asp Cys
65                  70                  75                  80

Lys Asp Trp Leu Glu Arg Val Asp Ala Val Asp Tyr Lys Arg Asp Phe
                85                  90                  95

Arg Val Glu Pro Val Leu Val Asn Asp Ala Glu Gln Asp Trp Ser Ser
            100                 105                 110

Cys Ser Val Gly Cys Lys Phe Gly Ser Phe Pro Gly Arg Thr Pro Asp
        115                 120                 125

Ala Thr Phe Gly Phe Ser Gln Asn Pro Ser Thr Val Ser Val His Arg
    130                 135                 140

Ser Met Glu Ser Ser His Tyr Tyr Leu Glu Asn Asn Leu Asp Asn Ala
145                 150                 155                 160

Arg Arg Lys Gly Tyr Gln Ile Val Met Thr Thr Ser Leu Leu Ser Asp
                165                 170                 175

Val Pro Val Gly Tyr Phe Ser Trp Ala Glu Tyr Asp Ile Met Ala Pro
            180                 185                 190

Leu Gln Pro Lys Thr Ala Gly Ala Leu Ala Ala Ala Phe Ile Ser Asn
        195                 200                 205

Cys Gly Ala Arg Asn Phe Arg Leu Gln Ala Leu Asp Met Leu Glu Lys
    210                 215                 220

Ser Asn Ile Lys Ile Asp Ser Tyr Gly Ala Cys His Arg Asn Gln Asp
225                 230                 235                 240

Gly Lys Val Asp Lys Val Gln Thr Leu Lys Arg Tyr Lys Phe Ser Leu
```

```
                245                 250                 255
Ala Phe Glu Asn Ser Asn Glu Asp Asp Tyr Val Thr Glu Lys Phe Phe
            260                 265                 270

Gln Ser Leu Val Ala Gly Ala Ile Pro Val Val Gly Ala Pro Asn
        275                 280                 285

Ile Gln Asn Phe Ala Pro Ser Ser Asp Ser Ile Leu His Ile Arg Glu
        290                 295                 300

Pro Lys Asp Val Ser Ser Val Ala Glu Arg Met Lys Phe Leu Ala Ser
305                 310                 315                 320

Asn Pro Glu Ala Tyr Asn Gln Ser Leu Arg Trp Lys Phe Glu Gly Pro
                325                 330                 335

Ser Asn Ser Phe Lys Ala Leu Val Asp Met Ala Ala Val His Ser Ser
            340                 345                 350

Cys Arg Leu Cys Ile His Ile Ala Thr Lys Ile Arg Glu Lys Glu Glu
        355                 360                 365

Arg Asn Pro Asn Phe Lys Thr Arg Pro Cys Lys Cys Thr Arg Asn Gly
    370                 375                 380

Ser Thr Leu Tyr His Leu Tyr Ala Arg Glu Arg Gly Thr Phe Asp Phe
385                 390                 395                 400

Leu Ser Ile Phe Met Arg Ser Asp Asn Leu Ser Leu Lys Ala Leu Gly
                405                 410                 415

Ser Thr Val Leu Glu Lys Phe Ser Leu Lys His Val Pro Ile Trp
            420                 425                 430

Lys Lys Glu Arg Pro Glu Ser Leu Lys Gly Gly Ser Lys Leu Asp Leu
        435                 440                 445

Tyr Arg Ile Tyr Pro Val Gly Ile Thr Gln Arg Glu Ala Leu Phe Ser
    450                 455                 460

Phe Gln Phe Asn Thr Asp Lys Glu Leu Gln Ile Tyr Leu Glu Ser His
465                 470                 475                 480

Pro Cys Ala Lys Phe Glu Val Ile Phe Ile
                485                 490

<210> SEQ ID NO 44
<211> LENGTH: 1750
<212> TYPE: DNA
<213> ORGANISM: Triticum aestivum

<400> SEQUENCE: 44
cacgcgtcgc ctgtccaccc tagccgccgc cagccaacgg aaagagccgt gaggctccct      60
aacgcccatg aagggctccc actcgcagtc ccaggcggca agccgtcggc ggcgctgtgg     120
gtggctgctc ccgcttctcg ttggtgttgc ttttgtcggc gagatcgcgt tcctcggtcg     180
cctcgacatg tcgaagaacg ctgcggcggt cgagagctgg accacctcct tctaccgcct     240
ctcttcgacc tggggcgcgg acgcacctcc gggtagcggg acgacgacg  acgagtgcga     300 ggagcggctc gagagggagg acgccgtgcc ctacgaccgc gattttgaaa gggatcccgt     360
acttgtcggc ggtgctgcta aggattggaa tagatgttct gtaggatgtg aattcgggtt     420
tccagctagt aagacacctg atgctacttt cggaatcgct ccagatcctt ccgtagagag     480
tatcctcaga tcaatggaat cgtctcaata ttattccgag aacaatatta atgcggctcg     540
aggaagaggg taccaaattg tgatgacaac cagcctttcc tcagatgtgc cggttggcta     600
cttttcatgg gctgaatatg atatcatggc acctgtgcct ccaaagactg aagaagccct     660
agctgcagcc tttatttcca actgcggtgc acgcaacttt cgtttgcaag cccttgagat     720
```

```
gcttgaaagc ttagatgtaa aaattgattc ttatggtagc tgtcatcgta atcgtgatgg    780
caaagtggac aaagtggaga ctctaaagcg ctacaaattc agcttggctt ttgagaattc    840
tggtgaggaa gattatgtta cagaaaagtt ttttcagtca ctggtaacgg gggccattcc    900
agttgtcgtt ggcgcaccaa atattcaaga gttttctcca ggagaaggtg caatattaca    960
cattaaggag cttgatgatg tcatttcagt tgctaagaca atgaaacata ttgcatcgaa   1020
tcctgatgct tttaatcaat ctttgaggtg gaagtacgat ggtccatctg attctttcaa   1080
ggcacttatt gacatggcag cggttcattc atcctgtcgc ctttgcatac atatcgctac   1140
gaagattcac gaaaaagaag aaagaacgcc aaaatttatg aatcgctcat gtagttgctc   1200
cagcaaaaga ggaacagtat accacttatt tgtcagagag agagggcggt ttaagacaga   1260
gagcatttat ctaagatcag atcagttaac tttaggagct ttggagtctg ccgtgcatgg   1320
taaatttaga tccctcaagc atgttcctgt atggaaggat gaaaggccat caagtattcg   1380
aggcggggat gagttgaagg tgtacaaaat ttacccaata ggtcttacag aaagacaagc   1440
gttatataaa tttcaattca gtgatgatgc tgaagttgct agatatatta agggccatcc   1500
atgtgcaaag cttgaggtga tttttgtata actacaatat tgccatcttc tctacctttt   1560
gcaactgcaa actagttctg tgtattgagt ttctgctgta ctgtaataga ttcccgttta   1620
tgtaacgtca accttggtac aagtcacaac tttgtaggct ttgtgatact gggatgtaaa   1680
tttctattga aggcaagtac atcttttgcg ggaaacaatt aacatggatt gcgtaaaaaa   1740
aaaaaaaaaa                                                          1750

<210> SEQ ID NO 45
<211> LENGTH: 487
<212> TYPE: PRT
<213> ORGANISM: Triticum aestivum

<400> SEQUENCE: 45

Met Lys Gly Ser His Ser Gln Ser Gln Ala Ala Ser Arg Arg Arg Arg
1               5                   10                  15

Cys Gly Trp Leu Leu Pro Leu Leu Val Gly Val Ala Phe Val Gly Glu
            20                  25                  30

Ile Ala Phe Leu Gly Arg Leu Asp Met Ser Lys Asn Ala Ala Ala Val
        35                  40                  45

Glu Ser Trp Thr Thr Ser Phe Tyr Arg Leu Ser Ser Thr Trp Gly Ala
    50                  55                  60

Asp Ala Pro Pro Gly Ser Gly Asp Asp Asp Asp Glu Cys Glu Glu Arg
65                  70                  75                  80

Leu Glu Arg Glu Asp Ala Val Pro Tyr Asp Arg Asp Phe Glu Arg Asp
                85                  90                  95

Pro Val Leu Val Gly Gly Ala Ala Lys Asp Trp Asn Arg Cys Ser Val
            100                 105                 110

Gly Cys Glu Phe Gly Phe Pro Ala Ser Lys Thr Pro Asp Ala Thr Phe
        115                 120                 125

Gly Ile Ala Pro Asp Pro Ser Val Glu Ser Ile Leu Arg Ser Met Glu
    130                 135                 140

Ser Ser Gln Tyr Tyr Ser Glu Asn Asn Ile Asn Ala Ala Arg Gly Arg
145                 150                 155                 160

Gly Tyr Gln Ile Val Met Thr Thr Ser Leu Ser Ser Asp Val Pro Val
                165                 170                 175

Gly Tyr Phe Ser Trp Ala Glu Tyr Asp Ile Met Ala Pro Val Pro Pro
            180                 185                 190
```

Lys Thr Glu Glu Ala Leu Ala Ala Phe Ile Ser Asn Cys Gly Ala
    195                 200                 205

Arg Asn Phe Arg Leu Gln Ala Leu Glu Met Leu Glu Ser Leu Asp Val
210                 215                 220

Lys Ile Asp Ser Tyr Gly Ser Cys His Arg Asn Arg Asp Gly Lys Val
225                 230                 235                 240

Asp Lys Val Glu Thr Leu Lys Arg Tyr Lys Phe Ser Leu Ala Phe Glu
                245                 250                 255

Asn Ser Gly Glu Glu Asp Tyr Val Thr Glu Lys Phe Phe Gln Ser Leu
                260                 265                 270

Val Thr Gly Ala Ile Pro Val Val Gly Ala Pro Asn Ile Gln Glu
                275                 280                 285

Phe Ser Pro Gly Glu Gly Ala Ile Leu His Ile Lys Glu Leu Asp Asp
                290                 295                 300

Val Ile Ser Val Ala Lys Thr Met Lys His Ile Ala Ser Asn Pro Asp
305                 310                 315                 320

Ala Phe Asn Gln Ser Leu Arg Trp Lys Tyr Asp Gly Pro Ser Asp Ser
                325                 330                 335

Phe Lys Ala Leu Ile Asp Met Ala Ala Val His Ser Ser Cys Arg Leu
                340                 345                 350

Cys Ile His Ile Ala Thr Lys Ile His Glu Lys Glu Arg Thr Pro
                355                 360                 365

Lys Phe Met Asn Arg Ser Cys Ser Cys Ser Lys Arg Gly Thr Val
                370                 375                 380

Tyr His Leu Phe Val Arg Glu Arg Gly Arg Phe Lys Thr Glu Ser Ile
385                 390                 395                 400

Tyr Leu Arg Ser Asp Gln Leu Thr Leu Gly Ala Leu Glu Ser Ala Val
                405                 410                 415

His Gly Lys Phe Arg Ser Leu Lys His Val Pro Val Trp Lys Asp Glu
                420                 425                 430

Arg Pro Ser Ser Ile Arg Gly Gly Asp Glu Leu Lys Val Tyr Lys Ile
                435                 440                 445

Tyr Pro Ile Gly Leu Thr Glu Arg Gln Ala Leu Tyr Lys Phe Gln Phe
                450                 455                 460

Ser Asp Asp Ala Glu Val Ala Arg Tyr Ile Lys Gly His Pro Cys Ala
465                 470                 475                 480

Lys Leu Glu Val Ile Phe Val
                485

<210> SEQ ID NO 46
<211> LENGTH: 1633
<212> TYPE: DNA
<213> ORGANISM: Hordeum vulgare

<400> SEQUENCE: 46
caattcttcc agcggaaaga cccgtgaggc tcactaacgc ccctgatggg ctcccactcg    60
ctgacccagg cggcaagccg tcggcggcgc tgcgggtggc tgctcccgct tgtcgttggt   120
gttgcttttc tcggcgagat cgcgttcctc ggtcgcctcg acatgtcgaa gaacgctgcg   180
gcggtcgaga gctggaccac ctccttccac cgcctctctt caacctgggg cgcggatgcg   240
cctccgggta gcggggacga cgacgaagag tgcgaggagc ggcttgagag ggacgacgcc   300
gtgccttacg accgcgattt tgaaaggcat cctgtacttg tcggcggtgc tgctaaggat   360
tggaatagat gttctgtagg atgtgaattt gggtttccag ctagtaagac gcctgatgct   420

```
actttcggaa tcgctccaga tccttccgta gagagtatcc tcagatcaat ggaatcgtct    480
caatattatt ccgagaacaa tattaatgcg gctcgaggaa gagggtacca aattgtgatg    540
acaaccagcc tttcctcaga tgtgccagtt ggctactttt catgggctga atatgatatc    600
atggcacctg tgcctccaaa gactgaagag gccctagctg cagcctttat ttccaactgc    660
ggtgcacgaa acttccgttt gcaagccctt gagatgcttg aaagcttaga tgtaaaaatt    720
gattcttatg gtagctgtca tcgtaatcgt gatggcaaag tggacaaagt ggagactcta    780
aagggctaca aattcagctt ggcttttgag aattctaatg aggaagatta tgttacagaa    840
aagttctttc agtcactggt aacaggggcc attccagttg tcgttggcgc accgaatatt    900
caagagtttt ctccaggaga agatgcaata ttacacatca aggagcttga tgatgtcatt    960
tcagttgcga agacaatgaa acatattgca tcaaatcctg atgcttttaa tcaatctttg   1020
aggtggaagt atgatggtcc atctgattct ttcaaggcac ttattgacat ggcagcggtt   1080
cattcatcct gtcgcctttg tatacatatc gctacgaaga ttcatgaaaa agaagaaaaa   1140
actccaaaat ttatgaatcg ctcgtgtagt tgctccagca aagaggaac agtataccac    1200
ttatttgtca gagagagagg gcggtttaag acagagaaca tttatctaag atcagatcag   1260
ttaactttag gagctttgaa gtctgctgtg cacgataaat ttagctccct caagcatgtt   1320
cctatatgga aggatgaaag gccatcaagt attcgaggtg gggatgaatt gaaggtgtac   1380
aaaatttatc caataggtct tacagaacga caagcgttat ataaatttca attcagtgac   1440
gatgctgaag ttgctagata tattaagggc catccatgtg caaagcttga ggtgattttt   1500
gtataactac aatattgcca tcttcacgtc tttttgcaac tgcgaactag ttctgcgtgt   1560
actgtaacag attcctgttt atgtaacgtc aaccttaata caaaatcaca actttgtagg   1620
ctttaaaaaa aaa                                                       1633
```

<210> SEQ ID NO 47
<211> LENGTH: 486
<212> TYPE: PRT
<213> ORGANISM: Hordeum vulgare

<400> SEQUENCE: 47

Met Gly Ser His Ser Leu Thr Gln Ala Ala Ser Arg Arg Arg Cys
1               5                   10                  15

Gly Trp Leu Leu Pro Leu Val Val Gly Val Ala Phe Leu Gly Glu Ile
                20                  25                  30

Ala Phe Leu Gly Arg Leu Asp Met Ser Lys Asn Ala Ala Ala Val Glu
            35                  40                  45

Ser Trp Thr Thr Ser Phe His Arg Leu Ser Ser Thr Trp Gly Ala Asp
        50                  55                  60

Ala Pro Pro Gly Ser Gly Asp Asp Glu Glu Cys Glu Glu Arg Leu
65                  70                  75                  80

Glu Arg Asp Asp Ala Val Pro Tyr Asp Arg Asp Phe Glu Arg His Pro
                85                  90                  95

Val Leu Val Gly Gly Ala Ala Lys Asp Trp Asn Arg Cys Ser Val Gly
            100                 105                 110

Cys Glu Phe Gly Phe Pro Ala Ser Lys Thr Pro Asp Ala Thr Phe Gly
        115                 120                 125

Ile Ala Pro Asp Pro Ser Val Glu Ser Ile Leu Arg Ser Met Glu Ser
    130                 135                 140

Ser Gln Tyr Tyr Ser Glu Asn Asn Ile Asn Ala Ala Arg Gly Arg Gly

```
            145                 150                 155                 160
Tyr Gln Ile Val Met Thr Thr Ser Leu Ser Ser Asp Val Pro Val Gly
                165                 170                 175

Tyr Phe Ser Trp Ala Glu Tyr Asp Ile Met Ala Pro Val Pro Pro Lys
                180                 185                 190

Thr Glu Glu Ala Leu Ala Ala Phe Ile Ser Asn Cys Gly Ala Arg
                195                 200                 205

Asn Phe Arg Leu Gln Ala Leu Glu Met Leu Gly Ser Leu Asp Val Lys
    210                 215                 220

Ile Asp Ser Tyr Gly Ser Cys His Arg Asn Arg Asp Gly Lys Val Asp
225                 230                 235                 240

Lys Val Glu Thr Leu Lys Gly Tyr Lys Phe Ser Leu Ala Phe Glu Asn
                245                 250                 255

Ser Asn Glu Glu Asp Tyr Val Thr Glu Lys Phe Phe Gln Ser Leu Val
                260                 265                 270

Thr Gly Ala Ile Pro Val Val Val Gly Ala Pro Asn Ile Gln Glu Phe
                275                 280                 285

Ser Pro Gly Glu Asp Ala Ile Leu His Ile Lys Glu Leu Asp Asp Val
    290                 295                 300

Ile Ser Val Ala Lys Thr Met Lys His Ile Ala Ser Asn Pro Asp Ala
305                 310                 315                 320

Phe Asn Gln Ser Leu Arg Trp Lys Tyr Asp Gly Pro Ser Asp Ser Phe
                325                 330                 335

Lys Ala Leu Ile Asp Met Ala Ala Val His Ser Ser Cys Arg Leu Cys
                340                 345                 350

Ile His Ile Ala Thr Lys Ile His Glu Lys Glu Lys Thr Pro Lys
                355                 360                 365

Phe Met Asn Arg Ser Cys Ser Cys Ser Ser Lys Arg Gly Thr Val Tyr
    370                 375                 380

His Leu Phe Val Arg Glu Arg Gly Arg Phe Lys Thr Glu Asn Ile Tyr
385                 390                 395                 400

Leu Arg Ser Asp Gln Leu Thr Leu Gly Ala Leu Lys Ser Ala Val His
                405                 410                 415

Asp Lys Phe Ser Ser Leu Lys His Val Pro Ile Trp Lys Asp Glu Arg
                420                 425                 430

Pro Ser Ser Ile Arg Gly Gly Asp Glu Leu Lys Val Tyr Lys Ile Tyr
                435                 440                 445

Pro Ile Gly Leu Thr Glu Arg Gln Ala Leu Tyr Lys Phe Gln Phe Ser
    450                 455                 460

Asp Asp Ala Glu Val Ala Arg Tyr Ile Lys Gly His Pro Cys Ala Lys
465                 470                 475                 480

Leu Glu Val Ile Phe Val
                485

<210> SEQ ID NO 48
<211> LENGTH: 1419
<212> TYPE: DNA
<213> ORGANISM: Oryza sativa

<400> SEQUENCE: 48
ggccgcctcg acatggcgaa gaacgccgcc gcggtcgaga gctggaccac ctccttctac      60
gcccgctcct ccgcccccgc ccgcgacggg aaggcagcgg tcgtggtccc cggcgcggac     120
tcggacgacg cgcccccggg cggaggtgag gtggtggagg aggacgacgg cgacatccgg     180
```

```
ttgtgcgagg agcggcttga gagggaggac ggcgtgccgc acgaccgcga cttcgacaag    240
gatcccgtcc tcgtcggggg cgccgctaag gattggaata aatgttctgt aggatgtgaa    300
tttgggtttt cagctactaa gacgcctgat gctacttttg gaattgcccc agatcctact    360
gtagagagta tcctcagatc gatggagtca tctcagtatt attcagagaa caacattgct    420
gtggctcgag ggagaggtta caaaattgtg atgacaacaa gcctttcctc agatgtacct    480
gttggctact tttcatgggc tgaatatgat ataatggcac ctgtgcctcc aaaaactgaa    540
gaagccctag ctgcagcatt tatttcaaac tgtggtgcac gtaattttcg tttgcaagcc    600
cttgagatgc ttgagagctt agatgtcaaa attgattcat atggtagttg ccatcgtaat    660
catgatggca agttgataa agtggaaact ttgaagcgct acaaatttag cttggccttt    720
gagaattcca acgaggaaga ttatgttaca gaaaagtttt ttcaatcgct ggtaacagga    780
gctattccag ttgtgattgg tgctccaaac attcaagagt tctcccctgg agaaggcgca    840
atattacaca ttaaagagct tgatgatgtt ccttcaattg ccaagacaat gaaacatatt    900
gcatcaaatc aggaagcctt taatcaatct ttgagatgga gtatgatgg cccatctgat    960
tctttcaagg cccttattga catggcagcg gttcattcat catgtcgtct ttgcatacat    1020
gtcgcgacga agattcatga aaagaggaa aggacaccaa aatttatgaa tcgcccatgt    1080
agttgttcaa gcaaaagagg aaaggtatac cacttgtttg tcagagaaag agggcggttc    1140
aagacagaga gcatttttct gaggtcggac caattaacta tgggtgcttt ggagtctgct    1200
gtgcttgcta aatttagatc gctcaatcat gttcctgtgt ggaaggatga aagaccacca    1260
agtattagag gtggggacga gttgaaggta tacaaaattt atccaatcgg ccttacacaa    1320
cgacaggcat taccagtt cagatttaga gatgacgcag atcttgacaa atacattaaa    1380
gatcatccat gtgcaaagct tgaagtgatt tttgtataa                          1419
```

<210> SEQ ID NO 49
<211> LENGTH: 472
<212> TYPE: PRT
<213> ORGANISM: Oryza sativa

<400> SEQUENCE: 49

Gly Arg Leu Asp Met Ala Lys Asn Ala Ala Ala Val Glu Ser Trp Thr
1               5                   10                  15

Thr Ser Phe Tyr Ala Arg Ser Ser Ala Pro Ala Arg Asp Gly Lys Ala
            20                  25                  30

Ala Val Val Val Pro Gly Ala Asp Ser Asp Asp Ala Pro Pro Gly Gly
        35                  40                  45

Gly Glu Val Val Glu Glu Asp Asp Gly Asp Ile Arg Leu Cys Glu Glu
    50                  55                  60

Arg Leu Glu Arg Glu Asp Gly Val Pro His Asp Arg Asp Phe Asp Lys
65                  70                  75                  80

Asp Pro Val Leu Val Gly Gly Ala Ala Lys Asp Trp Asn Lys Cys Ser
                85                  90                  95

Val Gly Cys Glu Phe Gly Phe Ser Ala Thr Lys Thr Pro Asp Ala Thr
            100                 105                 110

Phe Gly Ile Ala Pro Asp Pro Thr Val Glu Ser Ile Leu Arg Ser Met
        115                 120                 125

Glu Ser Ser Gln Tyr Tyr Ser Glu Asn Asn Ile Ala Val Ala Arg Gly
    130                 135                 140

Arg Gly Tyr Lys Ile Val Met Thr Thr Ser Leu Ser Ser Asp Val Pro
145                 150                 155                 160

Val Gly Tyr Phe Ser Trp Ala Glu Tyr Asp Ile Met Ala Pro Val Pro
            165                 170                 175

Pro Lys Thr Glu Glu Ala Leu Ala Ala Ala Phe Ile Ser Asn Cys Gly
        180                 185                 190

Ala Arg Asn Phe Arg Leu Gln Ala Leu Glu Met Leu Glu Ser Leu Asp
    195                 200                 205

Val Lys Ile Asp Ser Tyr Gly Ser Cys His Arg Asn His Asp Gly Lys
210                 215                 220

Val Asp Lys Val Glu Thr Leu Lys Arg Tyr Lys Phe Ser Leu Ala Phe
225                 230                 235                 240

Glu Asn Ser Asn Glu Glu Asp Tyr Val Thr Glu Lys Phe Phe Gln Ser
            245                 250                 255

Leu Val Thr Gly Ala Ile Pro Val Val Ile Gly Ala Pro Asn Ile Gln
            260                 265                 270

Glu Phe Ser Pro Gly Glu Gly Ala Ile Leu His Ile Lys Glu Leu Asp
        275                 280                 285

Asp Val Pro Ser Ile Ala Lys Thr Met Lys His Ile Ala Ser Asn Gln
290                 295                 300

Glu Ala Phe Asn Gln Ser Leu Arg Trp Lys Tyr Asp Gly Pro Ser Asp
305                 310                 315                 320

Ser Phe Lys Ala Leu Ile Asp Met Ala Ala Val His Ser Ser Cys Arg
            325                 330                 335

Leu Cys Ile His Val Ala Thr Lys Ile His Glu Lys Glu Glu Arg Thr
            340                 345                 350

Pro Lys Phe Met Asn Arg Pro Cys Ser Cys Ser Ser Lys Arg Gly Lys
        355                 360                 365

Val Tyr His Leu Phe Val Arg Glu Arg Gly Arg Phe Lys Thr Glu Ser
        370                 375                 380

Ile Phe Leu Arg Ser Asp Gln Leu Thr Met Gly Ala Leu Glu Ser Ala
385                 390                 395                 400

Val Leu Ala Lys Phe Arg Ser Leu Asn His Val Pro Val Trp Lys Asp
            405                 410                 415

Glu Arg Pro Pro Ser Ile Arg Gly Gly Asp Glu Leu Lys Val Tyr Lys
            420                 425                 430

Ile Tyr Pro Ile Gly Leu Thr Gln Arg Gln Ala Leu Tyr Gln Phe Arg
        435                 440                 445

Phe Arg Asp Asp Ala Asp Leu Asp Lys Tyr Ile Lys Asp His Pro Cys
450                 455                 460

Ala Lys Leu Glu Val Ile Phe Val
465                 470

<210> SEQ ID NO 50
<211> LENGTH: 1937
<212> TYPE: DNA
<213> ORGANISM: Zea mays

<400> SEQUENCE: 50
cgcgtctctc tccctgctt ccatggctgc cgtacccttt gctcctccca gccagccgag      60
gtctcttccg aagcaccgcc ggccatctcg agggagatct ggcgcccggc caccctcacc     120
tcatccactt cctggcgttc gtcctcggct ccctcacgcc gtgtgctcct ccctggtact     180
cgagatcgcc catggagccc agccccatgc ggcgctccgc tcgctcttgt ctggtggctg     240
gtgcgcgcag gcgccgggct cagggagccc cggcaagagc tggcgttgtg gcgggccgcc     300

```
ggcggcgatg gaggtgcttg ctgccgctcc tcgtaggcgc cgccttcctc gccgagatcg    360
ccttcctcgg ccgcctcgac atggcgaaga acgccgaggt ggtcgagagc tggaccacct    420
cctttttaccg ccgctcctcc cattggggtg aagccgtggg ccggggcgcg gtcccgaggg    480
caggcggcga cggcgaggac gaagagatcc ggcggtgcga gcagcggctc gagagggagg    540
acgccgtgcc ctacgaccgc gactttgaca gggatcccgt gcttgtcggt ggcgctgcca    600
aggactggag taaatgctac gtaggatgtg aatttggttt ttctgccagt aagacacctg    660
atgctacttt tggaattgca ccagatcctt ctgtagaggg tatcctcaga tcaatggaat    720
catctcaata ttattcaaag aataatattg atgtggctcg agggagaggg tacaagattg    780
tgatgacaac cagcctttct tcagacgtcc cagttggcta cttttcatgg gctgaatatg    840
atatcatggc acctgtgcct ccaaagactg aagaagctct tgctgcagcc tttatttcta    900
actgtggtgc acggaacttc cgtttgcaag cccttgagat gcttgaaaat ttggatgtca    960
aaatagattc atatggtagt tgtcatcgca accgtggtga caaagtggac accttgaagc    1020
gctacagatt cagcttggca tttgagaatt ctaatgagga ggattacgta acagaaaagt    1080
ttttttttccg atcactggta ctgtctattc cagttgttgt tggtgctcca aatattcagg    1140
agctttctcc tggagaaggc gcaatattac acattaagga gcttgatgat gttgtttcag    1200
ttgctaagac aatgaaaaat attgcttcaa atcctgacgc cttcaatcaa tctttgaggt    1260
ggaagtatga tgggccatcc gattctttca agctcttat cgacatggca gcggttcatt    1320
catcttgtcg tctttgtata catattgcta ccaagatcca tttaaaggag gaaaggactc    1380
caaaatttac aaatcgtcct tgtagctgtt ccaccaaaaa gggaacaatt taccacttat    1440
ttatccgaga gagagggcgg tttaagtcag agagcattta catgagatca ggccagttaa    1500
cactgggagc cttggaatcc gcagtgctcg gtaaatttag gtccctcaac cacgttcctg    1560
tatggaagga tgaaaggcca ccgagcatta gaggtgggga tgacctgaaa ctatacagaa    1620
tttacccagt cggtctaacg caacgtcagg cttttgtacgg tttcagattt agagatgatt    1680
ctaaactcga gcaatacatc aaagaccatc cctgtgcaaa gcttgaagta attttttgtgt    1740
aactactatg ccctaggctt aacgttcgcc ccccgattct tactgaactc cgtgtgcgga    1800
gtttcagtta tactgtaatg tagagtgtca tgtgtagcaa acaaactcat gccagtacag    1860
atcatgtgcc ggatgaaaat tttccatgac agtaaacatc attccttctt ttcagtacac    1920
cgcaaacaaa ttaacac                                                   1937
```

<210> SEQ ID NO 51
<211> LENGTH: 516
<212> TYPE: PRT
<213> ORGANISM: Zea mays

<400> SEQUENCE: 51

```
Met Glu Pro Ser Pro Met Arg Arg Ser Ala Arg Ser Cys Leu Val Ala
1               5                   10                  15

Gly Ala Arg Arg Arg Ala Gln Gly Ala Pro Ala Arg Ala Gly Val
            20                  25                  30

Val Ala Gly Arg Arg Arg Trp Arg Cys Leu Leu Pro Leu Leu Val
        35                  40                  45

Gly Ala Ala Phe Leu Ala Glu Ile Ala Phe Leu Gly Arg Leu Asp Met
    50                  55                  60

Ala Lys Asn Ala Glu Val Val Glu Ser Trp Thr Thr Ser Phe Tyr Arg
65                  70                  75                  80
```

-continued

```
Arg Ser Ser His Trp Gly Glu Ala Val Gly Arg Gly Ala Val Pro Arg
                85                  90                  95

Ala Gly Gly Asp Gly Glu Asp Glu Ile Arg Arg Cys Glu Gln Arg
            100                 105                 110

Leu Glu Arg Glu Asp Ala Val Pro Tyr Asp Arg Asp Phe Asp Arg Asp
            115                 120                 125

Pro Val Leu Val Gly Gly Ala Ala Lys Asp Trp Ser Lys Cys Tyr Val
            130                 135                 140

Gly Cys Glu Phe Gly Phe Ser Ala Ser Lys Thr Pro Asp Ala Thr Phe
145                 150                 155                 160

Gly Ile Ala Pro Asp Pro Ser Val Glu Gly Ile Leu Arg Ser Met Glu
                165                 170                 175

Ser Ser Gln Tyr Tyr Ser Lys Asn Asn Ile Asp Val Ala Arg Gly Arg
            180                 185                 190

Gly Tyr Lys Ile Val Met Thr Thr Ser Leu Ser Ser Asp Val Pro Val
            195                 200                 205

Gly Tyr Phe Ser Trp Ala Glu Tyr Asp Ile Met Ala Pro Val Pro Pro
            210                 215                 220

Lys Thr Glu Glu Ala Leu Ala Ala Phe Ile Ser Asn Cys Gly Ala
225                 230                 235                 240

Arg Asn Phe Arg Leu Gln Ala Leu Glu Met Leu Glu Asn Leu Asp Val
                245                 250                 255

Lys Ile Asp Ser Tyr Gly Ser Cys His Arg Asn Arg Gly Asp Lys Val
            260                 265                 270

Asp Thr Leu Lys Arg Tyr Arg Phe Ser Leu Ala Phe Glu Asn Ser Asn
            275                 280                 285

Glu Glu Asp Tyr Val Thr Glu Lys Phe Phe Phe Arg Ser Leu Val Leu
290                 295                 300

Ser Ile Pro Val Val Gly Ala Pro Asn Ile Gln Glu Leu Ser Pro
305                 310                 315                 320

Gly Glu Gly Ala Ile Leu His Ile Lys Glu Leu Asp Asp Val Val Ser
                325                 330                 335

Val Ala Lys Thr Met Lys Asn Ile Ala Ser Asn Pro Asp Ala Phe Asn
            340                 345                 350

Gln Ser Leu Arg Trp Lys Tyr Asp Gly Pro Ser Asp Ser Phe Lys Ala
            355                 360                 365

Leu Ile Asp Met Ala Ala Val His Ser Ser Cys Arg Leu Cys Ile His
            370                 375                 380

Ile Ala Thr Lys Ile His Leu Lys Glu Glu Arg Thr Pro Lys Phe Thr
385                 390                 395                 400

Asn Arg Pro Cys Ser Cys Ser Thr Lys Lys Gly Thr Ile Tyr His Leu
                405                 410                 415

Phe Ile Arg Glu Arg Gly Arg Phe Lys Ser Glu Ser Ile Tyr Met Arg
            420                 425                 430

Ser Gly Gln Leu Thr Leu Gly Ala Leu Glu Ser Ala Val Leu Gly Lys
            435                 440                 445

Phe Arg Ser Leu Asn His Val Pro Val Trp Lys Asp Glu Arg Pro Pro
450                 455                 460

Ser Ile Arg Gly Gly Asp Asp Leu Lys Leu Tyr Arg Ile Tyr Pro Val
465                 470                 475                 480

Gly Leu Thr Gln Arg Gln Ala Leu Tyr Gly Phe Arg Phe Arg Asp Asp
                485                 490                 495

Ser Lys Leu Glu Gln Tyr Ile Lys Asp His Pro Cys Ala Lys Leu Glu
```

```
                    500                 505                 510
Val Ile Phe Val
        515

<210> SEQ ID NO 52
<211> LENGTH: 1602
<212> TYPE: DNA
<213> ORGANISM: Physcomitrella patens

<400> SEQUENCE: 52 atgaaggag  ataggatac   agggcgattt  cgcagggatg  atgctgcttt  tgaacgggat     60
gtggaaggtg  gtgaaagacc  cacacccggg  ctattaggct  tgaggtctct  ggcatctagc    120
tcaggacggg  gatggtggag  caaaactgtt  ttgtgggccg  tatttgctgt  tgtcctcatt    180
gaatgcgctt  tcattgttcg  ccttgatatt  ttgaattccc  cttcttcatc  ttactcgtcc    240
tctcttgatt  cccaccccga  gaatcccaac  aaaatctctg  acaagaaga   actaacgata    300 aaaaccaata  aaacaattcg  gattgacaag  ttaccaacgg  gaacagatga  tgtctgctcg    360
gcagaatggc  tagagaaggt  tgacaaagtt  acatactcgc  gtgattttaa  gaagaaacct    420
gtgctggttg  tatcgggaaa  tgaagttgag  aattgggata  aatgttctgt  gccatgcgtg    480
ttcaaggccc  atggtgaggg  tcaggcagat  gcagagtttg  gctatggaga  ttcaccctcg    540
gcactactag  tgttacgctc  tatgaatct   tctgcttatt  ttcctgagaa  tgacatcgtg    600
tgggcgcgaa  gcaacggagt  gggtgtggtg  atgactacaa  gcctgtcatc  ggatgttcca    660
gagggctact  tttcgtgggc  ggagtacaaa  atcacggatg  ctcccaagcc  caagacaaaa    720
ccaactcttg  gagctgcttt  tatttccaac  tgtggtgcgc  ataatgatcg  tcttaccatt    780
atgcgaatgt  taccaaacga  aggcgttcga  atagactcat  acggttcttg  cgaaccaaat    840
gttcttggag  gccgagcatt  gaacaagttg  gaaactcttc  gagagtacaa  gtttagcctt    900
gctttcgaaa  attccaacgt  tgaggattat  gttacggaga  agttctttca  atccttagtt    960
gctggctcag  tccctattgt  aacgggacct  ccaaatattt  atgacttcgc  accgcatca   1020 aattctcttg  tatacattaa  ggacgttagc  gaagtaaagg  ctgcagcaag  tcccataaaa   1080
tatctcgcag  aaaacgagac  tgcgtacaac  gagactttgc  agtggaagtt  taatggtcct   1140
tcagattcgt  ttctagctct  agtagacatg  gccgccgtgc  actcctcctg  caggttatgc   1200
atctttgtag  ctaccaaatc  gcgcctgaaa  gaagaagcgg  ctgctcctaa  agaccttgc   1260 aagtgcacca  gcaaatctgg  gtccaccctc  taccatttat  atgtacgaga  gcggggtcgt   1320
ttcgaaatgg  aatcggtttt  tattgaagga  tcgaaacttt  ccctagccca  tttgaagcaa   1380
gttgtagtag  acaagttcac  ggccctcaag  catgttccta  tttggaagac  agagcggccc   1440
gaagttatta  ggggggaactc  agaccttcgg  atctacaaaa  tatatcctgt  gggccttact   1500
caacgggagg  cgctttatac  ttgggatttc  ggtggtgata  agggggataaa  ggctatggtt   1560 caaaaacaac  cttgtcttca  attggaagta  gttttgtttt  ga                       1602

<210> SEQ ID NO 53
<211> LENGTH: 533
<212> TYPE: PRT
<213> ORGANISM: Physcomitrella patens

<400> SEQUENCE: 53

Met Lys Gly Asp Arg Asp Thr Gly Arg Phe Arg Arg Asp Asp Ala Ala
1               5                   10                  15

Phe Glu Arg Asp Val Glu Gly Gly Glu Arg Pro Thr Pro Gly Leu Leu
```

```
                20                  25                  30
Gly Leu Arg Ser Leu Ala Ser Ser Gly Arg Gly Trp Trp Ser Lys
             35                  40                  45
Thr Val Leu Trp Ala Val Phe Ala Val Val Leu Ile Glu Cys Ala Phe
 50                  55                  60
Ile Val Arg Leu Asp Ile Leu Asn Ser Pro Ser Ser Tyr Ser Ser
 65                  70                  75                  80
Ser Leu Asp Ser His Pro Glu Asn Pro Asn Lys Ile Ser Gly Gln Glu
                 85                  90                  95
Glu Leu Thr Ile Lys Thr Asn Lys Thr Ile Arg Ile Asp Lys Leu Pro
                100                 105                 110
Thr Gly Thr Asp Asp Val Cys Ser Ala Glu Trp Leu Glu Lys Val Asp
                115                 120                 125
Lys Val Thr Tyr Ser Arg Asp Phe Lys Lys Pro Val Leu Val Val
                130                 135                 140
Ser Gly Asn Glu Val Glu Asn Trp Asp Lys Cys Ser Val Pro Cys Val
145                 150                 155                 160
Phe Lys Ala His Gly Glu Gly Gln Ala Asp Ala Glu Phe Gly Tyr Gly
                165                 170                 175
Asp Ser Pro Ser Ala Leu Leu Val Leu Arg Ser Met Glu Ser Ser Ala
                180                 185                 190
Tyr Phe Pro Glu Asn Asp Ile Val Trp Ala Arg Ser Asn Gly Val Gly
                195                 200                 205
Val Val Met Thr Thr Ser Leu Ser Ser Asp Val Pro Glu Gly Tyr Phe
                210                 215                 220
Ser Trp Ala Glu Tyr Lys Ile Thr Asp Ala Pro Lys Pro Lys Thr Lys
225                 230                 235                 240
Pro Thr Leu Gly Ala Ala Phe Ile Ser Asn Cys Gly Ala His Asn Asp
                245                 250                 255
Arg Leu Thr Ile Met Arg Met Leu Pro Asn Glu Gly Val Arg Ile Asp
                260                 265                 270
Ser Tyr Gly Ser Cys Glu Pro Asn Val Leu Gly Gly Arg Ala Leu Asn
                275                 280                 285
Lys Leu Glu Thr Leu Arg Glu Tyr Lys Phe Ser Leu Ala Phe Glu Asn
                290                 295                 300
Ser Asn Val Glu Asp Tyr Val Thr Glu Lys Phe Phe Gln Ser Leu Val
305                 310                 315                 320
Ala Gly Ser Val Pro Ile Val Thr Gly Pro Pro Asn Ile Tyr Asp Phe
                325                 330                 335
Ala Pro Ala Ser Asn Ser Leu Val Tyr Ile Lys Asp Val Ser Glu Val
                340                 345                 350
Lys Ala Ala Ala Ser Pro Ile Lys Tyr Leu Ala Glu Asn Glu Thr Ala
                355                 360                 365
Tyr Asn Glu Thr Leu Gln Trp Lys Phe Asn Gly Pro Ser Asp Ser Phe
                370                 375                 380
Leu Ala Leu Val Asp Met Ala Ala Val His Ser Ser Cys Arg Leu Cys
385                 390                 395                 400
Ile Phe Val Ala Thr Lys Ser Arg Leu Lys Glu Glu Ala Ala Pro
                405                 410                 415
Lys Arg Pro Cys Lys Cys Thr Ser Lys Ser Gly Ser Thr Leu Tyr His
                420                 425                 430
Leu Tyr Val Arg Glu Arg Gly Arg Phe Glu Met Glu Ser Val Phe Ile
                435                 440                 445
```

```
Glu Gly Ser Lys Leu Ser Leu Ala His Leu Lys Gln Val Val Asp
    450                 455                 460

Lys Phe Thr Ala Leu Lys His Val Pro Ile Trp Lys Thr Glu Arg Pro
465                 470                 475                 480

Glu Val Ile Arg Gly Asn Ser Asp Leu Arg Ile Tyr Lys Ile Tyr Pro
                485                 490                 495

Val Gly Leu Thr Gln Arg Glu Ala Leu Tyr Thr Trp Asp Phe Gly Gly
                500                 505                 510

Asp Lys Gly Ile Lys Ala Met Val Gln Lys Gln Pro Cys Leu Gln Leu
                515                 520                 525

Glu Val Val Phe Val
    530

<210> SEQ ID NO 54
<211> LENGTH: 5626
<212> TYPE: DNA
<213> ORGANISM: Physcomitrella patens

<400> SEQUENCE: 54
ccatgcagtt taaccaaaca tttaggaagc aacatgatta gattagtcat ttttgttttc      60
ttaaatatca aatttgtgtt tcaaaaacta tgaagtacat taacaaatga actatctcaa    120
gagattatat taaaaatatt tgggatttaa gcctcagttt aataacccat ccaactattg    180
caatagtaag atggagtcac attagaatga ctaataaga ataaaaatcc aaaattcaaa    240
attcaaaatt caaaaaaaaa gcctttacga ttaaaatcat aaaataaact gaaaaaatga    300
aattatcatg ttttaaacaa aacatcaatt catatatact agaaaattat ttttgaaacc    360
aaaatcattc tatttattgc atcgattatt cttctttcaa caacacaaag ttttcaatgg    420
aagatcatat ccataattca ttacactaaa aaaagagatt aagtgagtgc taaaattgat    480
ctaatatata aatttaattt caagcctact ttatcatctt ataaagatta gttgagacat    540
tagaaagttt tggattttc tacccaagtt ggctttattt ttacttatat tcatatccac    600
tcgtttaatg tgcaaagaaa tatttttagc aacataaatg catacgaaaa caaaacaaac    660
acataaacaa acaaaactta ttaatacatg attttatcaa agaatgactt ttgtaccttt    720
caatgggaac aggaccatcg agaaagccaa gtggaaacag ggccgtcgag gcagcgtcca    780
cgtcagcgta tgattattcc gcggcatgcg aacgtggcat acatgacgtg gcgccggcga    840
agcttccgaa gggaatcgaa ctgcggtggg aacaagacct gacataagag tccacgtcag    900
ataattttaa tgctgccggt ggtgatgtgg cagggatgac atggcaccgg ctgagccagc    960
gatcgggttc gtctcgagcc ctactttctc cgctttcgtg caaaattcgt ttgccaggga   1020
gactcgatt acagaaacgg tccacatgat ccggccaggg aatcagttac cccttcacc    1080
cccttcggcg ttgcttgtgg atcatttcgt gattaacgcg agcactggct aggaatactg   1140
gtaaattttt ggcgcgctaa ctctctctat ctctctctgt gttgcgtttg atcaggggtt   1200
ttagggtttg ggtccagggt tccgaggagt atcgtcacgt gtattgcggt cttgttggag   1260
attcctcagt tgtgcatgta gatataaact tagtttagtc cacgatcggt ttctaatcgt   1320
ggattttgt gggtttcggt cgttgagcaa gaattttgtg aatttttgt attggggaa    1380
ggaaatgggg ttatggcgat atcgttttcg ttgggttcaa cgtgatcggt gagctccagg   1440
aagggctggt cactcacaat ccggtattcg tctcatcgag acgcattat cggttcatta   1500
tatgtatata tatatatata tatatatata tatgcagagt cgattgtgtt gcaatttctg   1560
```

```
aactaggtac tgttgaattg tagattgcct tcaagtagct ctcgatgttg gaatgacgga    1620
cacaaattct gctactgaat gagaccatat tctgcaccgt taattggttt tatgaatata    1680
tggtgtcgaa ttacattctg tctcgaatcc atgtgccctt tctgcacgaa cgttggtttg    1740
tagttgtagt gcagccagtg tgtttggttt aggattatgc tttgacgatc gatgagtccg    1800
tttcatggtt ttatacttgt catttatctt cttgtgattt tttgtttaca aatgttcccc    1860
caattgtaac gtgggacttt cgtgtgtggt ggttgctcaa attgatagtt ttggtcattt    1920
gatttgcgga gagcaatcgg tgtcatggaa aatcccttcg actgctttga tccaatcaaa    1980
gttctgcttg agccaatgtg agaggtggag gattgggctt cttctaagtg agggcttttcg   2040 attattgata tctcaaggcg aatgttgaag gcgcttaggg agtaaatatg aagggagata    2100
gggatacagg gcgatttcgc agggatgatg ctgcttttga acgggatgtg gaaggtggtg    2160
aaagacccac acccgggcta ttaggcttga ggtctctggc atctagctca ggacggggat    2220
ggtggagcaa aactgttttg tgggccgtat ttgctgttgt cctcattgaa tgcgctttca    2280
ttgttcgcct tgatatttg aattccccctt cttcatctta ctcgtcctct cttgattccc    2340
accccgagaa tcccaacaaa atctctggac aagaagaact aacgataaaa accaataaaa    2400
caattcggat tgacaagtta ccaacgggaa cagatgatgt ctgctcggca gaatggctag    2460
agaaggttga caaagttaca tactcgcgtg attttaagaa gaaacctgtg ctggttgtat    2520
cgggaaatga agttgaggtt tgtaactctc tccttctatt tccttttctc ttaagggact    2580
gttaagtggt atatgtaagg attctttgag gatcacttgg aatgtgttgc atgtgtgatg    2640
attcagatat aacctatcag tcaagccttt tggttaacat cctacctgcg gagcaacaga    2700
tattgaatct tcttgttcat ctccaagagc ttgtttatgt tgcagaattg ggataaatgt    2760
tctgtgccat gcgtgttcaa ggcccatggt gagggtcagg cagatgcaga gtttggctat    2820
ggagattcac cctcggcact actagtgtta cgctctatgg aatcttctgc ttattttcct    2880
gagaatgaca tcgtgtgggc gcgaaggtga gatacattac actcgacgtt cacaaagttc    2940
aattgccttg aggcatcttg cttaaatcat ggtttcgaaa caacttttcg ctttatcagt    3000
ccaggcatgt gatttcagct ttcttcgctt tgaagtactt ctagactgaa gttttgagtt    3060
aactaagaat cagttgatag cgccgacttt ccattctaac ctgaagagag ctcacagcaa    3120
cggagtgggg gtggtgatga ctacaagcct gtcatcggat gttccagagg gctacttttc    3180
gtgggcggag tacaaaatca cggatgctcc caagcccaag acaaaaccaa ctcttggagc    3240
tgcttttatt tccaactgtg gtgcgcataa tgatcgtctt accattatgc gaatgttacc    3300
aaacgaaggc gttcgaatag actcatacgg ttcttgcgaa caaaatgttc ttggaggccg    3360
aggtttgcct cgaactctct gcatgtcatg aaggagatct agaattttag aagcttttgt    3420
ccacgggcgt tttacattga tgcaaagtta ttttctgtc ttaatagccc tgattcatct    3480
tgcattgttt tgggaaggta gtcgcttcaa gtgtgaaatg ttggttggaa agaattcata    3540
ctcaaactta atgttggggt gagaggagaa atcatcatat tttctattga tatcttagag    3600
ttgtaattaa ctttgtgcag cattgaacaa gttggaaact cttcgagagt acaagtttag    3660
ccttgctttc gaaaattcca acgttgagga ttatgttacg gagaagttct ttcaatcctt    3720
agttgctggt acactcctca tatgtgcttt gatccttgat cagtatttgt ttacccaaat    3780
cacatgcgcg tacgcttttt atgcacgatg gaatataata tgattacttc tgctagttga    3840
cgtgtctttg tttcttcgga tggacaggct cagtccctat tgtaacggga cctccaaata    3900
tttatgactt cgcacccgca tcaaattctc ttgtatacat taaggacgtt agcgaagtaa    3960
```

-continued

```
aggctgcagc aagtcgcata aaatatctcg cagaaaacga gactgcgtac aacgagactt    4020
tgcagtaagt tcatctggac aatcatttgt gtttctaact caagaatcta tctcttacaa    4080
tctacaggtc ctgttttcta atttctttca ttcggtgaat atttatattt tcatgttagt    4140
caagcgttaa tctcattgac acattggagt gcattggtat tttcctatgt ttagttttaa    4200
tctgtgaggt aacttttca taagacttct tacgcttggg tccctttaag aaagcttttg    4260
ttaagtctca gtcctcagaa ttttgagtcc tggtccagtg tttcactctt atgtttgatc    4320
ctggaggctg tagtacgtag gtaccaatag ttttgtgatt ccgccttgc ctctagttat    4380 gaagggatat aataaattta gatcccttca gtacgaaagt gcatcgtcta cacatacagt    4440
taatagcgtt gtcgttgcgt gaattaagaa cagctgctca aaaattcttc tgcttccaat    4500
ctcttttagt tgtgatttcg cttaactctg aacatttccg caggtggaag tttaatggtc    4560
cttcagattc gtttctagct ctagtagaca tggctgccga gcactcctcc tgcaggttat    4620
gcatctttgt agctaccaaa tcgcgcctga agaagaagc ggctgctcct aaaagacctt    4680
gcaagtgcac cagcaaatct gggtccaccc tctaccattt atatgtacga gagcggggtc    4740
gtttcgaaat ggaatcggtt tttattgagt aagcattgat gccccactat tgaattcacg    4800
tcctttaatt cggctcatct tgtgatcgag gctgcaaaaa tatgattttg tttgttgtct    4860
ggacgtatgg gggtcttatt gtctacaaat atttcttccc tattctccta atgcctttga    4920
atgtttatat gcttacagag gatcgaaact ttccctagcc catttgaagc aagttgtagt    4980
agacaagttc acggccctca agcatggtcc tatttggaag acagagcggc ccggagttat    5040 taggggaac tcagaccttc ggatctacaa aatatatcct gtgggcctta ctcaacggga    5100
ggcactttat acttgggatt tcggtggtga aagggggtta aaggctatgg ttcaaaaaca    5160
accttgtctt caattggaag tagttttgt ttgatcccgt tttcatatca gtgtattatc    5220
atcagtgact gcatattgac acccaattct gatgatttt tatttttat tttttatttt    5280 ttttggtatg gttacatgct tttcagaggt ttctatgccg ctgagtattt tcctgaatcg    5340
cgaggtgtgg caggttatct gcgccgtcca cccaatattt tatgatgagt cgatgattcg    5400
tgagactaat ctagcttaac cttttcttta ctggcaagtc aaaattgagt ttaaatatt    5460 tcagtatcct gttagtaatt tcagacacat gtattctatg tctcatactc tttacgtgaa    5520
agttcaactg acttatattt tgtcgtttt ctgtagatca ctgttttagc gcatacaaag    5580
acaattgtct aaatatttt aaagaaggtg atatttatt ataaga             5626
```

<210> SEQ ID NO 55
<211> LENGTH: 533
<212> TYPE: PRT
<213> ORGANISM: Physcomitrella patens

<400> SEQUENCE: 55

```
Met Lys Gly Asp Arg Asp Thr Gly Arg Phe Arg Arg Asp Asp Ala Ala
1               5                   10                  15

Phe Glu Arg Asp Val Glu Gly Gly Glu Arg Pro Thr Pro Gly Leu Leu
            20                  25                  30

Gly Leu Arg Ser Leu Ala Ser Ser Ser Gly Arg Gly Trp Trp Ser Lys
        35                  40                  45

Thr Val Leu Trp Ala Val Phe Ala Val Val Leu Ile Glu Cys Ala Phe
    50                  55                  60

Ile Val Arg Leu Asp Ile Leu Asn Ser Pro Ser Ser Tyr Ser Ser
65                  70                  75                  80
```

-continued

```
Ser Leu Asp Ser His Pro Glu Asn Pro Asn Lys Ile Ser Gly Gln Glu
                85                  90                  95

Glu Leu Thr Ile Lys Thr Asn Lys Thr Ile Arg Ile Asp Lys Leu Pro
            100                 105                 110

Thr Gly Thr Asp Asp Val Cys Ser Ala Glu Trp Leu Gly Lys Val Asp
        115                 120                 125

Lys Val Thr Tyr Ser Arg Asp Phe Lys Lys Pro Val Leu Val Val
    130                 135                 140

Ser Gly Asn Glu Val Glu Asn Trp Asp Lys Cys Ser Val Pro Cys Val
145                 150                 155                 160

Phe Lys Ala His Gly Glu Gly Gln Ala Asp Ala Glu Phe Gly Tyr Gly
                165                 170                 175

Asp Ser Pro Ser Ala Leu Leu Val Leu Arg Ser Met Glu Ser Ser Ala
            180                 185                 190

Tyr Phe Pro Glu Asn Asp Ile Val Trp Ala Arg Ser Asn Gly Val Gly
        195                 200                 205

Val Val Met Thr Thr Ser Leu Ser Ser Asp Val Pro Glu Gly Tyr Phe
    210                 215                 220

Ser Trp Ala Glu Tyr Lys Ile Thr Asp Ala Pro Lys Pro Lys Thr Lys
225                 230                 235                 240

Pro Thr Leu Gly Ala Ala Phe Ile Ser Asn Cys Gly Ala His Asn Asp
                245                 250                 255

Arg Leu Thr Ile Met Arg Met Leu Pro Asn Glu Gly Val Arg Ile Asp
            260                 265                 270

Ser Tyr Gly Ser Cys Glu Gln Asn Val Leu Gly Gly Arg Ala Leu Asn
        275                 280                 285

Lys Leu Glu Thr Leu Arg Glu Tyr Lys Phe Ser Leu Ala Phe Glu Asn
    290                 295                 300

Ser Asn Val Glu Asp Tyr Val Thr Glu Lys Phe Phe Gln Ser Leu Val
305                 310                 315                 320

Ala Gly Ser Val Pro Ile Val Thr Gly Pro Pro Asn Ile Tyr Asp Phe
                325                 330                 335

Ala Pro Ala Ser Asn Ser Leu Val Tyr Ile Lys Asp Val Ser Glu Val
            340                 345                 350

Lys Ala Ala Ala Ser Arg Ile Lys Tyr Leu Ala Glu Asn Glu Thr Ala
        355                 360                 365

Tyr Asn Glu Thr Leu Gln Trp Lys Phe Asn Gly Pro Ser Asp Ser Phe
    370                 375                 380

Leu Ala Leu Val Asp Met Ala Ala Glu His Ser Ser Cys Arg Leu Cys
385                 390                 395                 400

Ile Phe Val Ala Thr Lys Ser Arg Leu Lys Glu Glu Ala Ala Ala Pro
                405                 410                 415

Lys Arg Pro Cys Lys Cys Thr Ser Lys Ser Gly Ser Thr Leu Tyr His
            420                 425                 430

Leu Tyr Val Arg Glu Arg Gly Arg Phe Glu Met Glu Ser Val Phe Ile
        435                 440                 445

Glu Gly Ser Lys Leu Ser Leu Ala His Leu Lys Gln Val Val Asp
    450                 455                 460

Lys Phe Thr Ala Leu Lys His Gly Pro Ile Trp Lys Thr Glu Arg Pro
465                 470                 475                 480

Gly Val Ile Arg Gly Asn Ser Asp Leu Arg Ile Tyr Lys Ile Tyr Pro
                485                 490                 495
```

```
Val Gly Leu Thr Gln Arg Glu Ala Leu Tyr Thr Trp Asp Phe Gly Gly
            500                 505                 510

Asp Lys Gly Leu Lys Ala Met Val Gln Lys Gln Pro Cys Leu Gln Leu
        515                 520                 525

Glu Val Val Phe Val
    530

<210> SEQ ID NO 56
<211> LENGTH: 658
<212> TYPE: DNA
<213> ORGANISM: Medicago truncatula
<220> FEATURE:
<221> NAME/KEY: misc_feature
<222> LOCATION: (584)..(584)
<223> OTHER INFORMATION: n is a, c, g, or t

<400> SEQUENCE: 56
tgagaacaat attgccatgg cacggcggag gggatatcac attgcaatga caaccagtct     60
atcatccgac gtccctgttg gatatttttc atgggctgag tatgcatcta tggcaccgat    120
aagcccaaaa actgaaaaag cttttgcagc tgcttttatt tccaattgtg gtgctcgaaa    180
tttccggttg caagctctcg aagccctgga aaaacaaac atctcgattg actcttatgg     240
tagttgtcat aggaatcgtg atggaagagt ggacaaactg gaaaccctga cgcgctacaa    300
atttagctta gcatttgaaa attctaacga ggaggattat gtaactgaaa agttttttcca   360 gtcgcttgtt gctggaacta tccctgtggt tgttggtcct ccaaatattc aagatttgc     420 tccttctcct ggttcatttt tatacatcaa agaactagag gatgttgagt ctgttgccaa    480
gtccatgaga tacctagcag aaaaccctga agcatataat caatcattga ggtggaagta    540
tgaagggcca tctgattcct tcaaggccct tgtggatatg gcanctgtac attcatcttg    600
ccgcctttgc attcacttgg cctcaaagag tagagagaag gaagagaaga gcccagat     658

<210> SEQ ID NO 57
<211> LENGTH: 219
<212> TYPE: PRT
<213> ORGANISM: Medicago truncatula
<220> FEATURE:
<221> NAME/KEY: misc_feature
<222> LOCATION: (195)..(195)
<223> OTHER INFORMATION: Xaa can be any naturally occurring amino acid

<400> SEQUENCE: 57

Glu Asn Asn Ile Ala Met Ala Arg Arg Gly Tyr His Ile Ala Met
1               5                   10                  15

Thr Thr Ser Leu Ser Ser Asp Val Pro Val Gly Tyr Phe Ser Trp Ala
            20                  25                  30

Glu Tyr Asp Ile Met Ala Pro Ile Ser Pro Lys Thr Glu Lys Ala Phe
        35                  40                  45

Ala Ala Ala Phe Ile Ser Asn Cys Gly Ala Arg Asn Phe Arg Leu Gln
    50                  55                  60

Ala Leu Glu Ala Leu Glu Lys Thr Asn Ile Ser Ile Asp Ser Tyr Gly
65                  70                  75                  80

Ser Cys His Arg Asn Arg Asp Gly Arg Val Asp Lys Leu Glu Thr Leu
                85                  90                  95

Thr Arg Tyr Lys Phe Ser Leu Ala Phe Glu Asn Ser Asn Glu Glu Asp
            100                 105                 110

Tyr Val Thr Glu Lys Phe Phe Gln Ser Leu Val Ala Gly Thr Ile Pro
        115                 120                 125
```

```
Val Val Val Gly Pro Pro Asn Ile Gln Asp Phe Ala Pro Ser Pro Gly
            130                 135                 140

Ser Phe Leu Tyr Ile Lys Glu Leu Glu Asp Val Glu Ser Val Ala Lys
145                 150                 155                 160

Ser Met Arg Tyr Leu Ala Glu Asn Pro Glu Ala Tyr Asn Gln Ser Leu
                165                 170                 175

Arg Trp Lys Tyr Glu Gly Pro Ser Asp Ser Phe Lys Ala Leu Val Asp
                180                 185                 190

Met Ala Xaa Val His Ser Ser Cys Arg Leu Cys Ile His Leu Ala Ser
                195                 200                 205

Lys Ser Arg Glu Lys Glu Glu Lys Ser Pro Asp
            210                 215

<210> SEQ ID NO 58
<211> LENGTH: 625
<212> TYPE: DNA
<213> ORGANISM: Arabidopsis thaliana

<400> SEQUENCE: 58
tcgtcttctt cttctccatc ttcatcaatc aagcgaaaat tatcgtattt gttaccactc      60
tgcgttgctc tggtagttat cgctgagatc gggtttctgg gtcggctcga taaagtcgct     120
ttggttgata cgttgactga tttcttcacc cagtctccgt cactctcgca gtctccaccg     180
gcgagatccg atcggaagaa gatcggatta tttactgata ggagctgcga ggagtggttg     240
atgagagaag attcagttac ttactctaga gattttacta agatccaat ttttatctct      300 ggtggtgaaa aggactttca atggtgttct gtggattgta catttggaga tagttcaggg     360
aaaacaccag atgctgcgtt tggattaggt cagaaacctg aactcttag tataatacgt      420 tccatggaat cagcacagta ttatccagaa aatgatcttg cacaggcacg acggagaggt     480
tatgatatag tgatgaccac tagtctatca tcagatgttc ctgttggata tttttcgtgg     540
gcggagtatg atattatgtc tccggtacag ccaaaaactg agagagctat tgcagctgct     600
tttatttcta attgtggtgc tcgga                                           625

<210> SEQ ID NO 59
<211> LENGTH: 208
<212> TYPE: PRT
<213> ORGANISM: Arabidopsis thaliana

<400> SEQUENCE: 59

Ser Ser Ser Ser Ser Pro Ser Ser Ile Lys Arg Lys Leu Ser Tyr
1               5                   10                  15

Leu Leu Pro Leu Cys Val Ala Leu Val Val Ile Ala Glu Ile Gly Phe
                20                  25                  30

Leu Gly Arg Leu Asp Lys Val Ala Leu Val Asp Thr Leu Thr Asp Phe
            35                  40                  45

Phe Thr Gln Ser Pro Ser Leu Ser Gln Ser Pro Ala Arg Ser Asp
        50                  55                  60

Arg Lys Lys Ile Gly Leu Phe Thr Asp Arg Ser Cys Glu Glu Trp Leu
65                  70                  75                  80

Met Arg Glu Asp Ser Val Thr Tyr Ser Arg Asp Phe Thr Lys Asp Pro
                85                  90                  95

Ile Phe Ile Ser Gly Gly Glu Lys Asp Phe Gln Trp Cys Ser Val Asp
                100                 105                 110

Cys Thr Phe Gly Asp Ser Ser Gly Lys Thr Pro Asp Ala Ala Phe Gly
            115                 120                 125
```

```
Leu Gly Gln Lys Pro Gly Thr Leu Ser Ile Ile Arg Ser Met Glu Ser
    130                 135                 140

Ala Gln Tyr Tyr Pro Glu Asn Asp Leu Ala Gln Ala Arg Arg Arg Gly
145                 150                 155                 160

Tyr Asp Ile Val Met Thr Thr Ser Leu Ser Ser Asp Val Pro Val Gly
                165                 170                 175

Tyr Phe Ser Trp Ala Glu Tyr Asp Ile Met Ser Pro Val Gln Pro Lys
            180                 185                 190

Thr Glu Arg Ala Ile Ala Ala Ala Phe Ile Ser Asn Cys Gly Ala Arg
        195                 200                 205
```

FUCOSYL TRANSFERASE GENE

This application is a continuation of application Ser. No. 11/808,097, filed Jun. 6, 2007, pending, which is a continuation-in-part of application Ser. No. 09/913,858, filed Aug. 20, 2001, abandoned, which is a 371 application of International Application No. PCT/AT00/00040, filed Feb. 17, 2000, which claims priority to A270/99, filed Feb. 18, 1999, all of which are incorporated herein by reference.

FIELD OF THE INVENTION

The invention relates to polynucleotides coding for a fucosyl transferase. Furthermore, the invention relates to partial sequences of these polynucleotides as well as to vectors comprising these polynucleotides, recombinant host cells, plants and insects transfected with the polynucleotides or with DNA derived therefrom, respectively, as well as to glycoproteins produced in these systems.

BACKGROUND OF THE INVENTION

Glycoproteins exhibit a variety and complexity of carbohydrate units, the composition and arrangement of the carbohydrates being characteristic of different organisms. The oligosaccharide units of the glycoproteins have a number of tasks, e.g. they are important in regulating metabolism, they are involved in transmitting cell-cell interactions, they determine the circulation periods of proteins in circulation, and they are decisive for recognizing epitopes in antigen-antibody reactions.

The glycosylation of glycoproteins starts in the endo-plasmatic reticulum (ER), where the oligosaccharides are either bound to asparagine side chains by N-glycosidic bonds or to serine or threonine side chains by O-glycosidic bonds. The N-bound oligosaccharides contain a common core from a pentasaccharide unit which consists of three mannose and two N-acetyl glucose amine residues. To further modify the carbohydrate units, the proteins are transported from the ER to the Golgi complex. The structure of the N-bound oligosaccharide units of glycoproteins is determined by their conformation and by the composition of the glycosyl transferases of the Golgi compartments in which they are processed.

It has been shown that the core pentasaccharide unit in the Golgi complex of some plant and insect cells is substituted by xylose and α1,3-bound fucose (P. Lerouge et al., 1998, Plant Mol. Biol. 38, 31-48; Rayon et al., 1998, L. Exp. Bot. 49, 1463-1472). The heptasaccharide "MMXF$^3$" forming constitutes the main oligosaccharide type in plants (Kurosaka et al., 1991, J. Biol. Chem., 266, 4168-4172). Thus, e.g., the horseradish peroxidase, carrot β-fructosidase and Erythrina cristagalli comprise lectin as well as the honeybee venom phospholipase A2 or the neuronal membrane glycoproteins from insect embryos α1,3-fucose residues which are bound to the glycan core. These structures are also termed complex N-glycans or mannose-deficient or truncated N-glycans, respectively. The α-mannosyl residues may be further replaced by GlcNAc, to which galactose and fucose are bound so that a structure is prepared which corresponds to the human Lewis a-epitope (Melo et al., 1997, FEBS Lett 415, 186-191; Fitchette-Laine et al., 1997, Plant J. 12, 1411-1417).

Neither xylose nor the α1,3-bound fucose exist in mammalian glycoproteins. It has been found that the core-α1,3-fucose plays an important role in the epitope recognition by antibodies which are directed against plant and insect N-bound oligosaccharides (I. B. H. Wilson et al., Glycobiology Vol. 8, No. 7, pp. 651-661, 1998), and thereby trigger immune reactions in human or animal bodies against these oligosaccharides. The α1,3-fucose residue furthermore seems to be one of the main causes for the wide-spread allergic cross reactivity between various plant and insect allergens (Tretter et al., Int. Arch. Allergy Immunol. 1993; 102:259-266) and is also termed "cross-reactive carbohydrate determinant" (CCD). In a study of epitopes of tomatoes and grass pollen, also α1,3-bound fucose residues were found as a common determinant, which seems to be the reason why tomato and grass pollen allergies frequently occur together in patients (Petersen et al., 1996, J. Allergy Clin. Immunol., Vol. 98, 4; 805-814). Due to the frequent occurrence of immunological cross reactions, the CCDs moreover mask allergy diagnoses.

The immunological reactions triggered in the human body by plant proteins are the main problem in the medicinal use of recombinant human proteins produced in plants. To circumvent this problem, α1,3-core-fucosylation would have to be prevented. In a study it could be demonstrated that oligosaccharides comprising an L-galactose instead of an L-fucose (6-deoxy-L-galactose) nevertheless are biologically fully active (E. Zablackis et al., 1996, Science, Vol. 272). According to another study, a mutant of the plant Arabidopsis thaliana was isolated in which the N-acetyl-glucosaminyl transferase I, the first enzyme in the biosynthesis of complex glycans, is missing. The biosynthesis of the complex glycoproteins in this mutant thus is disturbed. Nevertheless, these mutant plants are capable of developing normally under certain conditions (A. Schaewen et al, 1993, Plant Physiol. 102; 1109-1118).

To purposefully block the binding of the core-α1,3-fucose in an oligosaccharide without also interfering in other glycosylation steps, merely that enzyme would have to be inactivated which is directly responsible for this specific glycosylation, i.e. the core-α1,3-fucosyl transferase. It has been isolated and characterized for the first time from mung beans, and it has been found that the activity of this enzyme depends on the presence of non-reducing GlcNAc ends (Staudacher et al., 1995, Glycoconjugate J. 12, 780-786). This transferase which only occurs in plants and insect, yet not in human beings or in other vertebrates, would have to be inactivated on purpose or suppressed so that human proteins which are produced in plants or in plant cells or also in insects or in insect cells, respectively, do no longer comprise this immune-reaction-triggering epitope, as has been the case so far.

The publication by John M. Burke "Clearing the way for ribozymes" (Nature Biotechnology 15:414-415; 1997) relates to the general mode of function of ribozymes.

The publication by Pooga et al., "Cell penetrating PNA constructs regulate galanin receptor levels and modify pain transmission in vivo" (Nature Biotechnology 16:857-861; 1998) relates to PNA molecules in general and specifically to a PNA molecule that is complementary to human galanin receptor type 1 mRNA.

U.S. Pat. No. 5,272,066 A relates to a method of changing eukaryotic and prokaryotic proteins to prolongue their circulation in vivo. In this instance, the bound oligosaccharides are changed with the help of various enzymes, among them also GlcNAc-α1→3(4)-fucosyl transferase.

EP 0 643 132 A1 relates to the cloning of an α1,3-fucosyl transferase isolated from human cells (THP-1). The carbohydrate chains described in this publication correspond to human sialyl Lewis x- and sialyl Lewis a-oligosaccharides. The specificity of the enzyme from human cells is quite different than that of fucosyltransferase from plant cells.

DESCRIPTION OF THE INVENTION

It is an object of the present invention to clone and to sequence the gene which codes for a plant fucosyl transferase, and to prepare vectors comprising this gene, DNA fragments thereof or an altered DNA or a DNA derived therefrom, to transfect plants and insects as well as cells thereof with one of these vectors, to produce glycoproteins that do not comprise the normally occurring α1,3-core-fucose, as well as to provide corresponding methods therefor.

The object according to the invention is achieved by a DNA molecule comprising a sequence according to SEQ ID NO: 1 (in this disclosure also the IUPAC code has been used, "N" meaning inosin) with an open reading frame from base pair 211 to base pair 1740 or being at least 50% homologous to the above sequence or hybridizing with the above-indicated sequence under stringent conditions, or comprising a sequence which has degenerated to the above DNA sequence due to the genetic code, the sequence coding for a plant protein which has fucosyl transferase activity or is complementary thereto.

This sequence which has not been described before can be perfectly used for any experiments, analysis and methods for production etc. which relate to the plant fucosyl transferase activity. Here the DNA sequence as well as the protein coded by this sequence are of interest. However, in particular the DNA sequence will be used for the inhibition of the fucosyl transferase activity.

The open reading frame of the SEQ ID NO: 1 codes for a protein with 510 amino acids and with a theoretical molecular weight of 56.8 kDa, a transmembrane portion presumably being present in the region between Asn36 and Gly54. The calculated pI value of the encoded protein of the sequence according to SEQ ID NO: 1 is 7.51.

Additional fucosyl transferase sequences are shown in SEQ ID NOS: 18-59.

The activity of the plant fucosyl transferase is detected by a method and measured, the fucosyl transferase being added to a sample comprising labelled fucose and an acceptor (e.g. a glycoprotein) bound to a carrier, e.g. Sepharose. After the reaction time, the sample is washed, and the content of bound fucose is measured. The activity of the fucosyl transferase in this case is seen as positive if the activity measurement is higher by at least 10 to 20%, in particular at least 30 to 50%, than the activity measurement of the negative control. The structure of the glycoprotein may additionally be verified by means of HPLC. Such protocols are prior art (Staudacher et al. 1998, Anal. Biochem. 246, 96-101; Staudacher et al. 1991, Eur. J. Biochem. 199, 745-751).

For example, fucosyl transferase is admixed to a sample comprising radioactively labelled fucose and an acceptor, e.g. GlcNAcβ1-2Manα1-3(GlcNAβ1-2Manα1-6)Manβ1-4GlcNAcβ1-4GlcNAcβ1-Asn. After the reaction time, the sample is purified by anion exchange chromatography, and the content of bound fucose is measured. From the difference of the measured radioactivity of the sample with acceptor and that of a negative control without acceptor, the activity can be calculated. The activity of the fucosyl transferase is already evaluated as positive if the radioactivity measured is at least 30-40% higher than the measured radioactivity of the negative sample.

The pairing of two DNA molecules can be changed by selection of the temperature and ionic strength of the sample. By stringent conditions, according to the invention conditions are understood which allow for an exact, stringent, binding. For instance, the DNA molecules are hybridized in 7% sodium dodecyl sulfate (SDS), 0.5M NaPO4, pH 7.0, 1 mM EDTA at 50° C., and washed with 1% SDS at 42° C.

Whether sequences have an at least 50% homology to SEQ ID NO: 1 can be determined e.g. by means of the program FastDB of EMBL or SWISSPROT data bank.

Preferably, the sequence of the DNA molecule of the invention encodes a protein with a GlcNAc-α1,3-fucosyl transferase activity, in particular with a core-α1,3-fucosyl transferase activity.

As described above the core of α1,3-fucosyl transferase is present in plants and insects, however, not in the human body, so that in particular this DNA sequence is useful in analysis and experiments as well as methods for production which are fucosyl transferase specific.

By a core-α1,3-fucosyl transferase, in particular GDP-L-Fuc:Asn-bound GlcNAc-α1,3-fucosyl transferase is understood. Within the scope of the present invention, the term α1,3-fucosyl transferase as a rule particularly means core-α1,3 fucosyl transferase. For the above-described activity measurement, in particular acceptors having a non-reducing GlcNAc terminus are used. Such acceptors are, e.g., GlcNAcβ1-2Manα1-3(GlcNAβ1-2Manα1-6)Manβ1-4GlcNAcβ1-4GlcNAcβ1-Asn, GlcNAcβ1-2Manα1-3 (GlcNAcβ1-2Manα1-6)Manβ1-4GlcNAcβ1-4(Fucα1-6) GlcNAcβ1-Asn and GlcNAcβ1-2Manα1-3[Manα1-3 (Manα1-6)Manα1-6]Manβ1-4GlcNAcβ1-4GlcNAcβ1-Asn. Whether the fucose is bound or not can furthermore be determined by measuring the insensitivity relative to N-glycosidase F, which can be detected by means of mass spectrometry.

Preferably, the DNA molecule according to the invention comprises at least 70-80%, particularly preferred at least 95%, homology to the sequence according to SEQ ID NO: 1. This sequence codes for a particularly active GlcNAc-α1,3-fucosyl transferase.

Since the DNA sequence can be more or less changed according to the plant or the insect a sequence which shows, for example, 70% homology to a sequence according to SEQ ID No 1 has also a fucosyl transferase activity which is sufficient in order to be used in analysis, experiments or methods of production as above described.

According to a further advantageous embodiment, the DNA molecule comprises 2150 to 2250, in particular 2198, base pairs. This DNA molecule comprises 100 to 300, preferably 210, base pairs upstream in front of the start codon, as well as 350 to 440, in particular 458, base pairs downstream after the stop codon of the open reading frame, wherein the end of the DNA molecule preferably comprises a 3'-poly(A)-tail. In this manner, a faultless regulation on translation level is ensured and a DNA molecule is provided which is particularly efficient and unproblematic for the coding of an active GlcNAc-α1,3-fucosyl transferase.

The present invention moreover relates to a DNA molecule which comprises a sequence according to SEQ ID NO: 3 or comprising a sequence having at least 85%, particularly preferred at least 95%, in particular at least 99%, homology to the above-identified sequence or which, under stringent conditions, hybridizes with the above-indicated sequence or which has degenerated to the above-indicated DNA sequence due to the genetic code. The homology preferably is determined with a program which recognizes insertions and deletions and which does not consider these in the homology calculation. This nucleotide sequence codes for a conserved peptide motif, which means that the plurality of the active and functioning GlcNAc-α1,3-fucosyl transferases comprises the amino acid sequence encoded thereby. In this instance, the sequence may either have the same size as the sequence according to SEQ ID NO: 3, or, of course, it may also be larger. This sequence has a smaller length than the sequence which codes the complete protein and is therefore less sensitive with respect to recombination, deletion, or any other mutations. Due to the conservative motif and its higher stability this sequence is particularly advantageous for sequence recognising test.

SEQ ID NO: 3 comprises the following sequence:

```
5'-GAAGCCCTGAAGCACTACAAATTTAGCTTAGCGTTTGAAAATTCGAA

TGAGGAAGATTATGTAACTGAAAAATTCTTCCAATCCCTTGTTGCTGGAA

CTGTCCCT-3'
```

In a further aspect, the present invention relates to a DNA molecule which comprises a partial sequence of one of the above-indicated DNA molecules and has a size of from 20 to 200, preferably from 30 to 50, base pairs. The DNA molecule may, e.g., be utilized to bind, as a probe, to complementary sequences of GlcNAc-α1,3-fucosyl transferases so that they can be selected from a sample. In this manner, further GlcNAc-α1,3-fucosyl transferases from the most varying plants and insects can be selected, isolated and characterized. Any desired one or also several different partial sequences may be used, in particular a part of the conserved motif already described above.

In doing so, it is particularly advantageous if one of the above-indicated DNA molecules is covalently associated with a detectable labelling substance. As the labelling substance, any common marker can be used, such as, e.g., fluorescent, luminescent, radioactive markers, non-isotopic markers, such as biotin, etc. In this manner, reagents are provided which are suitable for the detection, selection and quantitation of corresponding DNA molecules in solid tissue samples (e.g. from plants) or also in liquid samples, by means of hybridizing methods.

A further aspect of the invention relates to a biologically functional vector which comprises one of the above-indicated DNA molecules or parts thereof of differing lengths with at least 20 base pairs. For transfection into host cells, an independent vector capable of amplification is necessary, wherein, depending on the host cell, transfection mechanism, task and size of the DNA molecule, a suitable vector can be used. Since a large number of different vectors is known, an enumeration thereof would go beyond the limits of the present application and therefore is done without here, particularly since the vectors are very well known to the skilled artisan (as regards the vectors as well as all the techniques and terms used in this specification which are known to the skilled artisan, cf. also Sambrook Maniatis). Ideally, the vector has a small molecule mass and should comprise selectable genes so as to lead to an easily recognizable phenotype in a cell so thus enable an easy selection of vector-containing and vector-free host cells. To obtain a high yield of DNA and corresponding gene products, the vector should comprise a strong promoter, as well as an enhancer, gene amplification signals and regulator sequences. For an autonomous replication of the vector, furthermore, a replication origin is important. Polyadenylation sites are responsible for correct processing of the mRNA and splice signals for the RNA transcripts. If phages, viruses or virus particles are used as the vectors, packaging signals will control the packaging of the vector DNA. For instance, for transcription in plants, Ti plasmids are suitable, and for transcription in insect cells, baculoviruses, and in insects, respectively, transposons, such as the P element.

If the above-described inventive vector is inserted into a plant or into a plant cell, a post-transcriptional suppression of the gene expression of the endogenous α1,3-fucosyl transferase gene is attained by transcription of a transgene homologous thereto or of parts thereof, in sense orientation. For this sense technique, furthermore, reference is made to the publications by Baucombe 1996, Plant. Mol. Biol., 9:373-382, and Brigneti et al., 1998, EMBO J. 17:6739-6746. This strategy of "gene silencing" is an effective way of suppressing the expression of the α1,3-fucosyl transferase gene, cf. also Waterhouse et al., 1998, Proc. Natl. Acad. Sci. USA, 95:13959-13964.

Furthermore, the invention relates to a biologically functional vector comprising a DNA molecule according to one of the above-described embodiments, or parts thereof of differing lengths in reverse orientation to the promoter. If this vector is transfected in a host cell, an "antisense mRNA" will be read which is complementary to the mRNA of the GlcNAc-α1,3-fucosyl transferase and complexes the latter. This bond will either hinder correct processing, transportation, stability or, by preventing ribosome annealing, it will hinder translation and thus the normal gene expression of the GlcNAc-α1,3-fucosyl transferase.

Although the entire sequence of the DNA molecule could be inserted into the vector, partial sequences thereof because of their smaller size may be advantageous for certain purposes. With the antisense aspect, e.g., it is important that the DNA molecule is large enough to form a sufficiently large antisense mRNA which will bind to the transferase mRNA. A suitable antisense RNA molecule comprises, e.g., from 50 to 200 nucleotides since many of the known, naturally occurring antisense RNA molecules comprise approximately 100 nucleotides.

For a particularly effective inhibition of the expression of an active α1,3-fucosyl transferase, a combination of the sense technique and the antisense technique is suitable (Waterhouse et al., 1998, Proc. Natl. Acad. Sci., USA, 95:13959-13964).

Advantageously, rapidly hybridizing RNA molecules are used. The efficiency of antisense RNA molecules which have a size of more than 50 nucleotides will depend on the annealing kinetics in vitro. Thus, e.g., rapidly annealing antisense RNA molecules exhibit a greater inhibition of protein expression than slowly hybridizing RNA molecules (Wagner et al., 1994, Annu. Rev. Microbiol., 48:713-742; Rittner et al., 1993, Nucl. Acids Res., 21:1381-1387). Such rapidly hybridizing antisense RNA molecules particularly comprise a large number of external bases (free ends and connecting sequences), a large number of structural subdomains (components) as well as a low degree of loops (Patzel et al. 1998; Nature Biotechnology, 16; 64-68). The hypothetical secondary structures of the antisense RNA molecule may, e.g., be determined by aid of a computer program, according to which a suitable antisense RNA DNA sequence is chosen.

Different sequence regions of the DNA molecule may be inserted into the vector. One possibility consists, e.g., in inserting into the vector only that part which is responsible for ribosome annealing. Blocking in this region of the mRNA will suffice to stop the entire translation. A particularly high efficiency of the antisense molecules also results for the 5'- and 3'-nontranslated regions of the gene.

Preferably, the DNA molecule according to the invention includes a sequence which comprises a deletion, insertion and/or substitution mutation. The number of mutant nucleotides is variable and varies from a single one to several deleted, inserted or substituted nucleotides. It is also possible that the reading frame is shifted by the mutation. In such a "knock-out gene" it is merely important that the expression of a GlcNAc-α1,3-fucosyl transferase is disturbed, and the formation of an active, functional enzyme is prevented. In doing so, the site of the mutation is variable, as long as expression of an enzymatically active protein is prevented. Preferably, the mutation in the catalytic region of the enzyme which is located in the C-terminal region. The method of inserting mutations in DNA sequences are well known to the skilled artisan, and therefore the various possibilities of mutageneses need not be discussed here in detail. Coincidental mutageneses as well as, in particular, directed mutageneses, e.g. the site-directed mutagenesis, oligonucleotide-controlled mutagenesis or mutageneses by aid of restriction enzymes may be employed in this instance.

The invention further provides a DNA molecule which codes for a ribozyme which comprises two sequence portions of at least 10 to 15 base pairs each, which are complementary to sequence portions of an inventive DNA molecule as described above so that the ribozyme complexes and cleaves the mRNA which is transcribed from a natural GlcNAc-α1,3-fucosyl transferase DNA molecule. The ribozyme will recognized the mRNA of the GlcNAc-α1,3-fucosyl transferase by complementary base pairing with the mRNA. Subsequently, the ribozyme will cleave and destroy the RNA in a sequence-specific manner, before the enzyme is translated. After dissociation from the cleaved substrate, the ribozyme will repeatedly hybridize with RNA molecules and act as specific endonuclease. In general, ribozymes may specifically be produced for inactivation of a certain mRNA, even if not the entire DNA sequence which codes for the protein is known. Ribozymes are particularly efficient if the ribosomes move slowly along the mRNA. In that case it is easier for the ribozyme to find a ribosome-free site on the mRNA. For this reason, slow ribosome mutants are also suitable as a system for ribozymes (J. Burke, 1997, Nature Biotechnology; 15, 414-415). This DNA molecule is particularly advantageous for the downregulation and inhibition, respectively, of the expression of plant GlcNAc-α1,3-fucosyl transferases.

One possible way is also to use a varied form of a ribozmye, i.e. a minizyme. Minizymes are efficient particularly for cleaving larger mRNA molecules. A minizyme is a hammer head ribozyme which has a short oligonucleotide linker instead of the stem/loop II. Dimer-minizymes are particularly efficient (Kuwabara et al., 1998, Nature Biotechnology, 16; 961-965). Consequently, the invention also relates to a biologically functional vector which comprises one of the two last-mentioned DNA molecules (mutation or ribozyme-DNA molecule). What has been said above regarding vectors also applies in this instance. Such a vector can be, for example, inserted into a microorganism and can be used for the production of high concentrations of the above described DNA molecules. Furthermore such a vector is particularly good for the insertion of a specific DNA molecule into a plant or an insect organism in order to downregulate or completely inhibit the GlcNAc-α1,3-fucosyl transferase production in this organism.

According to the invention, there is provided a method of preparing a cDNA comprising the DNA molecule of the invention, wherein RNA is isolted from an insect or plant cell, in particular from hypokotyl cells, by means of which a reverse transcription is carried out after having admixed a reverse transcriptase and primers. The individual steps of this method are carried out according to protocols known per se. For the reverse transcription, on the one hand, it is possible to produce the cDNA of the entire mRNA with the help of oligo(dT) primers, and only then to carry out a PCR by means of selected primers so as to prepare DNA molecules comprising the GlcNAc-α1,3-fucosyl transferase gene. On the other hand, the selected primers may directly be used for the reverse transcription so as to obtain short, specific cDNA. The suitable primers may be prepared e.g. synthetically according to the pattern of cDNA sequences of the transferase. With the help of this method big quantities of the inventive cDNA molecules can be produced quickly in a simple way and with few mistakes.

The invention furthermore relates to a method of cloning a GlcNAc-α1,3-fucosyl transferase, characterized in that the DNA molecule of the invention is cloned into a vector which subsequently is transfected into a host cell or host, respectively, wherein, by selection and amplification of transfected host cells, cell lines are obtained which express the active GlcNac-α1,3-fucosyl transferase. The DNA molecule is inserted into the vector by aid of restriction endonucleases, e.g. For the vector, there applies what has already been said above. What is important in this method is that an efficient host-vector system is chosen. To obtain an active enzyme, eukaryotic host cells are particularly suitable. One possible way is to transfect the vector in insect cells. In doing so, in particular an insect virus would have to be used as vector, such as, e.g., baculovirus.

Of course, human or other vertebrate cells can also be transfected, in which case the latter would express an enzyme foreign to them.

Preferably, a method of preparing recombinant host cells, in particular plant or insect cells, or plants or insects, respectively, with a suppressed or completely stopped GlcNac-α1,3-fucosyl transferase production is provided, which is characterized in that at least one of the vectors according to the invention, i.e. that one comprising the inventive DNA molecule, the mutant DNA molecule or the DNA molecule coding for ribozymes or the one comprising the DNA molecule in inverse orientation to the promoter, is inserted into the host cell or plant or into the insect. What has been said above for the transfection also is applicable in this case.

As the host cells, plant cells may, e.g., be used, wherein, e.g., the Ti plasmid with the agrobacterium system is eligible. With the agrobacterium system it is possible to transfect a plant directly: agrobacteria cause root stem galls inplants. If agrobacteria infect an injured plant, the bacteria themselves do not get into the plant, but they insert the recombinant DNA portion, the so-called T-DNA, from the annular, extra chromosomal, tumour-inducing Ti-plasmid into the plant cells. The T-DNA, and thus also the DNA molecule inserted therein, are installed in the chromosomal DNA of the cell in a stable manner so that the genes of the T-DNA will be expressed in the plant. There exist numerous known, efficient transfection mechanisms for different host systems. Some examples are electroporation, the calcium phosphate method, microinjection, liposome method.

Subsequently, the transfected cells are selected, e.g. on the basis of antibiotic resistences for which the vector comprises genes, or other marker genes. Then the transfected cell lines are amplified, either in small amounts, e.g. in Petri dishes, or in large amounts, e.g. in fermentors. Furthermore, plants have a particular characteristic, i.e. they are capable to re-develop from one (transfected) cell or from a protoplast, respectively, to a complete plant which can be grown.

Depending on the vector used, processes will occur in the host so that the enzyme expression will be suppressed or completely blocked:

If the vector comprising the DNA molecule with the deletion, insertion or substitution mutation is transfected, a homologous recombination will occur: the mutant DNA molecule will recognize the identical sequence in the genome of the host cell despite its mutation and will be inserted exactly on that place so that a "knock-out gene" is formed. In this manner, a mutation is introduced into the gene for the GlcNAc-α1,3-fucosyl transferase which is capable of inhibiting the faultless expression of the GlcNAc-α1,3-fucosyl transferase. As has been explained above, with this technique it is important that the mutation suffices to block the expression of the active protein. After selection and amplification, the gene may be sequenced as an additional check so as to determine the success of the homologous recombination or the degree of mutation, respectively.

If the vector comprising the DNA molecule coding for a ribozyme is transfected, the active ribozyme will be expressed in the host cell. The ribozyme complexes the complementary mRNA sequence of the GlcNAc-$\alpha$1,3-fucosyl transferase at least at a certain site, cleaves this site, and in this manner it can inhibit the translation of the enzyme. In this host cell as well as in cell lines, or optionally, plant, respectively, derived therefrom, GlcNAc-$\alpha$1,3-fucosyl transferase will not be expressed.

In case the vector comprises the inventive DNA molecule in sense or inverse direction to the promoter, a sense or antisense-mRNA will be expressed in the transfected cell (or plant, respectively). The antisense mRNA is complementary at least to a part of the mRNA sequence of the GlcNAc-$\alpha$1,3-fucosyl transferase and may likewise inhibit translation of the enzyme. As an example of a method of suppressing the expression of a gene by antisense technique, reference is made to the publication by Smith et al., 1990, Mol. Gen. Genet. 224:477-481, wherein in this publication the expression of a gene involved in the maturing process of tomatoes is inhibited.

In all the systems, expression of the GlcNAc-$\alpha$1,3-fucosyl transferase is at least suppressed, preferably even completely blocked. The degree of the disturbance of the gene expression will depend on the degree of complexing, homologous recombination, on possible subsequent coincidental mutations and on other processes in the region of the genome. The transfected cells are checked for GlcNac-$\alpha$1,3-fucosyl transferase activity and selected.

Moreover, it is possible to still further increase the above-described suppression of the expression of the $\alpha$1,3-fucosyl transferase by introducing into the host a vector comprising a gene coding for a mammalian protein, e.g. $\beta$1,4-galactosyl transferase, in addition to the insertion of an above-described vector. Fucosylation may be reduced by the action of other mammalian enzymes, the combination of the inhibition of the expression of an active $\alpha$1,3-fucosyl transferase by means of the inventive vector and by means of a mammalian enzyme vector being particularly efficient.

Any type of plant may be used for transfection, e.g. mung bean, tobacco plant, tomato and/or potato plant. Another advantageous method of producing recombinant host cells, in particular plant or insect cells, or plants or insects, respectively, consists in that the DNA molecule comprising the mutation is inserted into the genome of the host cell, or plant or insect, respectively, in the place of the non-mutant homologous sequence (Schaefer et al., 1997, Plant J.; 11(6):1195-1206). This method thus does not function with a vector, but with a pure DNA molecule. The DNA molecule is inserted into the host e.g. by gene bombardment, microinjection or electroporation, to mention just three examples. As has already been explained, the DNA molecule binds to the homologous sequence in the genome of the host so that a homologous recombination and thus reception of the deletion, insertion or substitution mutation, respectively, will result in the genome: Expression of the GlcNAc-$\alpha$1,3-fucosyl transferase can be suppressed or completely blocked, respectively.

A further aspect of the invention relates to plants or plant cells, respectively, as well as insect or insect cells, respectively, their GlcNAc-$\alpha$1,3-fucosyl transferase activity being less than 50%, in particular less than 20%, particularly preferred 0%, of the GlcNAc-$\alpha$1,3-fucosyl transferase activity occurring in natural plants or plant cells, respectively, and insects or insect cells, respectively. The advantage of these plants or plant cells, respectively, is that the glycoproteins produced by them do not comprise any or hardly comprise any $\alpha$1,3-bound fucose. If products of these plants or insects, respectively, are taken up by human or vertebrate bodies, there will be no immune reaction to the $\alpha$1,3-fucose epitope.

Preferably, recombinant plants or plant cells, respectively, are provided which have been prepared by one of the methods described above, their GlcNAc-$\alpha$1,3-fucosyl transferase production being suppressed or completely blocked, respectively.

The invention also relates to recombinant insects or insect cells, respectively, which have been prepared by one of the methods described above and whose GlcNAc-$\alpha$1,3-fucosyl transferase production is suppressed or completely blocked, respectively. Also in this instance, no glycoproteins having $\alpha$1,3-bound fucose residues are produced so that likewise no immune reaction to the $\alpha$1,3-fucose epitope will occur.

The invention also relates to a PNA molecule comprising a base sequence complementary to the sequence of the DNA molecule according to the invention as well as partial sequences thereof. PNA (peptide nucleic acid) is a DNA-like sequence, the nucleobases being bound to a pseudo-peptide backbone. PNA generally hybridizes with complementary DNA-, RNA- or PNA-oligomers by Watson-Crick base pairing and helix formation. The peptide backbone ensures a greater resistance to enzymatic degradation. The PNA molecule thus is an improved antisense agent. Neither nucleases nor proteases are capable of attacking a PNA molecule. The stability of the PNA molecule, if bound to a complementary sequence, comprises a sufficient steric blocking of DNA and RNA polymerases, reverse transcriptase, telomerase and ribosomes.

If the PNA molecule comprises the above-mentioned sequence, it will bind to the DNA or to a site of the DNA, respectively, which codes for GlcNAc-$\alpha$1,3-fucosyl transferase and in this way is capable of inhibiting transcription of this enzyme. As it is neither transcribed nor translated, the PNA molecule will be prepared synthetically, e.g. by aid of the the t-Boc technique.

Advantageously, a PNA molecule is provided which comprises a base sequence which corresponds to the sequence of the inventive DNA molecule as well as partial sequences thereof. This PNA molecule will complex the mRNA or a site of the mRNA of GlcNAc-$\alpha$1,2-fucosyl transferase so that the translation of the enzyme will be inhibited. Similar arguments as set forth for the antisense RNA apply in this case. Thus, e.g., a particularly efficient complexing region is the translation start region or also the 5'-non-translated regions of mRNA.

A further aspect of the present invention relates to a method of preparing plants or insects, or cells, respectively, in particular plant or insect cells which comprise a blocked expression of the GlcNAc-$\alpha$1,3-fucosyl transferase on transcription or translation level, respectively, which is characterized in that inventive PNA molecules are inserted in the cells. To insert the PNA molecule or the PNA molecules, respectively, in the cell, again conventional methods, such as, e.g., electroporation or microinjection, are used. Particularly efficient is insertion if the PNA oligomers are bound to cell penetration peptides, e.g. transportan or pAntp (Pooga et al., 1998, Nature Biotechnology, 16; 857-861).

The invention provides a method of preparing recombinant glycoproteins which is characterized in that the inventive, recombinant plants or plant cells, respectively, as well as recombinant insects or insect cells, respectively, whose GlcNAc-α1,3-fucosyl transferase production is suppressed or completely blocked, respectively, or plants or insects, or cells, respectively, in which the PNA molecules have been inserted according to the method of the invention, are transfected with the gene that expresses the glycoprotein so that the recombinant glycoproteins are expressed. In doing so, as has already been described above, vectors comprising genes for the desired proteins are transfected into the host or host cells, respectively, as has also already been described above. The transfected plant or insect cells will express the desired proteins, and they have no or hardly any α1,3-bound fucose. Thus, they do not trigger the immune reactions already mentioned above in the human or vertebrate body. Any proteins may be produced in these systems.

Advantageously, a method of preparing recombinant human glycoproteins is provided which is characterized in that the recombinant plants or plant cells, respectively, as well as recombinant insects or insect cells, respectively, whose GlcNAc-α1,3-fucosyl transferase production is suppressed or completely blocked, or plants or insects, or cells, respectively, in which PNA molecules have been inserted according to the method of the invention, are transfected with the gene that expresses the glycoprotein so that the recombinant glycoproteins are expressed. By this method it becomes possible to produce human proteins in plants (plant cells) which, if taken up by the human body, do not trigger any immune reaction directed against α1,3-bound fucose residues. There, it is possible to utilize plant types for producing the recombinant glycoproteins which serve as food stuffs, e.g. banana, potato and/or tomato. The tissues of this plant comprise the recombinant glycoprotein so that, e.g. by extraction of the recombinant glycoprotein from the tissue and subsequent administration, or directly by eating the plant tissue, respectively, the recombinant glycoprotein is taken up in the human body.

Preferably, a method of preparing recombinant human glycoproteins for medical use is provided, wherein the inventive, recombinant plants or plant cells, respectively, as well as recombinant insects or insect cells, respectively, whose GlcNAc-α1,3-fucosyl transferase production is suppressed or completely blocked, respectively, or plants or insects, or cells, respectively, into which the PNA molecules have been inserted according to the method of the invention, are transfected with the gene that expresses the glycoprotein so that the recombinant glycoproteins are expressed. In doing so, any protein can be used which is of medical interest.

Moreover, the present invention relates to recombinant glycoproteins according to a method described above, wherein they have been prepared in plant or insect systems and wherein their peptide sequence comprises less than 50%, in particular less than 20%, particularly preferred 0%, of the α1,3-bound fucose residues occurring in proteins expressed in non-fucosyl transferase-reduced plant or insect systems. Naturally, glycoproteins which do not comprise α1,3-bound fucose residues are to be preferred. The amount of α1,3-bound fucose will depend on the degree of the above-described suppression of the GlcNAc-α1,3-fucosyl transferase.

Preferably, the invention relates to recombinant human glycoproteins which have been produced in plant or insect systems according to a method described above and whose peptide sequence comprises less than 50%, in particular less than 20%, particularly preferred 0%, of the α1,3-bound fucose residues occurring in the proteins expressed in non-fucosyl transferase-reduced plant or insect systems.

A particularly preferred embodiment relates to recombinant human glycoproteins for medical use which have been prepared in plant or insect systems according to a method described above and whose peptide sequence comprises less than 50%, in particular less than 20%, particularly preferred 0%, of the α1,3-bound fucose residues occurring in the proteins expressed in non-fucosyl transferase-reduced plant or insect systems.

The glycoproteins according to the invention may include other bound oligosaccharide units specific for plants or insects, respectively, whereby—in the case of human glycoproteins—they differ from these natural glycoproteins. Nevertheless, by the glycoproteins according to the invention, a slighter immune reaction or no immune reaction at all, respectively, is triggered in the human body, since, as has already been explained in the introductory portion of the specification, the α1,3-bound fucose residues are the main cause for the immune reactions or cross immune reaction, respectively, to plant and insect glycoproteins.

A further aspect comprises a pharmaceutical composition comprising the glycoproteins according to the invention. In addition to the glycoproteins of the invention, the pharmaceutical composition comprises further additions common for such compositions. These are, e.g., suitable diluting agents of various buffer contents (e.g. Tris-HCl, acetate, phosphate, pH and ionic strength, additives, such as tensides and solubilizers (e.g. Tween 80, Polysorbate 80), preservatives (e.g. Thimerosal, benzyl alcohol), adjuvants, antioxidants (e.g. ascorbic acid, sodium metabisulfite), emulsifiers, fillers (e.g. lactose, mannitol), covalent bonds of polymers, such as polyethylene glycol, to the protein, incorporation of the material in particulate compositions of polymeric compounds, such as polylactic acid, polyglycolic acid, etc. or in liposomes, auxiliary agents and/or carrier substances which are suitable in the respective treatment. Such compositions will influence the physical condition, stability, rate of in vivo liberation and rate of in vivo excretion of the glycoproteins of the invention.

The invention also provides a method of selecting DNA molecules which code for a GlcNAc-α1,3-fucosyl transferase, in a sample, wherein the labelled DNA molecules of the invention are admixed to the sample, which bind to the DNA molecules that code for a GlcNAc-α1,3-fucosyl transferase. The hybridized DNA molecules can be detected, quantitated and selected. For the sample to contain single strand DNA with which the labelled DNA molecules can hybridize, the sample is denatured, e.g. by heating.

One possible way is to separate the DNA to be assayed, possibly after the addition of endonucleases, by gele electrophoresis on an agarose gel. After having been transferred to a membrane of nitrocellulose, the labelled DNA molecules according to the invention are admixed which hybridize to the corresponding homologous DNA molecule ("Southern blotting").

Another possible way consists in finding homologous genes from other species by PCR-dependent methods using specific and/or degenerated primers, derived from the sequence of the DNA molecule according to the invention.

Preferably, the sample for the above-identified inventive method comprises genomic DNA of a plant or insect organism. By this method, a large number of plants and insects is assayed in a very rapid and efficient manner for the presence of the GlcNAc-α1,3-fucosyl transferase gene. In this manner, it is respectively possible to select plants and insects which do not comprise this gene, or to suppress or completely block, respectively, the expression of the GlcNAc-α1,3-fucosyl transferase in such plants and insects which comprise this gene, by an above-described method of the invention, so that subsequently they may be used for the transfection and production of (human) glycoproteins.

The invention also relates to DNA molecules which code for a GlcNAc-α1,3-fucosyl transferase which have been selected according to the two last-mentioned methods and subsequently have been isolated from the sample. These molecules can be used for further assays. They can be sequenced and in turn can be used as DNA probes for finding GlcNAc-α1,3-fucosyl transferases. These—labelled—DNA molecules will function for organisms, which are related to the organisms from which they have been isolated, more efficiently as probes than the DNA molecules of the invention.

A further aspect of the invention relates to a preparation of GlcNAc-α1,3-fucosyl transferase cloned according to the invention which comprises isoforms having pI values of between 6.0 and 9.0, in particular between 6.8 and 8.2. The pI values of a protein is that pH value at which its net charge is zero and is dependent on the amino acid sequence, the glycosylation pattern as well as on the spatial structure of the protein. The GlcNAc-α1,3-fucosyl transferase comprises at least 7 isoforms which have a pI value in this range. The reason for the various isoforms of the transferase are, e.g., different glycosylations as well as limited proteolysis. Tests have shown that mung bean seedlings of various plants have different relationships of the isozymes. The pI value of a protein can be determined by isoelectric focussing, which is known to the skilled artisan.

The main isoform of the enzyme has an apparent molecular weight of 54 kDa.

In particular, the preparation of the invention comprises isoforms having pI values of 6.8, 7.1 and 7.6.

The invention also relates to a method of preparing "plantified" carbohydrate units of human and other vertebrate glycoproteins, wherein fucose units as well as GlcNAc-α1,3-fucosyl transferase encoded by an above-described DNA molecule are admixed to a sample that comprises a carbohydrate unit or a glycoprotein, respectively, so that fucose in α1,3-position will be bound by the GlcNAc-α1,3-fucosyl transferase to the carbohydrate unit or to the glycoprotein, respectively. By the method according to the invention for cloning GlcNAc-α1,3-fucosyl transferase it is possible to produce large amounts of purified enzyme. To obtain a fully active transferase, suitable reaction conditions are provided. It has been shown that the transferase has a particularly high activity at a pH of approximately 7, if 2-(N-morpholino)-ethane sulfonic acid-HCl is used as the buffer. In the presence of bivalent cations, in particular $Mn^{2-}$, the activity of the recombinant transferase is enhanced. The carbohydrate unit is admixed to the sample either in unbound form or bound to a protein. The recombinant transferase is active for both forms.

The invention will be explained in more detail by way of the following examples and drawing figures to which, of course, it shall not be restricted.

BRIEF DESCRIPTION OF THE DRAWINGS

FIG. 4 shows the N-terminal sequences of 4 tryptic peptides 1-4 as well as the DNA sequence of three primers, S1, A2 and A3;

FIGS. 5a and 5b show the cDNA sequence of α1,3-fucosyl transferase;

FIGS. 6a and 6b show the amino acid sequence of α1,3-fucosyl transferase derived therefrom;

FIG. 8 shows a comparison of the conserved motifs of various fucosyl transferases;

FIGS. 11 and 12 show mass spectra;

FIG. 14 shows the cDNA and deduced amino acid sequence of mung bean core •1,3-fucosyltransferase. The complete dDNA comprises 2198 base pairs which encodes a 510-amino acid protein with a theoretical molecular mass of 56.8 kDa. The hydrophobic putative transmembrane domain is double underlined. The peptide sequences obtain by amino acid sequencing are indicated by single underlining. Consensus sites for asparagine-linked glycosylation are indicated by diamonds. (See Leiter et al., 1999, J Biol Chem 274; 21830-21839, the entire contents of which are incorporated herein by reference.);

Figure 15:
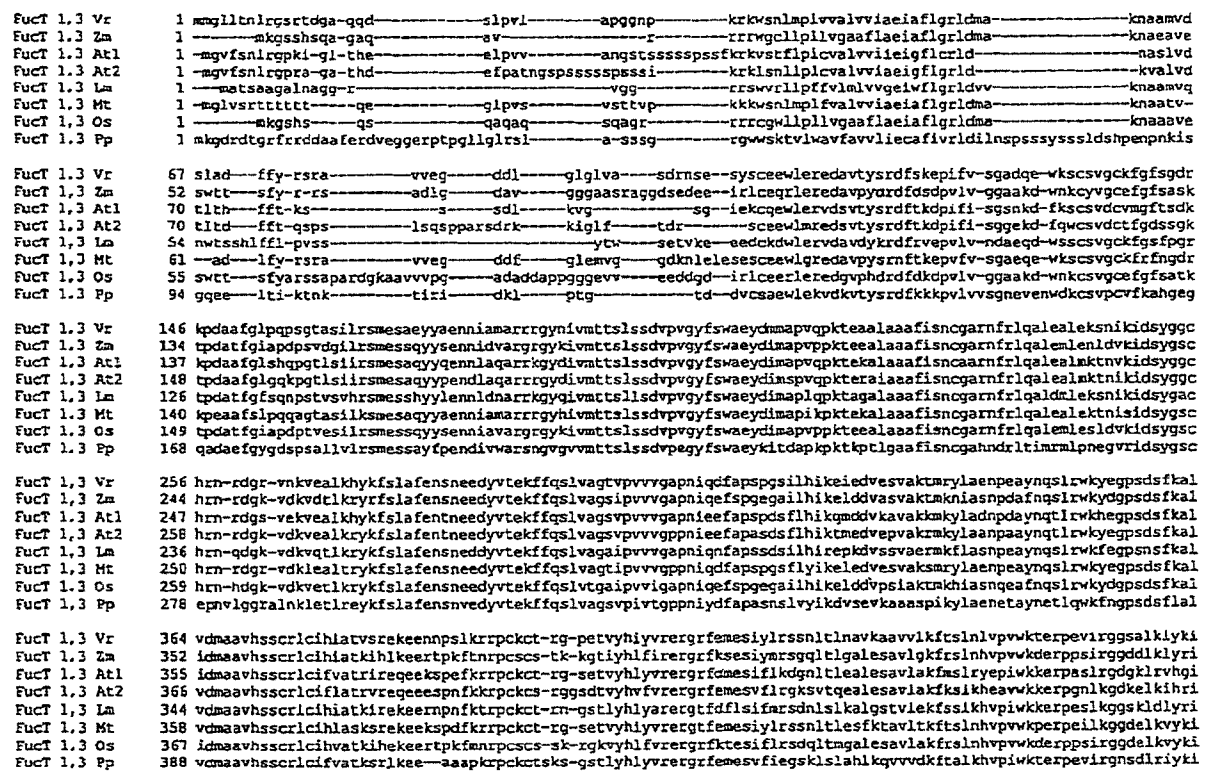

FIG. 15 shows an alignment of •1,3-fucosyltransferase amino acid sequences;

Figure 16:
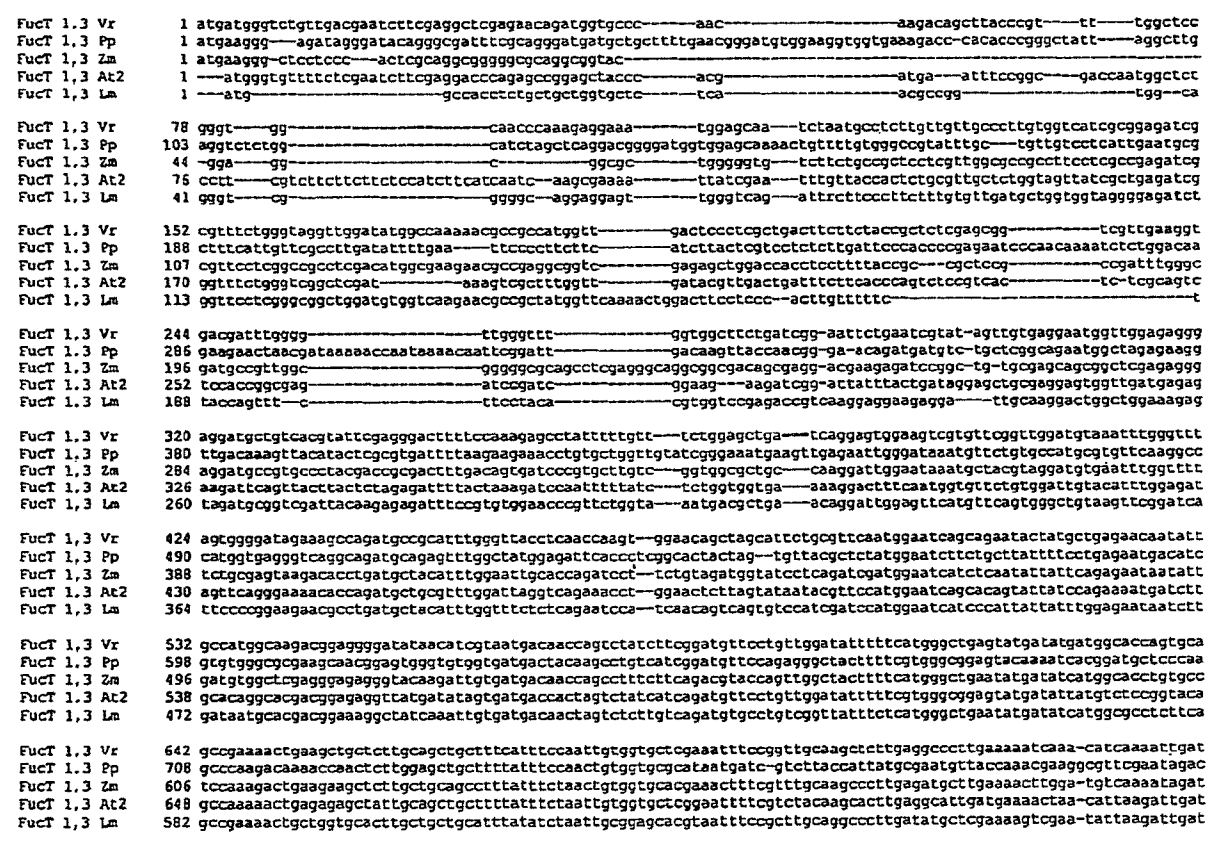
Figure 16:
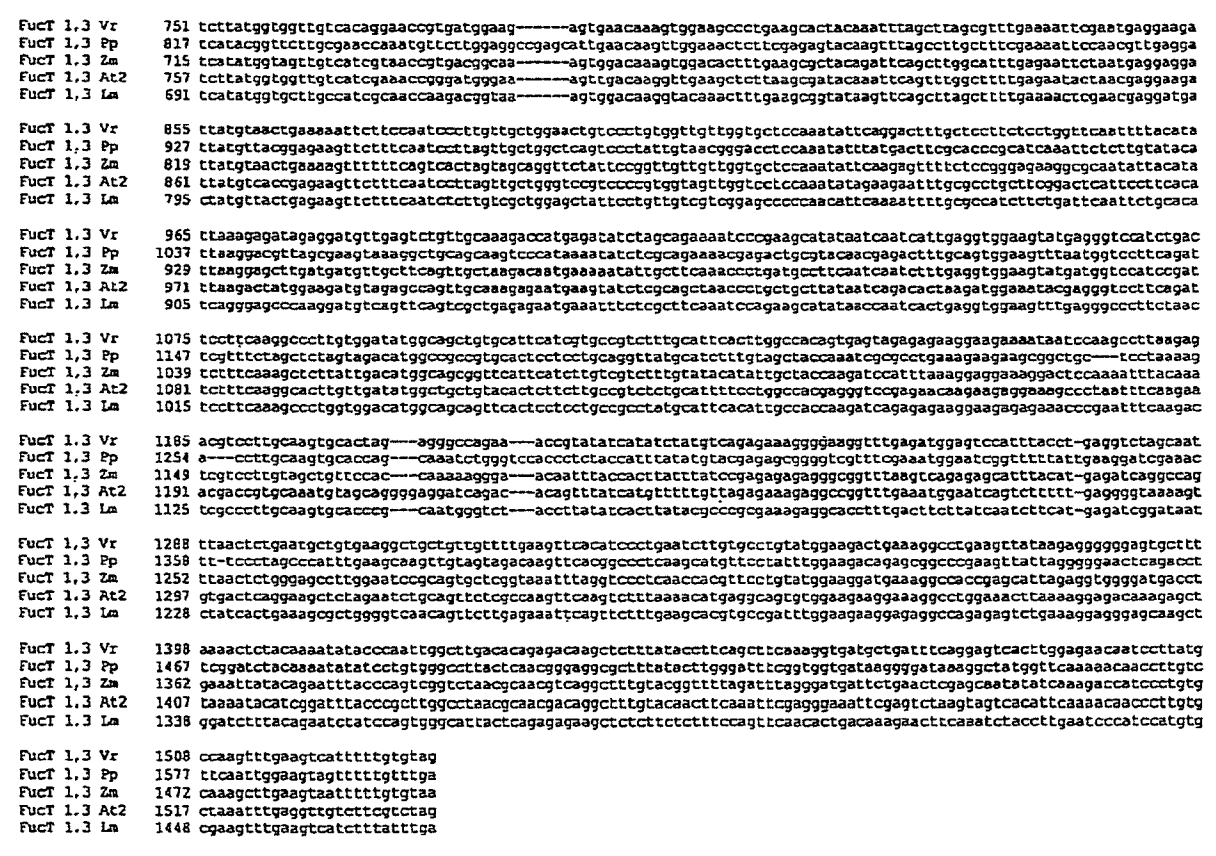

FIG. 16 shows an alignment of •1,3-fucosyltransferase cDNA sequences;

Figure 17:
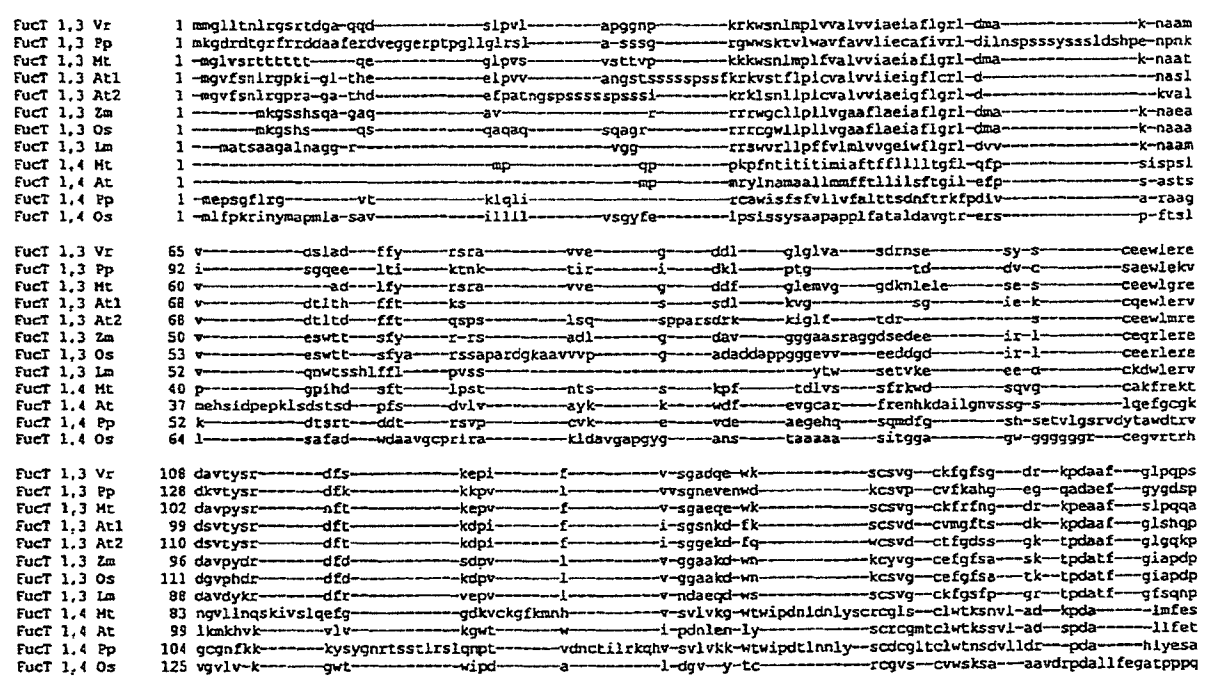
Figure 17:
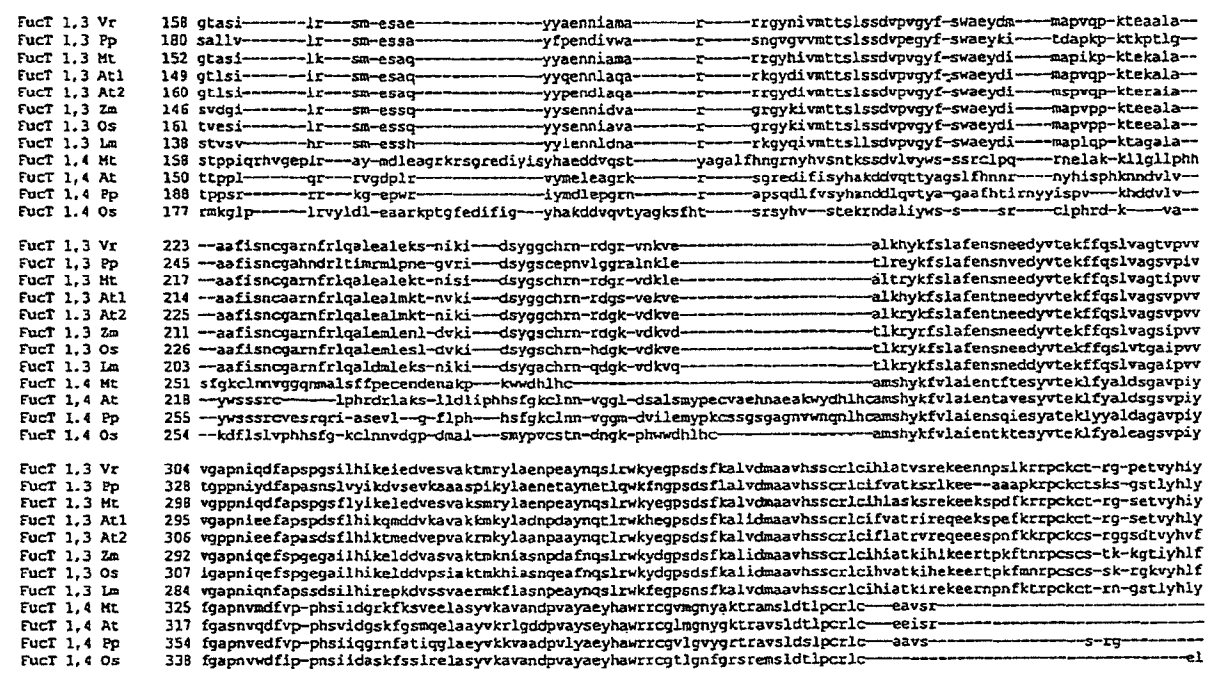

FIG. 17 shows an alignment of •1,3-fucosyltransferase amino acid sequences in comparison to •1,4-fucosyltransferase amino acid sequences;

FIG. 18 shows an alignment of •1,4-fucosyltransferase amino acid sequences; and

Figure 19:
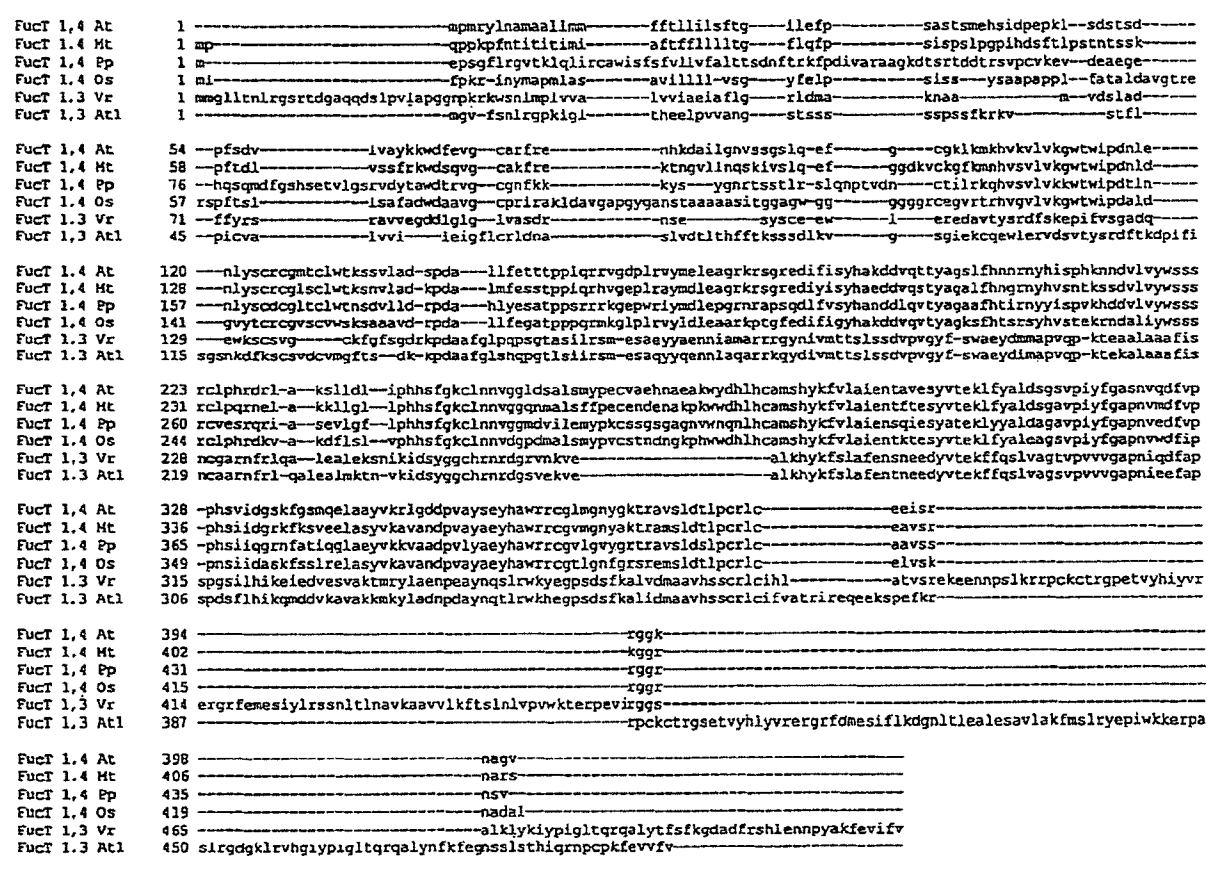

FIG. 19 shows an alignment of •1,4-fucosyltransferase amino acid sequences in comparison to •1,3-fucosyltransferase amino acid sequences.

EXAMPLES

Example 1

Isolation of the core-α1,3-fucosyl transferase

All the steps were carried out at 4° C. Mung bean seedlings were homogenized in a mixer, 0.75 volumes of extraction buffer being used per kg of beans. Subsequently, the homogenate was filtered through two layers of cotton fabric, and the filtrate was centrifuged for 40 min at 30000×g. The supernatant was discarded, and the pellet was extracted with solution buffer over night with continuous stirring. Subsequent centrifugation at 30000×g for 40 min yielded the triton extract.

The triton extract was purified as follows:

Step 1: The triton extract was applied to a microgranular diethyl amino ethyl cellulose anion exchanger DE52 cellulose column (5×28 cm) from Whatman, which previously had been calibrated with buffer A. The non-bound fraction was further treated in step 2.

Step 2: The sample was applied to an Affi-Gel Blue column (2,5×32) column calibrated with buffer A. After washing of the column whith this buffer, adsorbed protein was eluted with buffer A comprising 0.5 M NaCl.

Step 3: After dialysis of the eluate from step 2 against buffer B, it was applied to an S-Sepharose column calibrated with the same buffer. Bound protein was eluted with a linear gradient of from 0 to 0.5 M NaCl in buffer B. Fractions with GlcNAc-α1,3-fucosyl transferase were pooled and dialyzed against buffer C.

Step 4: The dialyzed sample was applied to a GnGn-Sepharose column calibrated with buffer C. The bound protein was eluted with buffer C comprising 1 M NaCl instead of $MnCl_2$.

Step 5: Subsequently, the enzyme was dialyzed against buffer D and applied to a GDP-Hexanolamine-Sepharose column. After having washed the column with buffer D, the transferase was eluted by substituting $MgCl_2$ and NaCl with 0.5 mM GDP. Active fractions were pooled, dialyzed against 20 mM Tris-HCl buffer, pH 7.3, and lyophilized.

The enzymatic activity of the GlcNAc-α1,3-fucosyl transferase was determined by using GnGn peptide and GDP-L-[U-$^{14}$C]-fucose at substrate concentrations of 0.5 and 0.25 each, in the presence of 2-(N-morpholino)ethanesulfonic acid-HCl buffer, Triton X-100, $MnCl_2$, GlcNAc and AMP (according to Staudacher et al., 1998, Glycoconjugate J. 15, 355-360; Staudacher et al., 1991, Eur. J. Biochem. 199, 745-751).

Protein concentrations were determined by aid of the bicinchoninic acid method (Pierce) or, in the final steps of enzyme purification, by means of amino acid analysis (Altmann 1992, Anal. Biochem. 204, 215-219).

Figure 1:
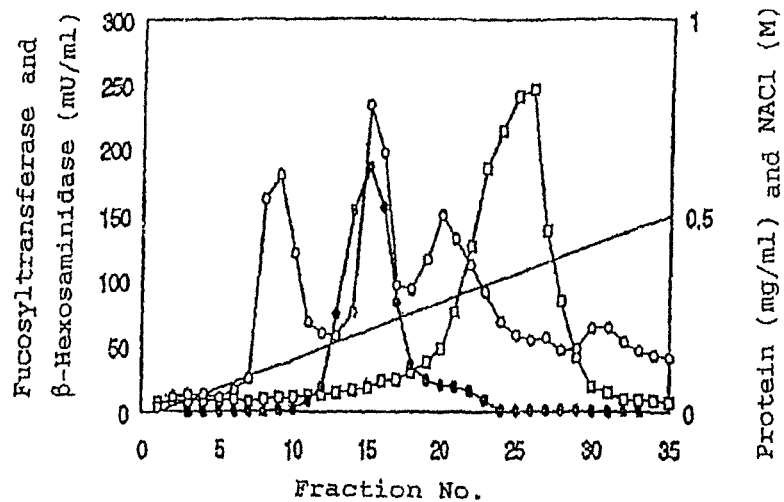
FIGS. 1a and 1b show, as curves, the measured amounts of protein and the measured enzyme activity in the individual fractions of the eluate.
Figure 1:
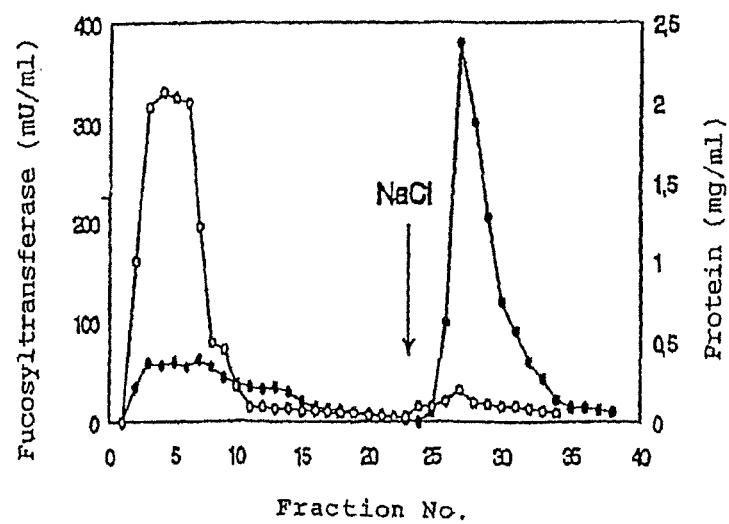

In FIGS. 1a and 1b, the measured amounts of protein and the measured enzyme activity in the individual fractions of the eluate are illustrated as curves. FIG. 1a shows the above-described separation on the S-Sepharose column, FIG. 1b shows the separation on the GnGn-Sepharose column, the circle representing protein, the black, full circle representing GlcNAc-α1,3-fucosyl transferase, and the square illustrating N-acetyl-β-glucosaminidase. One U is defined as that amount of enzyme which transfers 1 mmol of fucose onto an acceptor per minute.

Table 1 shows the individual steps of transferase purification.

TABLE 1

| Purification step | Total protein mg | Total activity mU | Specific activity mU/mg | Purification factor -fold | Yield % |
|---|---|---|---|---|---|
| Triton X-100 extract | 91500 | 4846 | 0.05 | 1 | 100 |
| DE52 | 43700 | 4750 | 0.10 | 2 | 98.0 |
| Affigel Blue | 180.5 | 4134 | 23 | 460 | 85.3 |
| S-Sepharose | 8.4 | 3251 | 390 | 7800 | 67.1 |
| GnGn-Sepharose | 0.13[1] | 1044 | 8030 | 160000 | 21.5 |
| GDP-Hexanolamine-Sepharose | 0.02[1] | 867 | 43350 | 867000 | 17.9 |

[1]determined by amino acid analysis

Extraction Buffer:
 0.5 mM Dithiothreitol
 1 mM EDTA
 0.5% Polyvinyl polypyrrolidone
 0.25 M Sucrose
 50 mM Tris-HCl buffer, pH 7.3

Solution Buffer:
 0.5 mM Dithiothreitol
 1 mM EDTA
 1.5% Triton X-100
 50 mM Tris-HCl, pH 7.3

Buffer A:
 25 mM Tris-HCl buffer, pH 7.3, comprising:
 0.1% Triton X-100 and
 0.02% $NaN_3$ Buffer B:
 25 mM Na citrate buffer, pH 5.3, comprising:
 0.1% Triton X-100 and
 0.02% $NaN_3$ Buffer C:
 25 mM Tris-HCl buffer, pH 7.3, comprising:
 5 mM $MnCl_2$nd
 0.02% $NaN_3$ Buffer D:
 25 mM Tris-HCl, pH 7.3, comprising:
 10 mM $MgCl_2$
 0.1 M NaCl, and
 0.02% $NaN_3$ Example 2

SDS-PAGE and isoelectric Focussing

An SDS-PAGE was carried out in a Biorad Mini-protean cell on gels with 12.5% acrylamide and 1% bisacrylamide. The gels were stained either with Coomassie Brilliant Blue R-250 or Silver. Isoelectric focussing of the fucosyl transferase was carried out on prefabricated gels having a pI range of between 6-9 (Servalyt precotes 6-9, Serva). The gels were stained with silver according to the producer's protocol. For the two-dimensional electrophoresis, lanes were cut out of the focussing gel, treated with S-alkylating reagents and SDS and subjected to an SDS-PAGE, as described above.

Figure 2:
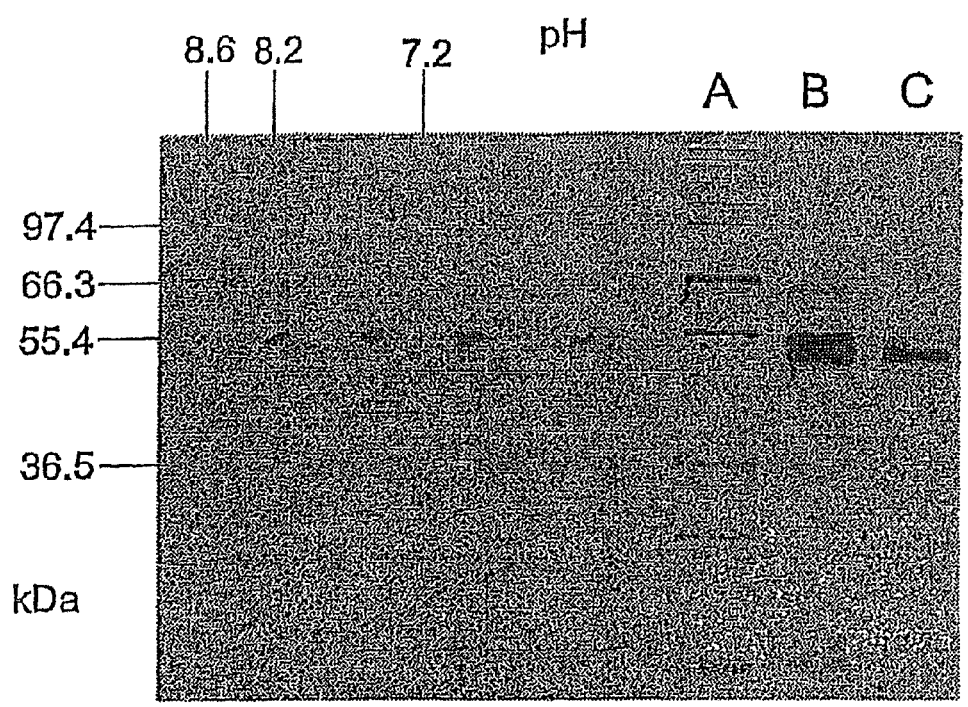
FIG. 2 shows an electrophoresis gel analysis of GlcNAc-α1,3-fucosyl transferase.

FIG. 2 shows the illustration of an electrophoresis gel of GlcNAc-α1,3-fucosyl transferase, the two-dimensional electrophoresis being indicated on the left-hand side, and the one-dimensional SDS-PAGE being illustrated on the right-hand side. The lane denoted by A is a standard, the lane denoted by B is the GlcNAc-α1,3-fucosyl transferase from the GnGn-Sepharose column, and the lane denoted by C is the "purified" GlcNAc-α1,3-fucosyl transferase, i.e. the fraction of the GDP Hexanolamine Sepharose column. The two bands at 54 and 56 kDa represent isoforms of the transferase.

Figure 3:
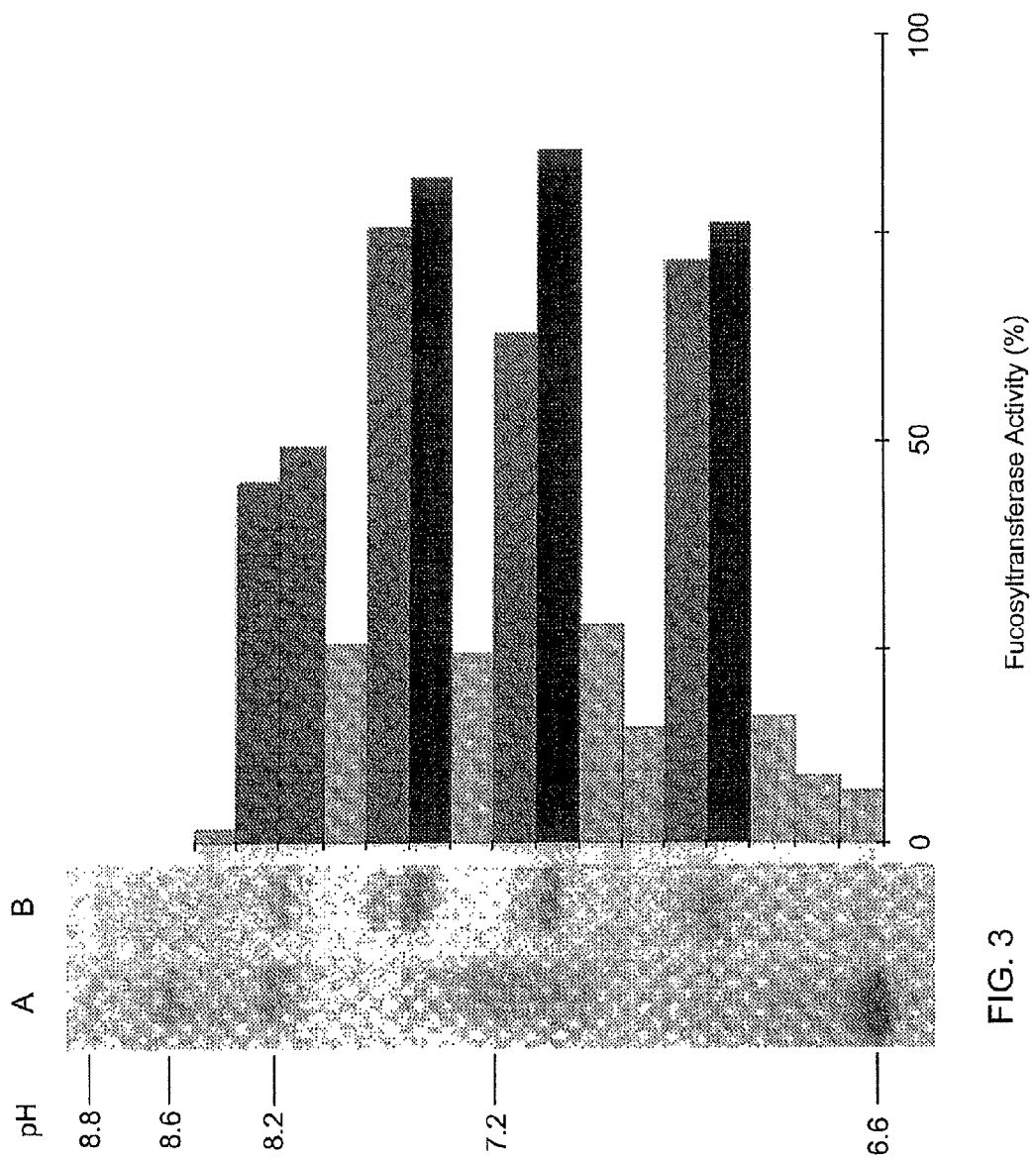
FIG. 3 shows the result of the isoelectric focussing and the measured transferase activity of the individual isoforms.

FIG. 3 shows the result of the isoelectric focussing. Lane A was stained with silver, on lane B, the activity of the transferase isoforms was tested. The activity is indicated as % fucose which had been transferred from GDP-fucose onto the substrate.

Example 3

Peptide Sequencing

For sequencing of the protein, bands were cut out of the Coomassie-stained SDS-Polyacrylamide gel, carboxyamidomethylated and cleaved with trypsin according to Görg et al. 1988, Electrophoresis, 9, 681-692. The tryptic peptides were separated with the reverse phase HPLC on a 1.0×250 mm Vydac C18 at 40° C. at a flow rate of 0.05 ml/min, wherein a HP 1100 apparatus (Hewlett-Packard) was used. The isolated peptides were separated with a Hewlett-Packard G1005 A Protein Sequencing System according to the producer's protocol. Furthermore, the peptide mixture was analyzed by Ingel digestion with MALDI-TOF MS (see below).

FIG. 4 shows the N-terminal sequences of 4 tryptic peptides 1-4 (SEQ ID NO: 5-8). Departing from the first three peptides, primers S1, A2 and A3 were prepared (SEQ ID NO: 9-11).

Example 4

RT-PCR and cDNA Cloning

The entire RNA was isolated from a 3-day-old mung bean hypocotyl, wherein the SV Total RNA Isolating System of Promega was used. To prepare the first strand cDNA, the entire RNA was incubated for 1 h at 48° C. with AMV reverse transcriptase and oligo(dT) primers, wherein the Reverse Transcription System of Promega was used.

The first strand cDNA was subjected to a PCR, wherein a combination of sense and antisense primers was used: To 10 µl of the reverse transcription reaction mixture, the following was added:

50 µl with 0.1 mmol of each primer, 0.1 mM dNTPs, 2 mM $MgCl_2$, 10 mM Tris-HCl buffer, pH 9.0, 50 mM KCl and 0.1% Triton X-100.

After a first denaturing step at 95° C. for 2 min, 40 cycles of 1 min at 95° C., 1 min at 49° C. and 2 min at 72° C. were passed. The last extension step was carried out at 72° C. for 8 min. PCR products were subcloned into the pCR2.1 vector, with the TA Cloning Kit of Invitrogen being used, and sequenced. The products of this PCR were two DNA fragments with lengths of 744 bp and 780 bp, both DNA fragments having the same 5'-end (cf. also FIG. 7).

Starting from these two DNA fragments, the missing 5' and 3' regions of the cDNA were obtained by 5' and 3' rapid amplification of cDNA ends (RACE), wherein the RACE Kit of Gibco-BRL was used. As the antisense primer, the universal amplification primer of the kit, and as the sense primer, either 5'-CTGGAACTGTCCCTGTGGTT-3' (SEQ ID NO: 12) or 5'-AGTGCACTAGAGGGCCAGAA-3' (SEQ ID NO: 13) were used. As the sense primer, also the shortened anchor primer of the kit, and as the antisense primer, 5'-TTCGAG-CACCACAATTGGAAAT-3' (SEQ ID NO: 14) or 5'-GAAT-GCAAAGACGGCACGATGAAT-3' (SEQ ID NO: 15) were used.

The PCR was carried out with an annealing temperature of 55° C. and under the above-described conditions. The 5' and 3' RACE products were subcloned into the pCR2.1 vector and sequenced: The sequences of the subcloned fragments were sequenced by means of the didesoxynucleotide method (ABI PRISM Dye Terminator Cycle Sequencing Ready reaction Kit and ABI PRISM 310 Genetic analyser (Perkin Elmer)). T7 and M13 forward primers were used for the sequencing of the products cloned into vector pCR2.1. Both strands of the coding region were sequenced by the Vienna VBC Genomics-Sequencing Service, infrared-labelled primers (IRD700 and IRD800) and an LI-COR Long Read IR 4200 Sequencer (Lincoln, Nebr.) being used.

FIGS. 5a and 5b show the entire cDNA which has a size of 2198 bp and an open reading frame of 1530 bp (SEQ ID NO: 1). The open reading frame (start codon at base pairs 211-213, stop codon at base pairs 1740-1743) codes for a protein of 510 amino acids having a molecular weight of 56.8 kDA and a theoretical pI value of 7.51.

FIGS. 6a and 6b show the cDNA-derived amino acid sequence of the GlcNAc-α1,3-fucosyl transferase (SEQ ID NO: 2). Sites for the asparagine-bound glycosylation are at Asn346 and Asn429.

Figure 7:
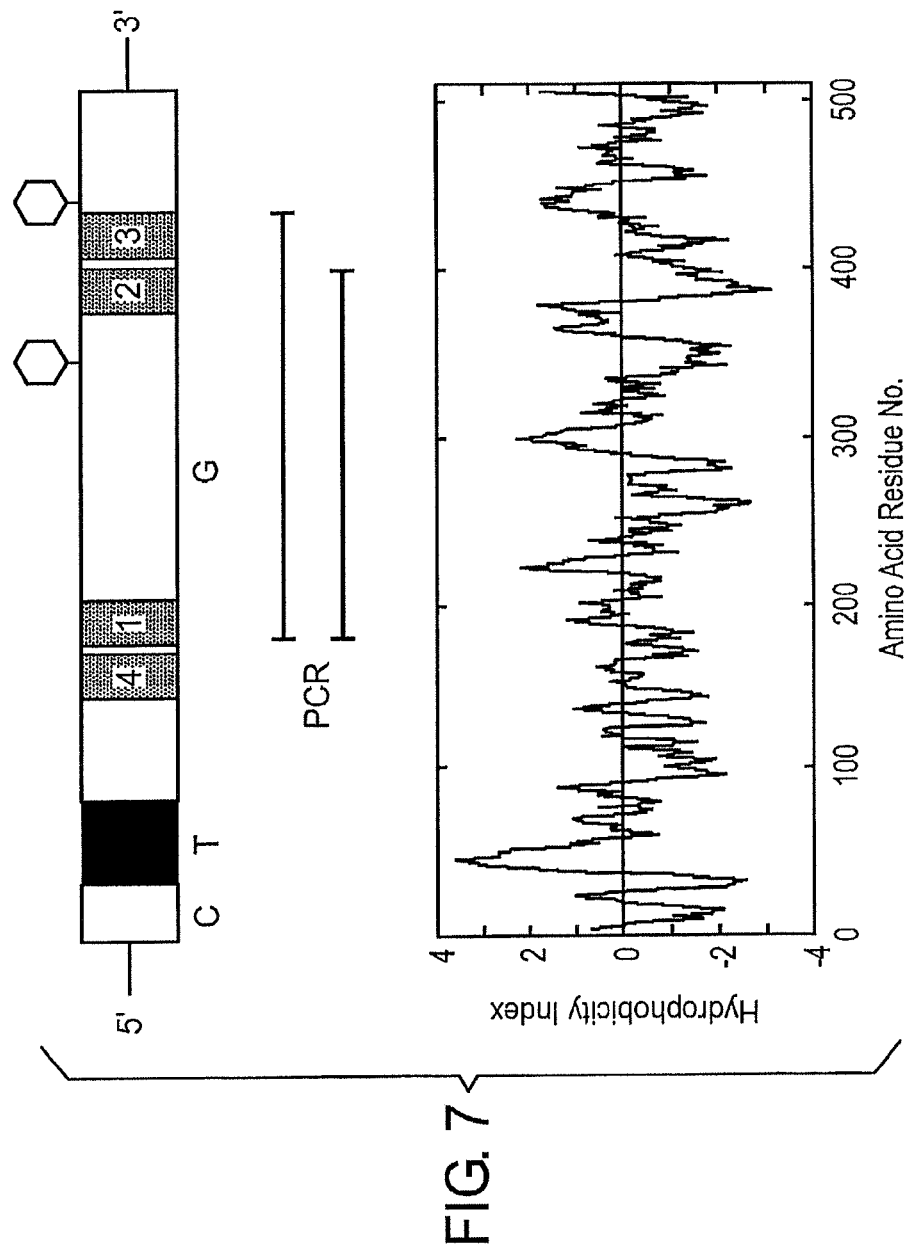
FIG. 7 is a schematic representation of the α1,3-fucosyl transferase as well as the hydrophobicity of the amino acid residues.

In FIG. 7, the schematic GlcNAc-α1,3-fucosyl transferase-cDNA (top) and the derived hydrophobicity index of the encoded protein (bottom) are illustrated, a positive hydrophobicity index meaning an increased hydrophobicity. Therebetween, the sizes of the two above-indicated PCR products are shown in relationship to the complete cDNA. The coding region is illustrated by the beam, "C" coding for the postulated cytoplasmatic region, T for the postulated transmembrane region, and G for the postulated Golgi lumen catalytic region of transferase. The analysis of the DNA sequence by "TMpred" (from EMBnet, Switzerland) gave an assumed transmembrane region between Asn36 and Gly54. The C-terminal region of the enzyme probably comprises the catalytic region and consequently should point into the lumen of the Golgi apparatus. According to this, this transferase seems to be a type II transmembrane protein like all the hitherto analyzed glycosyl transferases which are involved in glycoprotein biosynthesis (Joziasse, 1992, Glycobiology 2, 271-277). The gray regions represent the four tryptic peptides, the hexagons represent the potential N-glycosylation sites. A BLASTP search in all data banks accesible via NCBI showed a similarity between the GlcNAc-α1,3-fucosyl transferase and other α1,3/4-fucosyl transferases, e.g. human fucosyl transferase VI. At 18-21% (examined by SIM-LALNVIEW, Expase, Switzerland), the total similarity was beyond any significance. Nevertheless, a sequence range of 35 amino acids (SEQ ID NO: 4) shows a strikingly high homology to other α1,3/4-fucosyl transferases (FIG. 8). This sequence region is located between Glu267 and Pro301 of SEQ ID NO: 2.

Example 5

Expression of Recombinant GlcNAc-α1,3-fucosyl Transferase in Insect Cells

The encoding region of the assumed GlcNAc-α1,3-fucosyl transferase including cytoplasmatic and transmembrane region was amplified with the forward primer 5'-CGGCG-GATCCGCAATTGAATGATG-3' (SEQ ID NO: 16) and reverse primer 5'-CCGGCTGCAGTACCATTTAGCGCAT-3' (SEQ ID NO: 17) by means of the Expand High Fidelity PCR System of Boehringer Mannheim. The PCR product was double-digested with PstI and BamHI and subcloned in alkaline phosphatase-treated baculovirus transfer vector pVL1393 which previously had been digested with PstI and BamHI. To ensure a homologous recombination, the transfer vector was co-transfected with Baculo Gold viral DNA (PharMingen, Sand Diego, Calif.) in Sf9 insect cells in IPL-41 Medium with lipofectin. After an incubation of 5 days at 27° C., various volumes of the supernatant with the recombinant virus were used for infecting the Sf21 insect cells. After an incubation of 4 days at 27° C. in IPL-41 Medium with 5% FCS, the Sf1 cells were harvested and washed 2× with phosphate-buffered saline solution. The cells were resuspended in 25 mM Tris HCl buffer, pH 7.4, with 2% Triton X-100 and broken up by sonication on ice.

Example 6

Assay for GlcNAc-α1,3-fucosyl Transferase Activity

The homogenate and the cell supernatant were assayed for GlcNAc-α1,3-fucosyl transferase. Blind samples were carried out with recombinant baculovirus which codes for the tobacco-GlcNAc-transferase I (Strasser et al., 1999, Glycobiology, in the process of printing).

Figure 9:
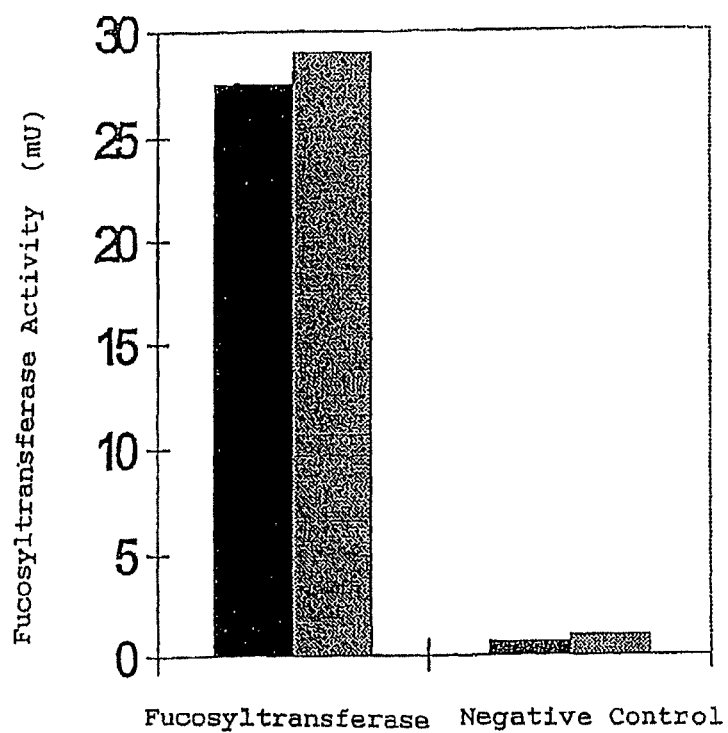
FIG. 9 shows a comparison of the fucosyl transferase activity of insect cells transfected with the α1,3-fucosyl transferase gene with that of a negative control.

FIG. 9 shows the measured enzyme activity of the recombinant GlcNAc-α1,3-fucosyl transferase as well as of the negative control. At best, the enzyme activity of the cotransfected cells and their supernatant was 30× higher than that of the negative controls. This endogenous activity which is measurable in the absence of the recombinant transferase, substantially comes from the insect-α1,6-fucosyl transferase and only a low percentage thereof comes from the GlcNAc-α1, 3-fucosyl transferase. Accordingly, the increase in the GlcNAc-α1,3-fucosyl transferase coming from the recombinant baculoviruses is far more than the 100-fold.

The enzyme exhibited a broad maximum activity around a pH of 7.0, if the activity was measured in 2-(N-morpholino)-ethanesulfonic acid-HCl buffer. As is apparent in Table 2, the addition of bivalent cations, in particular $Mn^{2+}$, enhances the activity of the recombinant transferase.

TABLE 2

| Additive (conc. 10 mM) | Relative Activity (Acceptor: GnGn-peptide) % |
| --- | --- |
| none | 21 |
| EDTA | 18 |
| $MnCl_2$ | 100 |
| $CaCl_2$ | 82 |
| $MgCl_2$ | 52 |
| $CdCl_2$ | 44 |
| $CoCl_2$ | 35 |
| $CuCl_2$ | 3 |
| $NiCl_2$ | 24 |
| $ZnCl_2$ | 0.6 |

Figure 10:
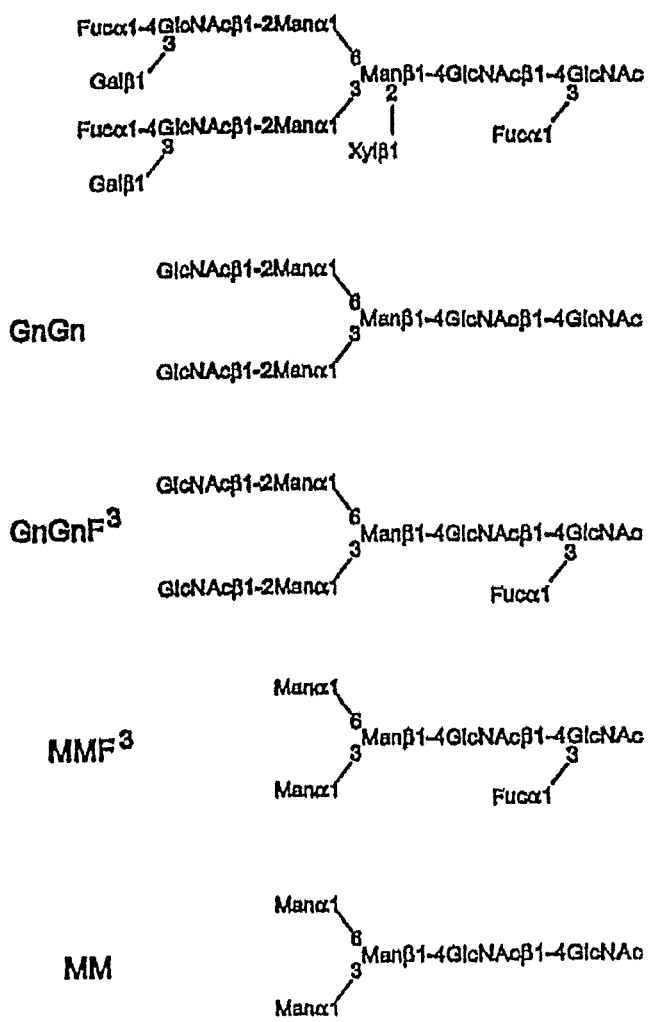
FIGS. 10a and 10b show structures of different acceptors of the α1,3-fucosyl transferase.
Figure 10:
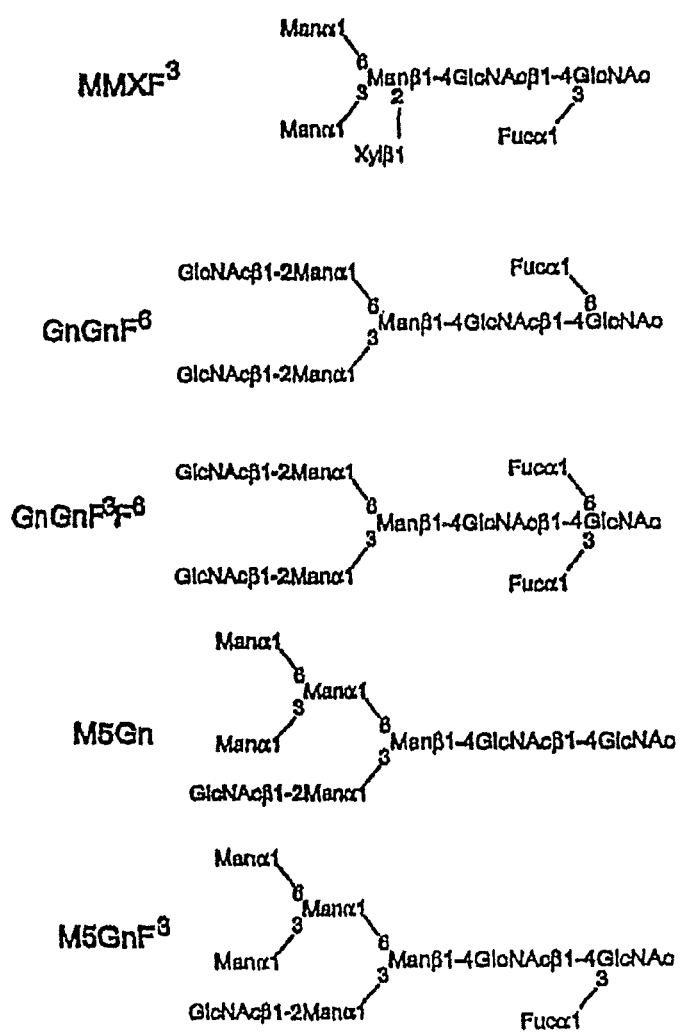

Table 3 shows that among the acceptors used, the GnGn-peptide exhibits the highest incorporation rates under standard test conditions, followed closely by $GnGnF^6$eptide and M5Gn-Asn. A transfer to the MM peptide could not be found, which MM peptide does not comprise the reducing GlcNAc-end at the 3-bound mannose. This structure seems to be necessary for the core fucosyl transferase. The recombinant transferase, moreover, was inactive relative to the acceptors commonly used, the α,3/4-fucosyl transferases used for determining the blood groups, which transfer the fucose to GlcNAc at the non-reducing ends of oligosaccharides. The apparent $K_m$-values for the acceptor substrate GnGn peptide, $GnGnF^6$peptide, M5Gn-Asn, and for the donor substrate GDP-fucose, were assessed to be 0.19, 0.13, 0.23 and 0.11, respectively. The structures of the molecules are illustrated in FIGS. 10a and 10b.

TABLE 3

| Acceptor Substrate | Rel. Activity % | $K_m$-Value mM |
| --- | --- | --- |
| GnGn-peptide | 100 | 0.19 |
| $GnGnF^6$-peptide | 87 | 0.13 |
| M5Gn-Asn | 71 | 0.23 |
| MM-peptide | 0 | |
| Galβ-4GlcNAc | 0 | |
| Galβ1-3GlcNAc | 0 | |
| Galβ1-3GlcNAcβ1-3Galβ1-4Glc | 0 | |

Example 7

Mass Spectrometry of the fucosyl Transferase Product

Dabsylated GnGn hexapeptide (2 nmol) was incubated with the insect cell homogenate comprising the recombinant GlcNAc-α,3-fucosyl transferase (0.08 mU) in the presence of non-radioactive GDP-L-fucose (10 nmol), 2 (N-morpholino)-ethanesulfonic acid-HCl buffer, Triton X-100, $MnCl_2$, GlcNAc and AMP. A negative control was carried out with a homogenate of the infected insect cells for the blind samples. The samples were incubated for 16 h at 37° C. and analyzed by means of MALDI TOF mass spectrometry. Mass spectrometry was performed on a DYNAMO (Therrmo Bio-Analysis, Santa Fe, N. Mex.), a MALDI-TOF MS which is capable of dynamic extraction (synonym for late extraction).

Two types of sample matrix preparations were used: peptides and dabsylated glycopeptides were dissolved in 5% formic acid, and aliquots were applied to the target, air-dried, and covered with 1% α-cyano-4-hydroxy cinnamic acid. Pyridyl-aminated glycans, reduced oligosaccharides and non-derivatized glycopeptides were diluted with water, applied to the target and air-dried. After addition of 2% 2.5-dihydroxy benzoic acid, the samples were immediately dried by applying a vacuum.

Figure 11:
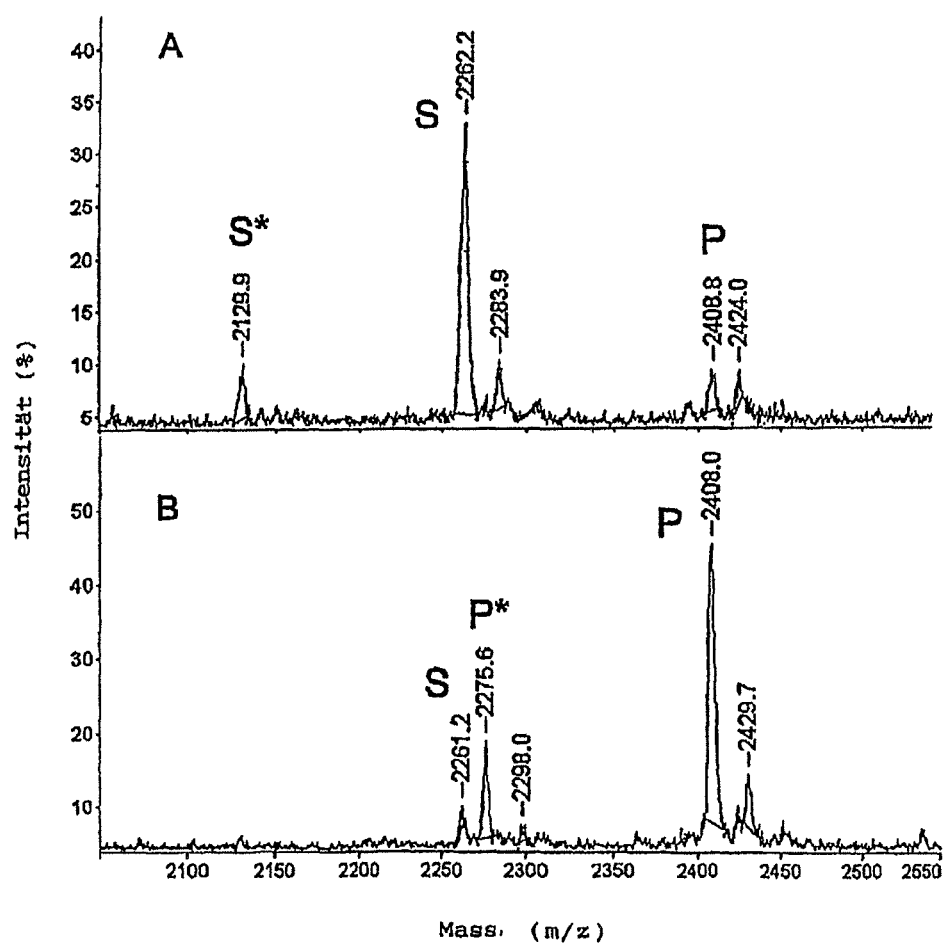

FIG. 11 shows the mass spectrum of these samples, A being the negative control: The main peak (S) shows the Dabsyl-Val-Gly-Glu-($GlcNAc_4Man_3$)Asn-Arg-Thr substrate, the calculated $[M+H]^-$ value being 2262.3. This substrate also appears as sodium addition product and as smaller ion which has been formed by fragmentation of the Azo function of the Dabsyl group, at (S*). A small product amount (P, $[M+H]^+$ =2408.4) is a consequence of the endogenous α1,6-fucosyl transferase. The peak at m/z=2424.0 shows the incomplete de-galactosylation of the substrate. The mass spectrum B shows the sample with recombinant α1,3-fucosyl transferase. The main peak (P) represents the fucosylated product, (P*) its fragmented ion.

In addition, aliquots of both samples were mixed with each other so as to obtain similar concentrations of substrate and product (sample A). This mixture was diluted with 0.1 M ammonium acetate, pH 4.0, comprising 10 mU of N-glycosidase A (sample B), or with 50 mM Tris/HCl, pH 8.5, comprising 100 mU (1 U hydrolyses 1 mmol of substrate per min) of N-glycosidase F (sample C). After 2 and 20 h, small aliquots of these mixtures were taken and analyzed by means of MALDI-TOF MS.

In FIG. 12, the three mass spectra of samples A, B and C are illustrated. The undigested sample A shows two main peaks: the substrate at 2261.4 m/z, and the fucosylated product at 2407.7 m/z. The middle curve shows the mass spectrum of sample B, treated with N-glycosidase A, which hydrolyses both glycopeptides. The peak at 963.32 constitutes the deglycosylated product. The lower curve shows the mass spectrum of sample C. The N-glycosidase F is not able to hydrolyse α1,3-fucosylated substrates, so that the spectrum has the peak at 2406.7 m/z of the fucosylated product, whereas the peak of the hydrolysed substrate appears at 963.08 m/z.

Example 8

HPLC-Analysis of the pyridyl-aminated fucosyl Transferase Product

The two above-described samples (fucosylated product and negative control) were digested with N-glycosidase A. The oligosaccharides obtained were pyridyl-aminated and analysed by means of reverse phase HPLC (Wilson et al., 1998, glycobiology 8, 651-661; Kubelka et al., 1994, Arch. Biochem. Giophys. 308, 148-157; Hase et al., 1984, J. Biochem. 95, 197-203).

Figure 13:
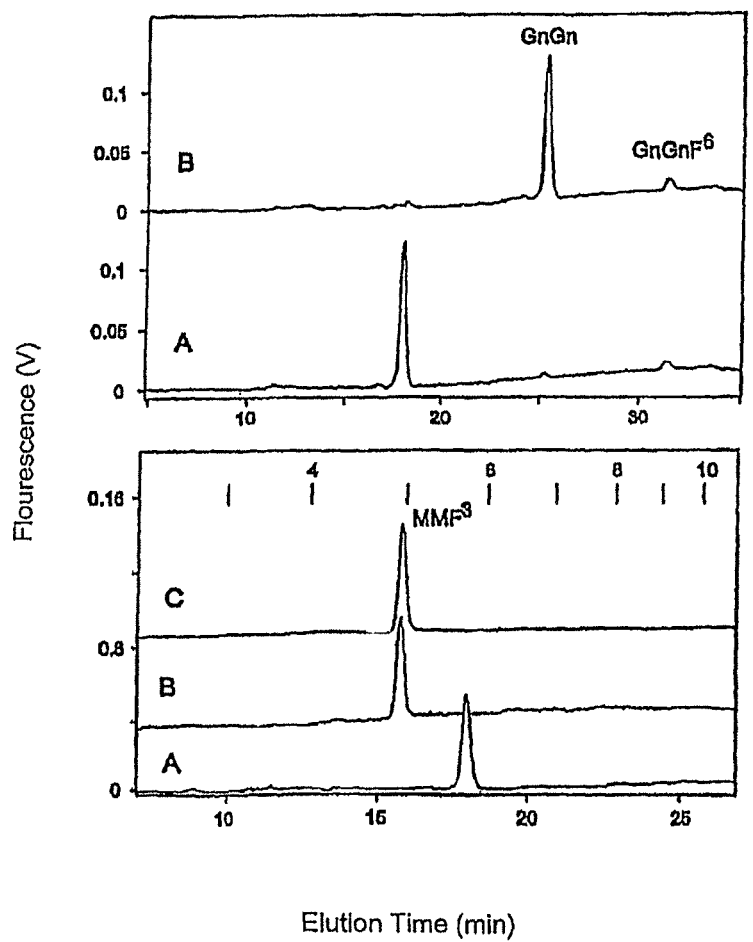
FIG. 13 shows the result of a HPLC.

In FIG. 13, the top diagram B represents the negative control, wherein in addition to the residual substrate (GnGn-peptide) α1,6-fucosylated product is visible. A has a peak at a substantially shorter retention time, which is specific of reducing fucose bound to GlcNAc-α1,3.

In the bottom diagram, the isolated transferase product prior to (curve A) and following (curve B) digestion by N-acetyl-βglucosaminidase was compared with $MMF^3$ honeybee phospholipase A, (curve C).

The invention claimed is:

1. A method of producing a recombinant glycoprotein, comprising expressing a recombinant glycoprotein in plants or plant cells, wherein an endogenous α1,3-fucosyltransferase production is suppressed or completely stopped,
   wherein said endogenous α1,3-fucosyltransferase is identified by sequence comparison with the α1,3-fucosyltransferase sequence according to SEQ ID NO: 1 with an open reading frame from base pair 211 to base pair 1740, and at least suppressing said endogenous α1,3-fucosyltransferase production.

2. The method of claim 1, wherein said endogenous α1,3-fucosyltransferase can be identified by sequence comparison with the α1,3-fucosyltransferase sequence according to SEQ ID NO: 1 with an open reading frame from base pair 211 to base pair 1740 by the program fastDB.

3. The method according to claim 1, wherein the glycoprotein is a human protein.

4. The method of claim 1, wherein the expression of the α1,3-fucosyltransferase is suppressed or completely blocked by a knock-out mutation of the endogenous α1,3-fucosyltransferase gene in said plant or plant cell.

5. The method of claim 1, wherein the expression of the α-1,3-fucosyltransferase is suppressed or completely blocked by antisense inhibition in said plant or plant cell.

6. The method of claim 1, wherein the expression of the α1,3-fucosyltransferase is suppressed or completely blocked by transfection with a polynucleotide comprising a sequence of at least 50 nucleotides which is complementary to the sequence coding for the endogenous α1,3-fucosyltransferase.

7. The method of claim 1, wherein the endogenous α1,3-fucosyltransferase activity in said plant or plant cell is less than 50% of the α1,3-fucosyltransferase occurring in natural plants or plant cells without α1,3-fucosyltransferase suppression.

8. A method of producing a recombinant glycoprotein, comprising expressing a recombinant glycoprotein in plants or plant cells, wherein an endogenous α1,3-fucosyltransferase production is suppressed or completely stopped, comprising identifying an endogenous α1,3-fucosyltransferase by (i) sequence comparison with the α1,3-fucosyltransferase sequence according to SEQ ID NO: 1 with an open reading frame from base pair 211 to base pair 1740 and (ii) assay for α1,3-fucosyltransferase activity, and suppressing or completely stopping said endogenous α1,3-fucosyltransferase production.

9. A method of producing plants or plant cells with reduced or stopped endogenous α1,3-fucosyltransferase activity, comprising identifying an endogenous α1,3-fucosyltransferase by (i) sequence comparison with the α1,3-fucosyltransferase sequence according to SEQ ID NO: 1 with an open reading frame from base pair 211 to base pair 1740 and (ii) assay for α1,3-fucosyltransferase activity, and suppressing or completely stopping said endogenous α1,3-fucosyltransferase production.

10. The method of claim 9, wherein said endogenous α1,3-fucosyltransferase can be identified by sequence comparison with the α1,3-fucosyltransferase sequence according to SEQ ID NO: 1 with an open reading frame from base pair 211 to base pair 1740 by the program fastDB.

11. The method of claim 9, wherein the expression of the α1,3-fucosyltransferase is suppressed or completely blocked by a knock-out mutation of the endogenous α1,3-fucosyltransferase gene in said plant or plant cell.

12. The method of claim 9, wherein the expression of the α1,3-fucosyltransferase is suppressed or completely blocked by antisense inhibition in said plant or plant cell.

13. The method of claim 9, wherein the expression of the α1,3-fucosyltransferase is suppressed or completely blocked by transfection with a polynucleotide comprising a sequence of at least 50 nucleotides which is complementary to the sequence coding for the endogenous α1,3-fucosyltransferase.

14. The method of claim 9, wherein the endogenous α1,3-fucosyltransferase activity in said plant or plant cell is less than 50% of the α1,3-fucosyltransferase occurring in natural plants or plant cells without α1,3-fucosyltransferase suppression.

* * * * *